US012041954B2

(12) United States Patent
Meydani et al.

(10) Patent No.: US 12,041,954 B2
(45) Date of Patent: Jul. 23, 2024

(54) COMPOSITIONS AND METHOD FOR TREATING AND PREVENTING COMPLICATIONS OF OBESITY

(71) Applicant: Tufts University, Medford, MA (US)

(72) Inventors: Simin Nikbin Meydani, Newton, MA (US); Mohsen Meydani, Newton, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 17/400,409

(22) Filed: Aug. 12, 2021

(65) Prior Publication Data

US 2021/0368844 A1 Dec. 2, 2021

Related U.S. Application Data

(63) Continuation of application No. 16/972,066, filed as application No. PCT/US2019/035957 on Jun. 7, 2019.

(60) Provisional application No. 62/681,935, filed on Jun. 7, 2018.

(51) Int. Cl.
| | |
|---|---|
| *A61K 9/14* | (2006.01) |
| *A23L 33/00* | (2016.01) |
| *A61K 36/23* | (2006.01) |
| *A61K 36/45* | (2006.01) |
| *A61K 36/752* | (2006.01) |
| *A61K 36/81* | (2006.01) |
| *A61K 36/899* | (2006.01) |

(52) U.S. Cl.
CPC ............... *A23L 33/30* (2016.08); *A61K 9/14* (2013.01); *A61K 36/23* (2013.01); *A61K 36/45* (2013.01); *A61K 36/752* (2013.01); *A61K 36/81* (2013.01); *A61K 36/899* (2013.01)

(58) Field of Classification Search
None
See application file for complete search history.

(56) References Cited

U.S. PATENT DOCUMENTS

| | | |
|---|---|---|
| 6,248,375 B1 | 6/2001 | Gilles et al. |
| 2003/0143287 A1 | 7/2003 | Bell |
| 2004/0220392 A1 | 11/2004 | Leo et al. |
| 2005/0003026 A1 | 1/2005 | Bok et al. |
| 2005/0123628 A1 | 6/2005 | Zabrecky |
| 2008/0206402 A1 | 8/2008 | DeMark et al. |
| 2011/0250318 A1* | 10/2011 | Innocenzi ............... A23L 2/66 426/72 |
| 2015/0313261 A1 | 11/2015 | Jewell et al. |
| 2016/0007639 A1* | 1/2016 | Smith ..................... A61Q 1/00 424/74 |
| 2017/0156388 A1 | 6/2017 | Gallardo et al. |

FOREIGN PATENT DOCUMENTS

| | | |
|---|---|---|
| CN | 104305180 | 1/2015 |
| JP | 2003-526354 | 9/2003 |
| JP | 2008-086217 | 4/2008 |
| JP | 2009-508508 | 3/2009 |

OTHER PUBLICATIONS

Liu, Health-Promoting Components of Fruits and Vegetables in the Diet, 2013, J American Society for Nutrition Adv Nutr, 4: 3845-3925.*
Roell et al., An Introduction to Terminology and Methodology of Chemical Synergy—Perspectives from Across Disciplines, 2017, Frontiers in Pharmacology, vol. B, article 158, pp. 1-11*
Aburasayn, H., et al. Targeting ceramide metabolism in obesity. Am J Physiol Endocrinol Metab. Aug. 1, 2016;311(2):E423-35.
Ali, AH et al., Recent advances in the development of farnesoid X receptor agonists. Ann Transl Med. Jan. 2015; 3(1): 5.
Alkhouri, et al. Non-high-density lipoprotein cholesterol (non-HDL-C) levels in children with nonalcoholic fatty liver disease (NAFLD). Springerplus. Aug. 5, 2014;3:407.
Arias-Loste, M.T., et al. The Crosstalk between Hypoxia and Innate Immunity in the Development of Obesity-Related Nonalcoholic Fatty Liver Disease. Biomed Res Int. 2015;2015:319745.
Baumruker, T., et al. Sphingolipids and the regulation of the immune response. Semin Immunol. Feb. 2002;14(1):57-63.
Bazzano, L.A., et al. Fruit and vegetable intake and risk of cardio-vascular disease in US adults: the first National Health and Nutrition Examination Survey Epidemiologic Follow-up Study. Am J Clin Nutr. Jul. 2002;76(1):93-9.
Bibbo, S., et al. Gut Microbiota as a Driver of Inflammation in Nonalcoholic Fatty Liver Disease. Mediators Inflamm. Jan. 31, 2018;2018:9321643.
Boesten, L.S., et al., Tumor necrosis factor-alpha promotes athero-sclerotic lesion progression in APOE*3-Leiden transgenic mice. Cardiovasc Res. Apr. 1, 2005;66(1):179-85.
Booth, A., et al. Adipose tissue: an endocrine organ playing a role in metabolic regulation. Horm Mol Biol Clin Investig. Apr. 1, 2016;26(1):25-42.
Bosy-Westphal, A., et al. Determinants of ectopic liver fat in metabolic disease. Eur J Clin Nutr. Feb. 2019;73(2):209-214.
Branen, L., et al., Inhibition of tumor necrosis factor-alpha reduces atherosclerosis in apolipoprotein E knockout mice. Arterioscler Thromb Vasc Biol. Nov. 2004;24(11):2137-42.
Callahan, B.J., et al., Bioconductor Workflow for Microbiome Data Analysis: from raw reads to community analyses. F1000Res. Jun. 24, 2016;5:1492.
Chatath, H., et al. Dyslipidemia in patients with nonalcoholic fatty liver disease. Semin Liver Dis. Feb. 2012;32(1):22-9.

(Continued)

*Primary Examiner* — Susan Hoffman
*Assistant Examiner* — Catheryne Chen
(74) *Attorney, Agent, or Firm* — Casimir Jones, S.C.; Tanya A. Arenson

(57) ABSTRACT

Provided herein are compositions and methods for treating, preventing, and reducing the risk of obesity and related diseases and conditions. In particular, provided herein is a composition comprising a dry powder of fruits and vegetables and uses thereof.

19 Claims, 29 Drawing Sheets

Specification includes a Sequence Listing.

(56) References Cited

OTHER PUBLICATIONS

Cheng, S., et al. Adipose Tissue Dysfunction and Altered Systemic Amino Acid Metabolism Are Associated with Non-Alcoholic Fatty Liver Disease. PLoS One. Oct. 6, 2015;10(10):e0138889.
Cinq-Frais et al. A signaling cascade mediated by ceramide, src and PDGFRβ coordinates the activation of the redox-sensitive neutral sphingomyelinase-2 and sphingosine kinase-1. Biochim Biophys Acta. Aug. 2013;1831(8):1344-56.
Database WPI Week 200438, Thompson Scientific, London, GB; AN 2004-401301 & CN1481710A (Gao S) Mar. 17, 2004.
Database WPI Week 200534, Thompson Scientific, London, GB; AN 2005-328628 & KR20040108265A (Univ Hallym) Dec. 23, 2004.
Database WPI Week 201631, Thomson Scientific, London, GB; AN 2016-08144V & CN 105249341A (Yingshang Tianhao Food Co Ltd) Jan. 20, 2016.
Database WPI Week 201648, Thompson Scientific, London, GB; AN 2016-23453W & CN105454965A (Shaanxi Haisheng Fresh Fruit Juice Co Lt) Apr. 6, 2016.
Database WPI Week 201755, Thompson Scientific, London, GB; AN 2017-48606S & CN106924545A (Zhang P) Jul. 7, 2017.
Database WPI Week 201810, Thompson Scientific, London, GB; AN 2018-08131J & CN107593852A (Guangdong Qichang Food Co Ltd) Jan. 19, 2018.
Database WPI Week 201811, Thompson Scientific, London, GB; AN 2017-87137G & CN107432337A (Wang L) Dec. 5, 2017.
Database WPI Week 201851, Thompson Scientific, London, GB; AN 2018-424077 & CN108065211A (Weihai Unisplendour Technology Park Co) May 28, 2018.
Dbaibo, G.S., et al. Ceramide generation by two distinct pathways in tumor necrosis factor alpha-induced cell death. FEBS Lett. Aug. 10, 2001;503(1):7-12.
De Taeye et al. Macrophage TNF-alpha contributes to insulin resistance and hepatic steatosis in diet-induced obesity. Am J Physiol Endocrinol Metab. Sep. 2007;293(3):E713-25.
Diehl, A.M., Tumor necrosis factor and its potential role in insulin resistance and nonalcoholic fatty liver disease. Clin Liver Dis. Aug. 2004;8(3):619-38, x.
Eheim, A., et al. Immune cells and metabolic dysfunction. Semin Immunopathol. Jan. 2014; 36(1):13-25.
Engin. Non-Alcoholic Fatty Liver Disease. Adv Exp Med Biol. 2017;960:443-467.
Esmaillzadeh, A., et al. Fruit and vegetable intakes, C-reactive protein, and the metabolic syndrome. Am J Clin Nutr. Dec. 2006;84(6):1489-97.
Extended European Search Report for 19814865.2, dated Feb. 16, 2022, 10 pages.
Farias Santos, J., Dietary intake of ain-93 standard diet induces Fatty liver with altered hepatic fatty acid profile in Wistar rats. Nutr Hosp. May 1, 2015;31(5):2140-6.
Gadaleta, R.M., et al. Farnesoid X receptor activation inhibits inflammation and preserves the intestinal barrier in inflammatory bowel disease. Gut. Apr. 2011;60(4):463-72.
Galic et al. Adipose tissue as an endocrine organ. Mol Cell Endocrinol. Mar. 25, 2010;316(2):129-39.
Geier et al. Cytokine-dependent regulation of hepatic organic anion transporter gene transactivators in mouse liver. Am J Physiol Gastrointest Liver Physiol. Nov. 2005;289(5):G831-41.
Gonzalez et al. Intestinal Farnesoid X Receptor Signaling Modulates Metabolic Disease. Dig Dis. 2017;35(3):178-184.
Goodrich et al. Conducting a microbiome study. Cell. Jul. 17, 2014;158(2):250-262.
Guzik et al. The role of infiltrating immune cells in dysfunctional adipose tissue. Cardiovasc Res. Jul. 1, 2017;113(9):1009-1023.
Holt et al. Fruit and vegetable consumption and its relation to markers of inflammation and oxidative stress in adolescents. J Am Diet Assoc. Mar. 2009;109(3):414-21.
Ilan. Compounds of the sphingomyelin-ceramide-glycosphingolipid pathways as secondary messenger molecules: new targets for novel therapies for fatty liver disease and insulin resistance. Am J Physiol Gastrointest Liver Physiol. Jun. 1, 2016;310(11):G1102-17.
International Search Report and Written Opinion for PCT/US2019/035957, dated Sep. 17, 2019, 59 pages.
Jeffery et al. Diet-microbiota interactions and their implications for healthy living. Nutrients. Jan. 17, 2013;5(1):234-52.
Jiang et al. Intestinal farnesoid X receptor signaling promotes nonalcoholic fatty liver disease. J Clin Invest. Jan. 2015;125(1):386-402.
Kakino et al. Pivotal Role of TNF-α in the Development and Progression of Nonalcoholic Fatty Liver Disease in a Murine Model. Horm Metab Res. Jan. 2018;50(1):80-87.
Katsiki et al. Non-alcoholic fatty liver disease and dyslipidemia: An update. Metabolism. Aug. 2016;65(8):1109-23.
Kim et al. A dysregulated acetyl/SUMO switch of FXR promotes hepatic inflammation in obesity. EMBO J. Jan. 13, 2015;34(2):184-99.
Kim et al. Repression of farnesoid X receptor during the acute phase response. J Biol Chem. Mar. 14, 2003;278(11):8988-95.
Kong et al. Dietary patterns differently associate with inflammation and gut microbiota in overweight and obese subjects. PLoS One. Oct. 20, 2014;9(10):e109434.
Kriss et al. Low diversity gut microbiota dysbiosis: drivers, functional implications and recovery. Curr Opin Microbiol. Aug. 2018;44:34-40.
Li et al. Gut Microbiota Dysbiosis Drives and Implies Novel Therapeutic Strategies for Diabetes Mellitus and Related Metabolic Diseases. Front Immunol. Dec. 20, 2017;8:1882.
Li et al., Bile acid receptors in non-alcoholic fatty liver disease. Biochem Pharmacol. Dec. 1, 2013;86(11):1517-24.
Lozupone et al. Species divergence and the measurement of microbial diversity. FEMS Microbiol Rev. Jul. 2008;32(4):557-78.
Martin et al., Redox regulation of neutral sphingomyelinase-1 activity in HEK293 cells through a GSH-dependent mechanism. Archives of Biochemistry and Biophysics. Mar. 15, 2007, 459(2); 295-300.
McKellar et al. Role for TNF in atherosclerosis? Lessons from autoimmune disease. Nat Rev Cardiol. Jun. 2009;6(6):410-7.
Meydani et al. Long-term vitamin E supplementation reduces atherosclerosis and mortality in Ldlr-/- mice, but not when fed Western style diet. Atherosclerosis. Mar. 2014;233(1):196-205.
Mizrahi et al. Plant foods and the risk of cerebrovascular diseases: a potential protection of fruit consumption. Br J Nutr. Oct. 2009;102(7):1075-83.
Nakamura et al. Cotton rat (*Sigmodon hispidus*) develops metabolic disorders associated with visceral adipose inflammation and fatty pancreas without obesity. Cell Tissue Res. Feb. 2019;375(2):483-492.
Nie et al., MicroRNA-194 inhibition improves dietary-induced non-alcoholic fatty liver disease in mice through targeting on FXR. Biochim Biophys Acta Mol Basis Dis. Dec. 2017;1863(12):3087-3094.
Nikolova-Karakashian. Alcoholic and non-alcoholic fatty liver disease: Focus on ceramide. Adv Biol Regul. Dec. 2018;70:40-50.
Ohta et al. Disruption of tumor necrosis factor-alpha gene diminishes the development of atherosclerosis in ApoE-deficient mice. Atherosclerosis. May 2005;180(1):11-7.
Paniagua. Nutrition, insulin resistance and dysfunctional adipose tissue determine the different components of metabolic syndrome. World J Diabetes. Nov. 15, 2016;7(19):483-514.
Paredes-Turrubiarte et al. Severity of non-alcoholic fatty liver disease is associated with high systemic levels of tumor necrosis factor alpha and low serum interleukin 10 in morbidly obese patients. Clin Exp Med. May 2016;16(2):193-202.
Polyzos et al. Adipose tissue, obesity and non-alcoholic fatty liver disease. Minerva Endocrinol. Jun. 2017;42(2):92-108.
Qin et al. A metagenome-wide association study of gut microbiota in type 2 diabetes. Nature. Oct. 4, 2012;490(7418):55-60.
Regnier et al. Sphingolipid metabolism in non-alcoholic fatty liver diseases. Biochimie. Apr. 2018;159:9-22.
Rehman et al. Role of Interleukin-6 in Development of Insulin Resistance and Type 2 Diabetes Mellitus. Crit Rev Eukaryot Gene Expr. 2017;27(3):229-236.

(56) References Cited

OTHER PUBLICATIONS

Ridaura et al. Gut microbiota from twins discordant for obesity modulate metabolism in mice. Science. Sep. 6, 2013;341(6150):1241214.
Root et al. Combined fruit and vegetable intake is correlated with improved inflammatory and oxidant status from a cross-sectional study in a community setting. Nutrients. Jan. 2012;4(1):29-41.
Saltzman et al. Intestinal Microbiome Shifts, Dysbiosis, Inflammation, and Non-alcoholic Fatty Liver Disease. Front Microbiol. Jan. 30, 2018;9:61.
Samad et al. Adipose tissue and ceramide biosynthesis in the pathogenesis of obesity. Adv Exp Med Biol. 2011;721:67-86.
Santos et al. Choline and Cystine Deficient Diets in Animal Models with Hepatocellular Injury: Evaluation of Oxidative Stress and Expression of RAGE, TNF-$\alpha$, and IL-1$\beta$. Oxid Med Cell Longev. 2015;2015:121925.
Sanyal et al. A Lipidomic Readout of Disease Progression in A Diet-Induced Mouse Model of Nonalcoholic Fatty Liver Disease. Trans Am Clin Climatol Assoc. 2015;126:271-88.
Schmidt-Arras et al. IL-6 pathway in the liver: From physiopathology to therapy. J Hepatol. Jun. 2016;64(6):1403-15.
Schmitt et al. Protective effects of farnesoid X receptor (FXR) on hepatic lipid accumulation are mediated by hepatic FXR and independent of intestinal FGF15 signal. Liver Int. Apr. 2015;35(4):1133-1144.
Schutze, S. et al., The role of diacylglycerol and ceramide in tumor necrosis factor and interleukin-1 signal transduction. J Leukoc Biol. Nov. 1994;56(5):533-41.
Seo et al. Tumor Necrosis Factor-$\alpha$ as a Predictor for the Development of Nonalcoholic Fatty Liver Disease: A 4-Year Follow-Up Study. Endocrinol Metab (Seoul). Mar. 2013;28(1):41-5.
Serafini et al. Functional Foods for Health: The Interrelated Antioxidant and Anti-Inflammatory Role of Fruits, Vegetables, Herbs, Spices and Cocoa in Humans. Curr Pharm Des. 2016;22(44):6701-6715.
Sheflin et al. Linking dietary patterns with gut microbial composition and function. Gut Microbes. Mar. 4, 2017;8(2):113-129.
Sittipo et al. Intestinal microbiota and the immune system in metabolic diseases. J Microbiol. Mar. 2018;56(3):154-162.
Strissel et al. Adipocyte death, adipose tissue remodeling, and obesity complications. Diabetes. Dec. 2007;56(12):2910-8.
Tindall et al. Dietary Patterns Affect the Gut Microbiome—The Link to Risk of Cardiometabolic Diseases. J Nutr. Sep. 1, 2018;148(9):1402-1407.
Turnbaugh et al. A core gut microbiome in obese and lean twins. Nature. Jan. 22, 2009;457(7228):480-4.
Van Beek et al. The limited storage capacity of gonadal adipose tissue directs the development of metabolic disorders in male C57BI/6J mice. Diabetologia. Jul. 2015;58(7):1601-9.
Van Greevenbroek et al. Dysfunctional adipose tissue and low-grade inflammation in the management of the metabolic syndrome: current practices and future advances. F1000Res. Oct. 13, 2016;5:F1000 Faculty Rev-2515.
Wang et al. Non-HDL-cholesterol to HDL-cholesterol ratio is a better predictor of new-onset non-alcoholic fatty liver disease than non-HDL-cholesterol: a cohort study. Lipids Health Dis. Aug. 21, 2018;17(1):196.
Wang, YD et al., Farnesoid X receptor antagonizes nuclear factor $\kappa$B in hepatic inflammatory response. Hepatology. Nov. 2008;48(5):1632-43.
Wannamethee et al. Associations of vitamin C status, fruit and vegetable intakes, and markers of inflammation and hemostasis. Am J Clin Nutr. Mar. 2006;83(3):567-74; quiz 726-7.
Wei et al. Spontaneous development of hepatosteatosis in perilipin-1 null mice with adipose tissue dysfunction. Biochim Biophys Acta Mol Cell Biol Lipids. Feb. 2018;1863(2):212-218.
Wieland et al. Systematic review: microbial dysbiosis and nonalcoholic fatty liver disease. Aliment Pharmacol Ther. Nov. 2015;42(9):1051-63.
Wong. Gut microbiota and cardiometabolic outcomes: influence of dietary patterns and their associated components. Am J Clin Nutr. Jul. 2014;100 Suppl 1:369S-77S.
Xie et al. An Intestinal Farnesoid X Receptor-Ceramide Signaling Axis Modulates Hepatic Gluconeogenesis in Mice. Diabetes. Mar. 2017;66(3):613-626.
Yanaga et al. Tumor necrosis factor alpha stimulates sphingomyelinase through the 55 kDa receptor in HL-60 cells. FEBS Lett. Dec. 21, 1992;314(3):297-300.
Yao et al. A selective gut bacterial bile salt hydrolase alters host metabolism. Elife. Jul. 17, 2018;7:e37182.
Yousef et al. Fatty liver without a large "belly": Magnified review of non-alcoholic fatty liver disease in non-obese patients. World J Gastrointest Pathophysiol. Aug. 15, 2017;8(3):100-107.
Zelber-Sagi et al. Non-high-density lipoprotein cholesterol independently predicts new onset of non-alcoholic fatty liver disease. Liver Int. Jul. 2014;34(6):e128-35.
Zhang et al. Cruciferous vegetable consumption is associated with a reduced risk of total and cardiovascular disease mortality. Am J Clin Nutr. Jul. 2011;94(1):240-6.
Zhang et al. Nonalcoholic Fatty Liver Disease: Dyslipidemia, Risk for Cardiovascular Complications, and Treatment Strategy. J Clin Transl Hepatol. Mar. 2015;3(1):78-84.
Office Action for JP 2020-568265, dated Jun. 6, 2023, 2 pages.
Office Action for CA 3103211, dated Jun. 20, 2023, 6 pages.

\* cited by examiner

FIG. 10A

| | % | F&V (g/d) ᵃ | F&V (g/d) ᵇ |
|---|---|---|---|
| Orange | 13.64 | 5.47 | 8.80 |
| Apple | 8.59 | 3.85 | 6.24 |
| Banana | 5.68 | 2.28 | 3.69 |
| Grape (Black and Green) | 4.17 | 1.67 | 2.71 |
| Watermelon | 3.28 | 1.32 | 2.14 |
| Pineapple | 2.92 | 1.17 | 1.90 |
| Strawberries | 2.01 | 0.80 | 1.31 |
| Cantaloupe | 1.94 | 0.78 | 1.26 |
| Lemons | 1.91 | 0.77 | 1.24 |
| Grapefruit | 1.89 | 0.76 | 1.23 |
| Peaches | 1.76 | 0.70 | 1.14 |
| Pears | 1.24 | 0.50 | 0.81 |
| Potato | 17.29 | 6.93 | 11.26 |
| Tomato | 13.53 | 5.42 | 8.80 |
| Sweet Corn | 3.78 | 1.51 | 2.46 |
| Onions (White, Red, Yellow) | 3.22 | 1.29 | 2.09 |
| Head Lettuce (Iceberg) | 2.43 | 0.97 | 1.58 |
| Romaine | 1.68 | 0.67 | 1.09 |
| Bell Peppers (Red, Green, Yellow) | 1.66 | 0.67 | 1.08 |
| Carrots | 1.55 | 0.62 | 1.01 |
| Cucumbers | 1.44 | 0.58 | 0.94 |
| Cabbage (Red, Green) | 1.21 | 0.48 | 0.78 |
| Dry Beans1 | 1.13 | 0.45 | 0.73 |
| Sweet Potato2 | 1.12 | 0.45 | 0.73 |

K

D

COMPOSITIONS AND METHOD FOR TREATING AND PREVENTING COMPLICATIONS OF OBESITY

This application is a continuation of U.S. patent application Ser. No. 16/972,066, filed Dec. 4, 2020, which claims priority to U.S. provisional patent application Ser. No. 62/681,935, filed Jun. 7, 2018, which is incorporated herein by reference in their entirety.

STATEMENT REGARDING FEDERALLY SPONSORED RESEARCH OR DEVELOPMENT

This invention was made with government support under grant number 58-1950-4-003 awarded by the United States Department of Agriculture. The government has certain rights in the invention.

FIELD

Provided herein are compositions and methods for treating, preventing, and reducing the risk of obesity and related diseases and conditions. In particular, provided herein is a composition comprising a dry powder of fruits and vegetables and uses thereof.

BACKGROUND

The prevalence of obesity and metabolic disorders is rapidly increasing around the world. In addition to metabolic disorders, obesity is associated with coronary heart disease, type 2 diabetes, certain types of cancer, high blood pressure, stroke, liver and gallbladder disease, sleep apnea and respiratory problems, osteoarthritis, and gynecological problems in females.

Metabolic disorders are defined as dysfunction of metabolically active tissues such as adipose tissue and liver. Dysregulated immune response as manifested by increased inflammation is one of the major contributors to the development of metabolic disorder (Eheim et al., 2014; Sittipo et al., 2018). Adipose tissue, once viewed solely as an energy reservoir, is currently recognized as an endocrine organ that functions in regulation of metabolism (Booth et al., 2016; Galic et al., 2010). When the dietary lipid load exceeds the storage capacity of dysfunctional adipose tissue, overflow of free fatty acids will spill into circulation resulting in ectopic lipid accumulation in other tissues such as liver (Bosy-Westphal et al., 2019). Accumulation of fat in the liver can result in non-alcoholic fatty liver disease (NAFLD). NAFLD, the leading cause of chronic liver disease, may either be associated with (Arias-Loste et al., 2015; Polyzos et al., 2017) or be independent of obesity (Nakamura et al., 2018; Yousef et al., 2017). In animal studies, diet-induced NAFLD was found not only in mice fed a high fat diet (typically 45% to 60% of calories from fat) but also in those fed the standard AIN-93 diet (16% of calories from fat) (Farias Santos et al., 2015; Santos et al., 2015).

There is an urgent need for compositions for treating and preventing disorders associated with obesity such as metabolic and cardiovascular disorders.

SUMMARY

The present disclosure provides compositions and methods for treating and preventing obesity and related complications. Experiments described herein utilized a fruit and vegetable (F&V) mixture comprising 24 F&V. Supplementing mice on a Basal or high fat (HF) diet with 15% F&V mixture (w/w) (equivalent to 8-9 servings of F&V/day for humans) prevented hepatic steatosis and suppressed epididymal adipose tissue inflammation, independent of weight loss. These effects correlated with lower levels of pro-inflammatory cytokine TNFα and ceramides, as well as increased gut microbiota diversity and altered gut bacterial composition. Further experiments demonstrated prevention of HF-induced atherosclerosis and hepatic steatosis, which may be mediated through improved dyslipidemia and reduced inflammation.

Accordingly, provided herein is a composition, comprising: a dry powder (e.g., freeze-dried powder) comprising a mixture of fruit species and a mixture of vegetables species. In some embodiments, the composition is a nutritional supplement (e.g., tablet, powder, capsule, etc.), food, or beverage.

The present disclosure is not limited to particular fruits and vegetables or components of a F&V composition. In some embodiments, the fruit species are one or more (e.g., 1, 2, 3, 4, 5, 6, 7, 8, 9, 10, 11, or all) fruit species selected from, for example, oranges, apples, bananas, grapes, watermelon, pineapple, strawberries, cantaloupe, lemons, grapefruit, peaches, or pears. In some embodiments, the vegetable species are one or more (e.g., 1, 2, 3, 4, 5, 6, 7, 8, 9, 10, 11, or all) selected from, for example, potatoes, tomatoes, sweet corn, onions, head lettuce, romaine, bell peppers, carrots, cucumbers, cabbage, beans, or sweet potato. In some embodiments, the composition comprises at least the recommended daily levels of fruits and vegetables for a particular subject (e.g., at least 1, 2, 3, 4, 5, 6, 7, 8, 9, 10, 15, or more times the recommended daily levels). In some embodiments, a composition intended to provide a daily dose comprises 40-65 grams of dry powder. In some embodiments, the mixture of fruits and vegetables comprises the specific F&V in the amounts listed in FIG. 10A or B. In some embodiments, the mixture of fruit and vegetable species comprises (all percentages are w/w of the F&V mixture) at least one of 16-20% oranges, 14-18% tomatoes, 8-11% apples, 13-16% potatoes, 3.0-5.5% bananas, 3-4% sweet corn, 3-4% grapes, 2-3% lettuce, 1-2% escarole, 1-2% brussels sprouts, 1-2% cabbage, 1-2% carrots, 1-3% onions, 1-2% green peas, 0.5-1.5% watermelon, 0.5-1.5% honeydew melon, 0.5-1.5% broccoli, 1-2% spinach, 0.5-1.5% peppers, 0.5-1.5% snap beans, 0.5-1.5% cantaloupe, 0.4-1.2% cauliflower, 0.5-1.0% mangoes, 0.5-1.0% papaya, 0.3-0.9% celery, 0.4-1.2% cucumbers, 0.5-1.0% pineapple, 0.25-0.75% tangerines, 0.25-0.75% limes, 0.25-0.75% strawberries, 0.25-0.75% raspberries, 0.25-0.75% grapefruit, 0.25-0.75% lemons, 0.25-0.75% cranberries, 0.3-0.5% plums, 0.3-0.5% peaches, 0.3-0.5% cherries, 0.3-0.5% blueberries, 0.3-0.5% apricots, 0.1-0.15% dried peas, 0.1-0.15% great northern beans, 0.1-0.15% dried navy beans, 0.1-0.15% dried lentils, 0.1-0.15% pinto beans, 0.1-0.15% lima beans, 0.1-0.15% red kidney beans, and 0.1-0.15% black beans (e.g., approximately 18.075% oranges, 16.161% tomatoes, 9.595% apples, 14.493% potatoes, 4.373% bananas, 3.564% sweet corn, 3.383% grapes, 2.537% lettuce, 1.651% escarole, 1.375% brussels sprouts, 1.375% cabbage, 1.329% carrots, 2.017% onions, 1.293% green peas, 1.058% watermelon, 1.058% honeydew melon, 0.84% broccoli, 1.651% spinach, 1.087% peppers, 1.061% snap beans, 1.058% cantaloupe, 0.84% cauliflower, 0.732% mangoes, 0.732% papaya, 0.626% celery, 0.814% cucumbers, 0.732% pineapple, 0.555% tangerines, 0.555% limes, 0.437% strawberries, 0.437% raspberries, 0.555% grapefruit, 0.555% lemons, 0.437% cranberries, 0.388% plums, 0.388% peaches, 0.388% cherries, 0.437% blueberries, 0.388% apricots, 0.121% dried peas, 0.121% great northern beans, 0.121% dried navy beans, 0.121% dried lentils, 0.121% pinto beans, 0.121% lima beans, 0.121% red kidney beans, and 0.121% black beans).

In some embodiments, the F&V mixture comprises a polyphenol content of 15-25% hesperetin, 15-25% caffeoylquinic acid, 10-20% quercetin, and 5-15% malvidin (e.g., 20.6% hesperetin, 19.1% caffeoylquinic acid, 15.7% quercetin, and 10.3% malvidin). In some embodiments, the composition further comprises 1-10% naringenin, 1-10% pelargonidin, 1-5% catechin, and 1-5% procyanidin (e.g., 6.5% naringenin, 5.8% pelargonidin, 4.2% catechin, and 3.1% procyanidin). In some embodiments, the composition further comprises one or more polyphenols selected from, for example, caffeic acid, peonidin, cyanidin, pinoresinol, p-Coumaroyl, luteolin, petunidin, daidzein, genistein, ellagic acid, or gallic acid.

Additional embodiments provide a composition, comprising, consisting essentially of, or consisting of: a dry powder comprising 16-20% oranges, 14-18% tomatoes, 8-11% apples, 13-16% potatoes, 3.0-5.5% bananas, 3-4% sweet corn, 3-4% grapes, 2-3% lettuce, 1-2% escarole, 1-2% brussels sprouts, 1-2% cabbage, 1-2% carrots, 1-3% onions, 1-2% green peas, 0.5-1.5% watermelon, 0.5-1.5% honeydew melon, 0.5-1.5% broccoli, 1-2% spinach, 0.5-1.5% peppers, 0.5-1.5% snap beans, 0.5-1.5% cantaloupe, 0.4-1.2% cauliflower, 0.5-1.0% mangoes, 0.5-1.0% papaya, 0.3-0.9% celery, 0.4-1.2% cucumbers, 0.5-1.0% pineapple, 0.25-0.75% tangerines, 0.25-0.75% limes, 0.25-0.75% strawberries, 0.25-0.75% raspberries, 0.25-0.75% grapefruit, 0.25-0.75% lemons, 0.25-0.75% cranberries, 0.3-0.5% plums, 0.3-0.5% peaches, 0.3-0.5% cherries, 0.3-0.5% blueberries, 0.3-0.5% apricots, 0.1-0.15% dried peas, 0.1-0.15% great northern beans, 0.1-0.15% dried navy beans, 0.1-0.15% dried lentils, 0.1-0.15% pinto beans, 0.1-0.15% lima beans, 0.1-0.15% red kidney beans, and 0.1-0.15% black beans.

Certain embodiments provide a food or beverage product comprising a composition as described herein. In some embodiments, the product comprises 2%-20% (e.g., 5-15%, 5-20%, or 5-10%) (w/w) of the composition. In some embodiments, the food or beverage product comprises one or more of protein, carbohydrates, and fat (e.g., 5-15% protein (kcal/kcal), 75-85% carbohydrates (kcal/kcal), and 0-20% fats (kcal/kcal); 10-12% protein (kcal/kcal), 80-83% carbohydrates (kcal/kcal), and 5-10% fat (kcal/kcal), or 11.6% protein (kcal/kcal), 81.2% carbohydrates, and 7.2% fats (kcal/kcal).

Further embodiments provide a nutritional supplement comprising a composition as described herein.

Yet other embodiments provide a composition as described herein for use in a method of treating and/or preventing one or more conditions selected from, for example, weight gain, obesity, inflammatory conditions, fatty liver disease, high cholesterol, glucose intolerance, insulin resistance, low gut microbiota diversity, heart disease, or atherosclerosis.

Still other embodiments provide a composition as described herein for use in a method of any one or more of the following: decreasing fat mass, increasing muscle mass, reducing inflammatory cytokines and/or ceramides, reducing tissue inflammation, decreasing cholesterol, improving glucose tolerance, improving immune response, increasing gut microbiota diversity, increasing lifespan, improving cognition, or improving bone health.

Also provided herein is the use of a composition as described herein for treating and/or preventing one or more conditions selected from weight gain, obesity, inflammatory conditions, fatty liver disease, high cholesterol, glucose intolerance, insulin resistance, low gut microbiota diversity, heart disease, and atherosclerosis.

Further provided herein is the use of a composition as described herein in decreasing fat mass, increasing muscle mass, reducing inflammatory cytokines and/or ceramides, reducing tissue inflammation, decreasing cholesterol, improving glucose tolerance, treating or preventing atherosclerosis, improving immune response, increasing gut microbiota diversity, increasing lifespan, improving cognition, and/or improving bone health.

Still further embodiments provide a method of treating and/or preventing one or more conditions selected from, for example, weight gain, obesity, inflammatory conditions, fatty liver disease, high cholesterol, glucose intolerance, insulin resistance, low gut microbiota diversity, heart disease, and atherosclerosis in a subject, comprising: administering a composition as described herein to the subject.

Embodiments of the disclosure provide a method of decreasing fat mass, increasing muscle mass, reducing inflammatory cytokines and/or ceramides, reducing tissue inflammation, decreasing cholesterol, improving glucose tolerance, improving immune response, increasing gut microbiota diversity, increasing lifespan, improving cognition, and/or improving bone health in a subject, comprising: administering a composition as described herein to the subject.

In some embodiments, the subject is a human. In some embodiments, the subject exhibits one or more signs or symptoms of the condition and the administering reduces or eliminates the signs or symptoms. In some embodiments, the administering comprises administering at least a daily dose equivalent to at least 5 servings of F&V for the subject (e.g., 40-65 grams of dry powder per day). In some embodiments, the administering is repeated one or more (e.g., 1, 2, 3, or more) times per day for a period of at least 1 week (e.g., at least 1 month, at least one year, multiple years, or indefinitely).

Additional embodiments are described herein.

DESCRIPTION OF THE DRAWINGS

FIG. 10A-C shows exemplary compositions of the fruit and vegetable components of animal diets.

FIG. 27 shows that F&V supplementation improved dyslipidemia in LDLR KO mouse. (A-D) Plasma lipid profiles of (A) cholesterol, (B) triglycerides, (C) HDL, and (E) LDL.

DEFINITIONS

Figure 1:
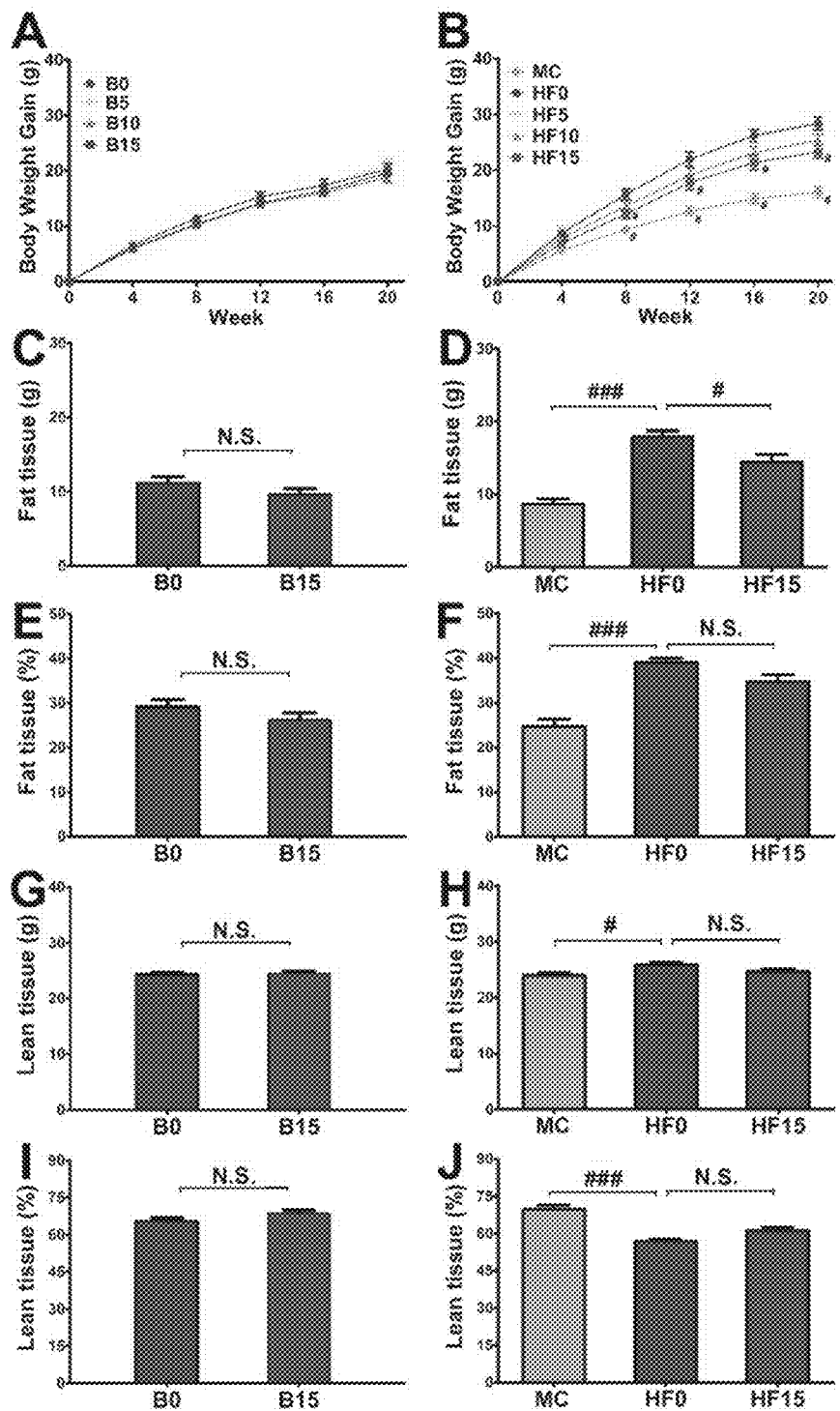
FIG. 1 shows that mice fed HF diet with F&V supplementation had less body weight gain and fat tissue mass. Six-week old male C57BL/6J mice were fed a basal diet (B, 16 kcal % fat) or high fat diet (HF, 45 kcal % fat) with 0%, 5%, 10%, or 15% F&V supplementation, respectively, for 20 weeks. Mice fed a matched control diet (MC, 10 kcal % fat) were used as control for HF diet. (A, B) Body weight; (C, D, E, F) Fat tissue; (G, H, I, J) Lean tissue. Data are presented as mean±SEM. #$P<0.05$, ###$P<0.001$, and N.S. not significant.

Although any methods and materials similar or equivalent to those described herein can be used in the practice or testing of embodiments described herein, some preferred methods, compositions, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. As used herein, the terms "comprise", "include", and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the terms "co-administration" and variations thereof refer to the administration of at least two agent(s) or therapies to a subject (e.g., a composition disclosed herein and one or more therapeutic agents). In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the terms "prevent," "prevention," and preventing" may refer to reducing the likelihood of a particular condition or disease state (e.g., metabolic disorder or other complication of obesity) from occurring in a subject not presently experiencing or afflicted with the condition or disease state. The terms do not necessarily indicate complete or absolute prevention. For example "preventing metabolic disorder" refers to reducing the likelihood of metabolic disorder and related conditions occurring in a subject not presently experiencing or diagnosed with metabolic disorder. The terms may also refer to delaying the onset of a particular condition or disease state (e.g., metabolic disorder) in a subject not presently experiencing or afflicted with the condition or disease state. In order to "prevent metabolic disorder" a composition or method need only reduce the likelihood and/or delay the onset of metabolic disorder or related condition, not completely block any possibility thereof. "Prevention," encompasses any administration or application of a therapeutic or technique to reduce the likelihood or delay the onset of a disease developing (e.g., in a mammal, including a human). Such a likelihood may be assessed for a population or for an individual.

As used herein, the terms "treat," "treatment," and "treating" refer to reducing the amount or severity of a particular condition, disease state (e.g., metabolic disorders or other complications of obesity), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process.

As used herein, the term w/w (weight/weight) refers to the amount of a given substance in a composition on weight basis. For example, a composition comprising 50% w/w carrots means that the mass of the carrots is 50% of the total mass of the composition (i.e., 50 grams of carrots in 100 grams of the composition, such as a mixture of F&V).

As used herein, the terms "food" and "food products" refer to products and ingredients therefore, taken by the mouth, the constituents of which are active in and/or absorbed by the G.I. tract with the purpose of nourishment of the body and its tissues, refreshment and indulgence, which products are to be marketed and sold to customers for consumption by humans. Examples of foods and food and beverage products include, but are not limited to, tea; spreads; ice cream; frozen fruits and vegetables; snacks including diet foods and beverages; condiments; and culinary aids. In some embodiments, a "food" is a material comprising protein, carbohydrate and/or fat, which is used in the body of an organism to sustain growth, repair and vital processes and to furnish energy. Foods may also contain supplementary substances such as minerals, vitamins and condiments. See Merriam-Webster's Collegiate Dictionary, 10th Edition, 1993.

As used herein a "food additive" (e.g., as defined by the FDA in 21 C.P.R. 170.3 (e)(1)) includes direct and indirect additives.

As used herein, a "dietary supplement" is a product that is intended to supplement a diet. In some embodiments, dietary supplements contain little or no calories.

As used herein, the term "subject" as used herein includes all members of the animal kingdom including mammals, and suitably refers to humans.

DETAILED DESCRIPTION

Obesity-induced alteration in adipose tissue, especially visceral white adipose tissue, is characterized by infiltrated macrophages and other inflammatory cells, release of cytokines and chemokines such as monocyte chemoattractant protein-1 (MCP-1), interleukin-6 (IL-6), and tumor necrosis factor-alpha (TNF-α), increased lipolysis, and death of adipocytes, all of which play a critical role in pathogenesis of NAFLD (Cheng et al., 2015; Wei et al., 2018). In particular, TNFα has been found to play a pivotal role in the development and progression of NAFLD in murine models. High circulating levels of TNFα is associated with the severity of NAFLD in morbidly obese patients (Kakino et al., 2018; Paredes-Turrubiarte et al., 2016). TNFα stimulates liver ceramide generation (Dbaibo et al., 2001; Engin, 2017), a unique class of sphingolipid signaling lipid molecules that are involved in pathogenesis of NAFLD (Nikolova-Karakashian, 2018), indicating that TNFα and ceramides may additively or synergistically promote NAFLD. Ceramide can be formed by de novo synthesis pathway or through the salvage pathway using ceramide synthase. It may also be produced from sphingomyelin via the function of enzyme sphingomyelinase, the activity of which is increased by oxidative stress and TNFα.

The farnesoid X receptor (FXR), a nuclear receptor abundantly expressed in liver, is a key regulator controlling various hepatic metabolic processes. Hepatic FXR activation inhibits the expression of pro-inflammatory genes, including that of TNFα, by blocking NFκB activation (Kim et al., 2015; Wang et al., 2008). Further, hepatic FXR expression levels were lower in NAFLD patients (Yang et al., 2010) and diet-induced mice NAFLD (Nie et al., 2017). FXR is a potential drug target for treatment of NAFLD (Ali et al., 2015; Li et al., 2013).

Gut microbial dysbiosis, characterized by low diversity and altered composition of gut microbiota, has been shown to be associated with obesity and metabolic disorders in humans (Qin et al., 2012; Turnbaugh et al., 2009) and causally related to these disorders in rodent models (Kriss et al., 2018; Li et al., 2017; Ridaura et al., 2013). Furthermore, gut microbiota dysbiosis may contribute to NAFLD pathogenesis (Bibbo et al., 2018; Saltzman et al., 2018; Wieland et al., 2015).

Dietary patterns affect gut microbiota, oxidative stress, inflammation, and metabolism (Kong et al., 2014; Sheflin et al., 2017; Tindall et al., 2018; Wong, 2014). Experiments described herein determined the impact of increased consumption of F&V on metabolic disorders and its underlying mechanisms. Results indicated that high intake of a variety of F&V completely prevented metabolic dysfunction of adipose tissue and NAFLD independent of body weight reduction. Furthermore, these data show that these effects of F&V on metabolic disorders are associated with increased gut microbiota diversity and reduction in pro-inflammatory cytokine and ceramide levels.

Further experiments demonstrated that mice fed HF diet had significantly higher plasma TG and LDL and lower HDL levels than mice fed LF diet, and this dyslipidemia was prevented by F&V supplementation. Further, the HF+FV group had lower plasma TNFα levels compared to HF0 group (p<0.05). Spearman correlation analysis showed that aortic atherosclerotic lesion and hepatic steatosis area were negatively correlated with plasma HDL (p<0.001) and significantly and positively correlated with TNFα, and the ratios of LDL/HDL, TG/HDL, and non HDL/HDL.

Figure 10B:
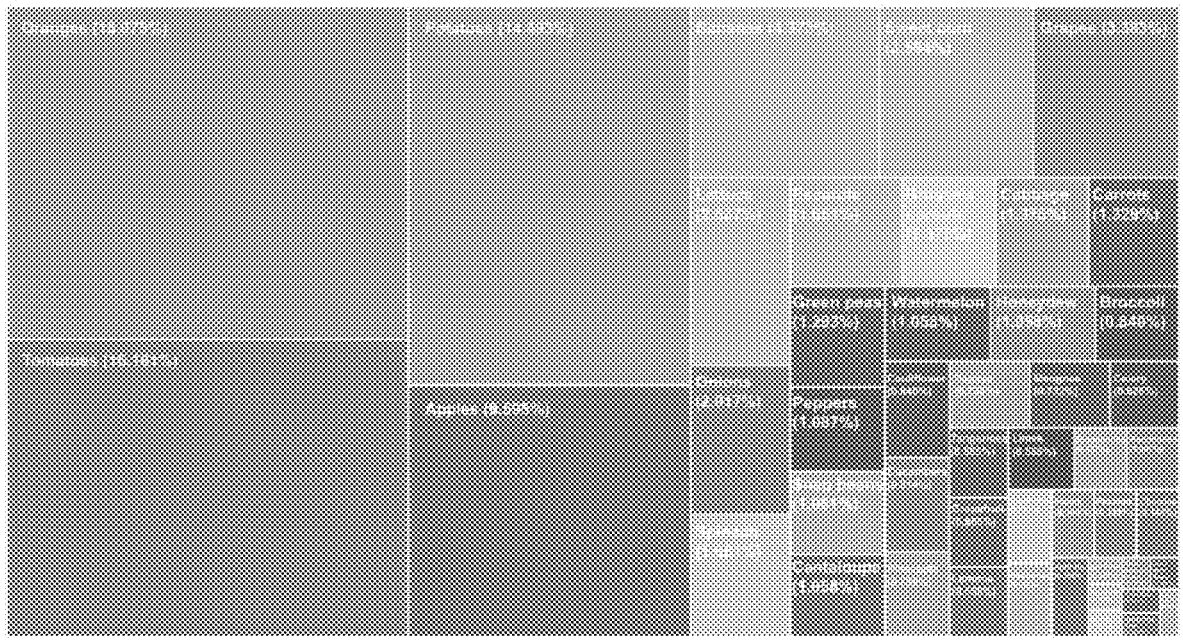
Figure 10C:
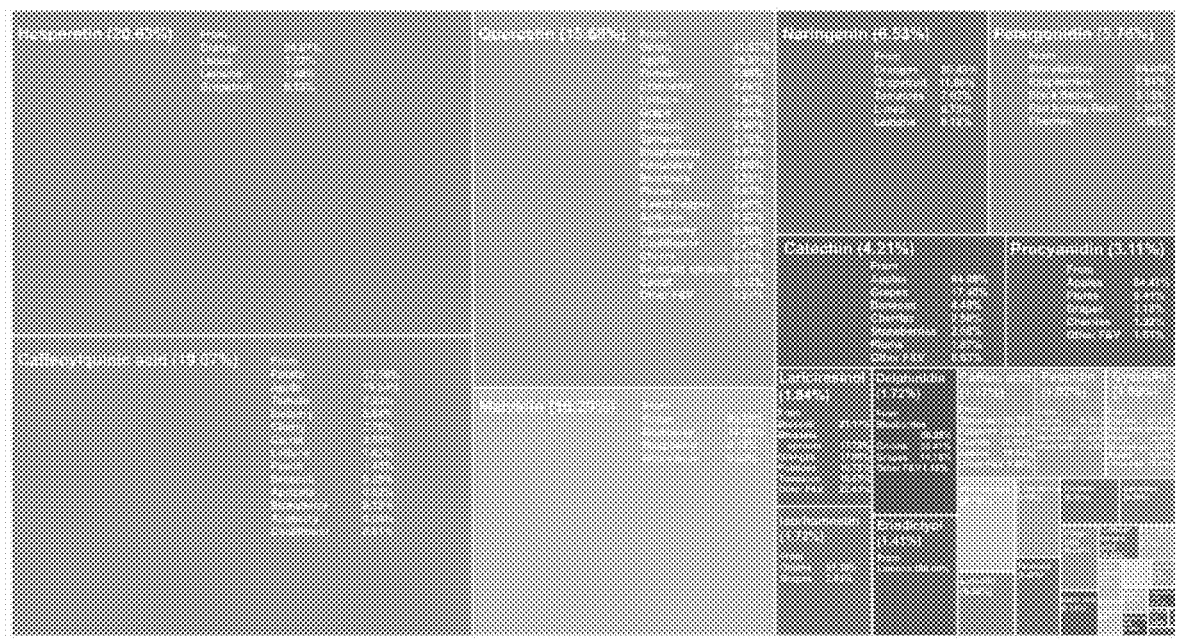
Figure 11:
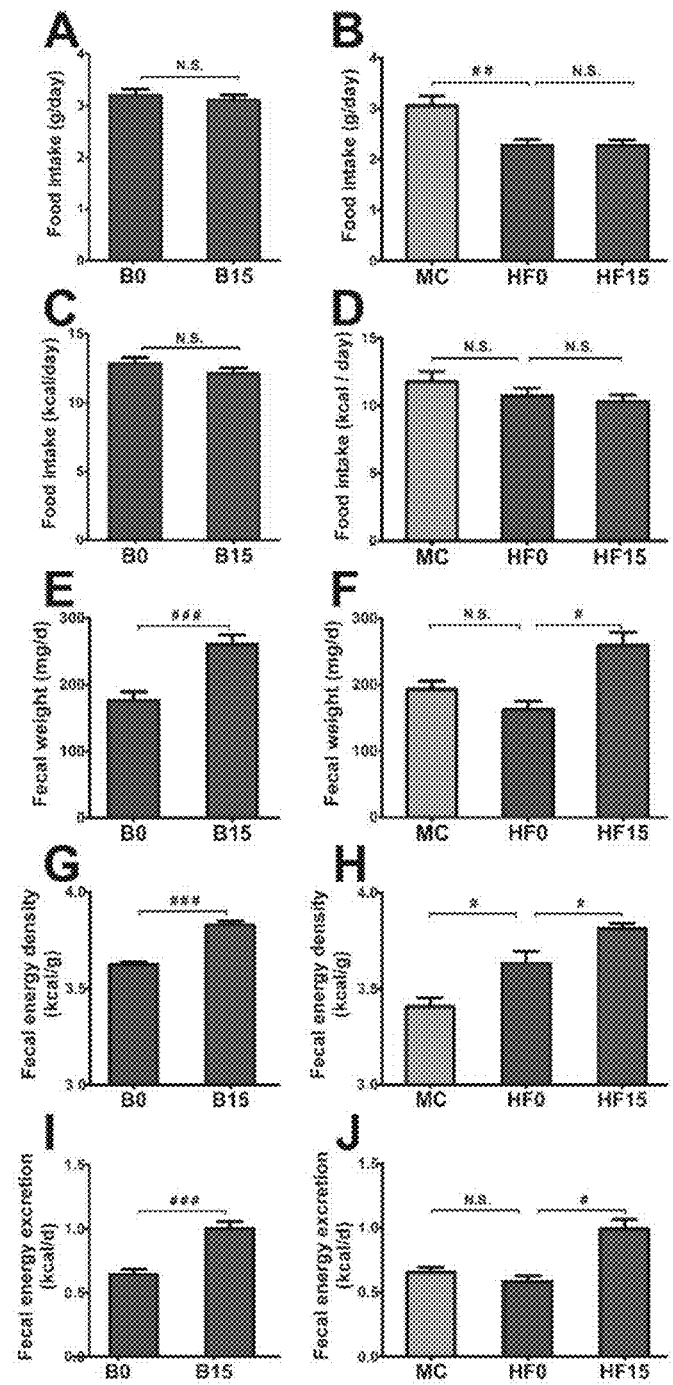
FIG. 11 shows that F&V supplementation increased fecal weight, fecal energy density, and fecal energy excretion (A-J). #P<0.05, ##P<0.01. N.S. no significant.
Figure 12:
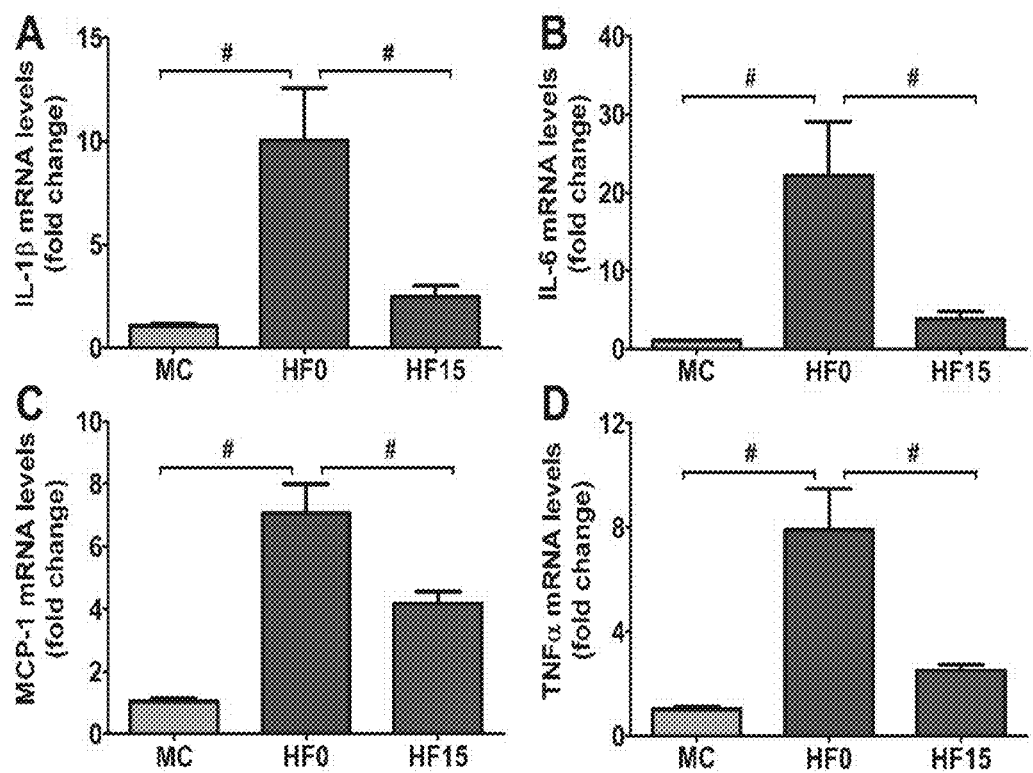
FIG. 12 shows that F&V supplementation down-regulated pro-inflammatory mRNA expression in eAT. (A-D) The levels of pro-inflammatory mRNA expression in eAT were quantitated by RTqPCR. #P<0.05. N.S. no significant. IL-1β: interleukin 1β; IL-6: IL-6: interleukin 6; MCP-1: monocyte chemoattractant protein-1; TNFα: tumor necrosis factor α.
Figure 13:
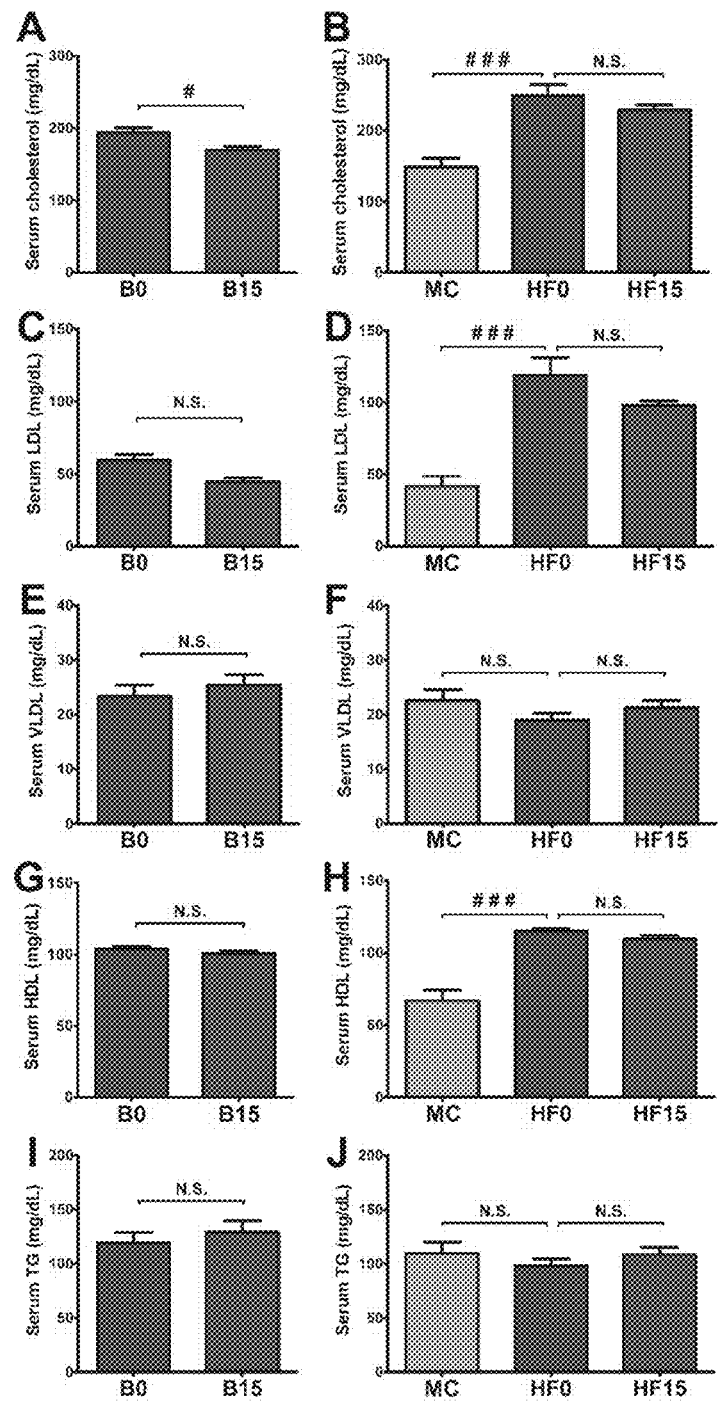
FIG. 13 shows that F&V supplementation had no significant effects on serum lipids profiling. Serum total cholesterol (A, B), LDL levels (C, D), HDL levels (E, F), VLDL levels (G, H), TG levels (I, J), serum-non-HDL and non/HDL/HDL ratio (K) are expressed as mean±SE. #P<0.05, ##P<0.01, ###P<0.001. N.S. no significant.
Figure 13:
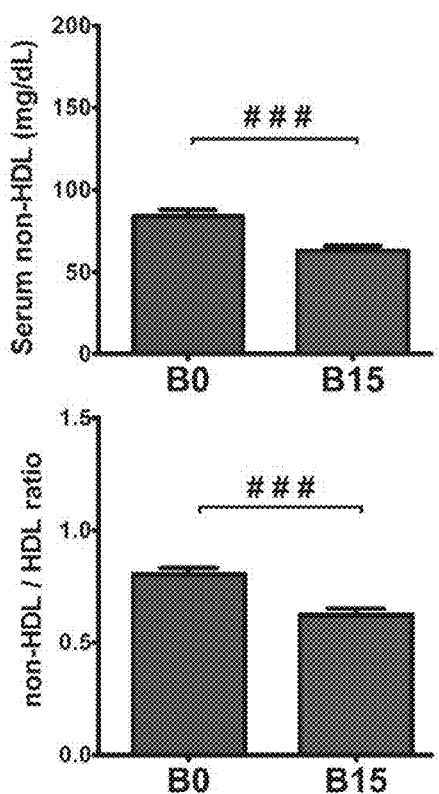
Figure 13:
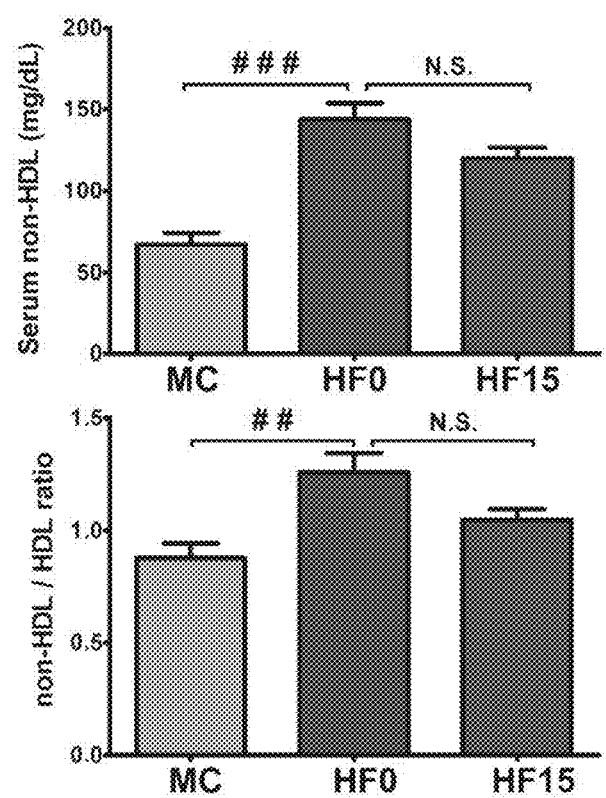

Accordingly, in some embodiments, provided herein is a formulation of F&V comprising, for example, a freeze-dried mixture of 12 fruits and 12 vegetables (e.g., as described in FIG. 10A-C) and methods of using such compositions to treat, prevent, and reduce the risk of signs, symptoms, and complications related to metabolic disorder, obesity, and related disorders.

The present disclosure is not limited to particular fruits and vegetables or components of a F&V composition. In some embodiments, the fruit species are one or more (e.g., 1, 2, 3, 4, 5, 6, 7, 8, 9, 10, 11, or all) fruit species selected from, for example, oranges, apples, bananas, grapes, watermelon, pineapple, strawberries, cantaloupe, lemons, grapefruit, peaches, or pears. In some embodiments, the vegetable species are one or more (e.g., 1, 2, 3, 4, 5, 6, 7, 8, 9, 10, 11, or all) selected from, for example, potatoes, tomatoes, sweet corn, onions, head lettuce, romaine, bell peppers, carrots, cucumbers, cabbage, beans, or sweet potato.

In some embodiments, the mixture of fruit and vegetable species comprises, consists essentially of, or consists of at least one of 16-20% oranges, 14-18% tomatoes, 8-11% apples, 13-16% potatoes, 3.0-5.5% bananas, 3-4% sweet corn, 3-4% grapes, 2-3% lettuce, 1-2% escarole, 1-2% brussels sprouts, 1-2% cabbage, 1-2% carrots, 1-3% onions, 1-2% green peas, 0.5-1.5% watermelon, 0.5-1.5% honeydew melon, 0.5-1.5% broccoli, 1-2% spinach, 0.5-1.5% peppers, 0.5-1.5% snap beans, 0.5-1.5% cantaloupe, 0.4-1.2% cauliflower, 0.5-1.0% mangoes, 0.5-1.0% papaya, 0.3-0.9% celery, 0.4-1.2% cucumbers, 0.5-1.0% pineapple, 0.25-0.75% tangerines, 0.25-0.75% limes, 0.25-0.75% strawberries, 0.25-0.75% raspberries, 0.25-0.75% grapefruit, 0.25-0.75% lemons, 0.25-0.75% cranberries, 0.3-0.5% plums, 0.3-0.5% peaches, 0.3-0.5% cherries, 0.3-0.5% blueberries, 0.3-0.5% apricots, 0.1-0.15% dried peas, 0.1-0.15% great northern beans, 0.1-0.15% dried navy beans, 0.1-0.15% dried lentils, 0.1-0.15% pinto beans, 0.1-0.15% lima beans, 0.1-0.15% red kidney beans, and 0.1-0.15% black beans (e.g., approximately 18.075% oranges, 16.161% tomatoes, 9.595% apples, 14.493% potatoes, 4.373% bananas, 3.564% sweet corn, 3.383% grapes, 2.537% lettuce, 1.651% escarole, 1.375% brussels sprouts, 1.375% cabbage, 1.329% carrots, 2.017% onions, 1.293% green peas, 1.058% watermelon, 1.058% honeydew melon, 0.84% broccoli, 1.651% spinach, 1.087% peppers, 1.061% snap beans, 1.058% cantaloupe, 0.84% cauliflower, 0.732% mangoes, 0.732% papaya, 0.626% celery, 0.814% cucumbers, 0.732% pineapple, 0.555% tangerines, 0.555% limes, 0.437% strawberries, 0.437% raspberries, 0.555% grapefruit, 0.555% lemons, 0.437% cranberries, 0.388% plums, 0.388% peaches, 0.388% cherries, 0.437% blueberries, 0.388% apricots, 0.121% dried peas, 0.121% great northern beans, 0.121% dried navy beans, 0.121% dried lentils, 0.121% pinto beans, 0.121% lima beans, 0.121% red kidney beans, and 0.121% black beans). All percentages are w/w % of the F&V mixture.

In some embodiments, composition provide at least 5 (e.g., at least 5, 6, 7, 8, 9, 10, 15 or more) of the recommended daily amounts (e.g., servings) of F&V for an average adult (See e.g., health.gov/dietaryguidelines/dga2000/document/build.htm; herein incorporated by reference in its entirety). For example, in some embodiments, a composition intended to be a single daily dose for an average adult comprises 40-65 g of dry powder (e.g., plus or minus 1, 5, 10, 15, or 20%). The amounts are adjusted for children or individuals with specific dietary need.

In some embodiments, the composition comprises a plurality of polyphenols and other beneficial molecules or compounds. For example, in some embodiments, the F&V mixture comprises a polyphenol content of 15-25% hesperetin, 15-25% caffeoylquinic acid, 10-20% quercetin, and 5-15% malvidin (e.g., 20.6% hesperetin, 19.1% caffeoylquinic acid, 15.7% quercetin, and 10.3% malvidin). In some embodiments, the composition further comprises 1-10% naringenin, 1-10% pelargonidin, 1-5% catechin, and 1-5% procyanidin (e.g., 6.5% naringenin, 5.8% pelargonidin, 4.2% catechin, and 3.1% procyanidin). All percentages are w/w % of the F&V mixture. In some embodiments, the composition further comprises one or more polyphenols selected from, for example, caffeic acid, peonidin, cyanidin, pinoresinol, p-Coumaroyl, luteolin, petunidin, daidzein, genistein, ellagic acid, or gallic acid.

In some embodiments, the composition is provided as a dry powder. In some embodiments, the powder is provided as a freeze-dried powder (e.g., prepared as described in Example 1).

The powder is used in different forms including but not limited to encapsulated, added to liquid consumables, dairy and dairy substitute products, bars, and sashes. It may also be printed using 3-D printing, to create products with different shapes and consistency.

In some embodiments, the composition is provided as a powder and the user adds the powder to a beverage or food. In some embodiments, the composition is provided as a ready to eat beverage or food product.

In some embodiments, the food or beverage product comprises 2%-20% (e.g., 5-15%, 5-20%, or 5-10%) (w/w) of the F&V composition.

In some embodiments, the beverage, nutritional supplement, or food product comprises 0-60% protein (kcal/kcal), 0-99% carbohydrates (kcal/kcal), and 0-60% fats (kcal/kcal) (e.g., 5-15% protein (kcal/kcal), 75-85% carbohydrates (kcal/kcal), and 0-20% fats (kcal/kcal); 10-12% protein (kcal/kcal), 80-83% carbohydrates (kcal/kcal), and 5-10% fat (kcal/kcal), or 11.6% protein (kcal/kcal), 81.2% carbohydrates, and 7.2% fats (kcal/kcal) (percentages of the total composition), In some embodiments, the composition is provided as a nutritional supplement or pharmaceutical formulation for oral delivery.

In some embodiments, the present disclosure provides a supplement composition comprising one or more of the foregoing compositions in combination with a pharmaceutically acceptable carrier. The actual form of the carrier, and thus, the composition itself, is not critical. The carrier may be a liquid, gel, gelcap, capsule, powder, solid tablet (coated caplet or non-coated), tea, or the like. The composition, in this case, is preferably in the form of a tablet or capsule and most preferably in the form of a soft gel capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, PA).

The dietary supplement may comprise one or more inert ingredients, especially if it is desirable to limit the number of calories added to the diet by the dietary supplement. For example, the dietary supplement may also contain optional ingredients including, for example, herbs, vitamins, minerals, enhancers, colorants, sweeteners, flavorants, inert ingredients, and the like.

In further embodiments, the compositions comprise at least one food flavoring such as acetaldehyde, acetoin (acetyl methylcarbinol), anethole (parapropenyl anisole), benzaldehyde (benzoic aldehyde), N butyric acid (butanoic acid), d or l carvone (carvol), cinnamaldehyde (cinnamic aldehyde), citral (2,6 dimethyloctadien 2,6 al 8, gera nial, neral), decanal (N decylaldehyde, capraldehyde, capric aldehyde, caprinaldehyde, aldehyde C 10), ethyl acetate, ethyl butyrate, 3 methyl 3 phenyl glycidic acid ethyl ester (ethyl methyl phenyl glycidate, strawberry aldehyde, C 16 aldehyde), ethyl vanillin, geraniol (3,7 dimethyl 2,6 and 3,6 octadien 1 ol), geranyl acetate (geraniol acetate), limonene (d, l, and dl), linalool (linalol, 3,7 dimethyl 1,6 octadien 3 ol), linalyl acetate (bergamol), methyl anthranilate (methyl 2 aminobenzoate), piperonal (3,4 methylenedioxy benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia, (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papayer somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron, tumeric, tumeric and oleoresin).

Preferred unit dosage formulations are those containing a daily dose or unit, daily subdose, as herein above-recited, or an appropriate fraction thereof, of an agent. In some embodiments, the unit dose comprises at least the recommended daily levels of fruits and vegetables for a particular subject (e.g., at least 1, 2, 3, 4, 5, 6, 7, 8, 9, 10, 15, or more times the recommended daily numbers of servings), provided in one or more doses.

The daily requirements for a particular subject vary based on age, gender, etc. (See e.g., health.gov/dietaryguidelines/dga2000/document/build.htm). For example, the number of servings of vegetable servings recommended per day varies from 3-5 and the number of servings of fruit varies from 2-4. In some embodiments, a serving is equivalent to 1 cup of raw leafy vegetables, ½ cup of other vegetables cooked or raw, ¾ cup of vegetable juice, 1 medium apple, banana, orange, pear, ½ cup of chopped, cooked, or canned fruit, or ¾ cup of fruit juice. In some embodiments, the compositions described herein are provided as a daily or unit dose of 20-80 (e.g., 30-70, 30-60, or 40-65 g/day) of a F&V mixture (e.g., 8-9 servings of F&V). The amount is adjusted based on the dietary needs of the particular subject.

It also is intended that the compositions and methods of this disclosure be combined with other suitable compositions and therapies. For example, the compositions described herein may co-administered with one or more additional agents suitable for the treating and preventing metabolic disorders and other complications of obesity.

The F&V compositions described herein find use in the treating, prevention, and reduction of risk of a number of different conditions associated with obesity and metabolic disorders. Examples include, but are not limited to, weight gain, obesity, inflammatory conditions, fatty liver disease, high cholesterol, glucose intolerance, insulin resistance, low gut microbiota diversity, heart disease, and atherosclerosis. In some embodiments, the compositions find use in decreasing fat mass, increasing muscle mass, reducing inflammatory cytokines and/or ceramides, reducing tissue inflammation, decreasing cholesterol, improving glucose tolerance, improving immune response, increasing gut microbiota diversity, increasing lifespan, improving cognition, and/or improving bone health in a subject.

In some embodiments, the F&V compositions described herein are administered to a subject diagnosed with or at risk of a disorder or condition described herein or otherwise in need. In some embodiments, the subject is obese or not obese. In some embodiments, the subject has one or more risk factors for a disease or condition described herein (e.g., family history, excess weight, etc.). In some embodiments, the subject does not consume the recommended daily levels of F&V on a regular basis.

In some embodiments, the administering reduces a measure (e.g., sign, symptom, lab result) or a disorder, condition, or complication described herein. In some embodiments, the administering prevent or reduces the risk of developing such signs, symptoms, or lab results in an individual that does not exhibit the signs or symptoms.

In some embodiments, the administering is repeated one or more (e.g., 1, 2, 3, or more) times per day for a period of at least 1 week (e.g., at least 1 month, at least one year, multiple years, or indefinitely).

EXPERIMENTAL

Example 1

A Mixture of Fruits & Vegetables Prevents Diet-Induced Hepatic Steatosis in Mice Methods Animals and Diets Diet compositions are shown in Tables 1-5. Four-week-old C57BL/6J male mice were purchased from The Jackson Laboratory (Bar Harbor, ME, USA) and housed at the animal care facility at Jean Mayer USDA Human Nutrition Research Center on Aging at Tufts University. After 12 days of acclimation, individually caged animals were assigned into weight-matched 9 groups, including standard mice diet [Basal (B0), 16 kcal % fat, AIN-93G; Research Diets, #D10012G), high-fat diet (HF0, 45 kcal % fat, Research Diets, #D12451M), low-fat match control for HF diet (MC, 10.0 kcal % fat, Research Diets, #D12450H), and B0 and HF0 supplemented with 5%, 10%, and 15% of a fruit and vegetable (F&V) mixture (see below, respectively. The nutrient content of animal diet with or without F&V powder is presented in Table 3. Mice were fed ad libitum with respective diets for 20-weeks, during and at which time different outcome variables, including body weight, food intake, and body composition were recorded and analyzed.

Freeze-Dried Fruits and Vegetables (F&V) Powder Preparation

F&V mixture containing a combination of 24 of the most commonly consumed F&V based on USDA census data was homogenized to prepare the freeze dried powder (See Tables 10A-B for F&V compositions). To mimic the American patterns of consumption, the proportion of each individual fruit or vegetable in the F&V mixture was calculated based on the relative proportion of yearly F&V consumption in United States. The fresh fruits and vegetables were purchased from grocery stores, and then washed and cut to get only edible part. Next, they were blended in 30000 rpm blender, 15 to 20 second each time, total 2 minutes, to prepare a fruit and vegetable homogenate. The F&V homogenate was saved in stainless steel container, wrapped with aluminum foil and frozen in −80° C. freezer overnight. Then, the frozen F&V mixture was put into a freeze-dryer chamber (VirTis Freezemobile 35XL Freeze Dryer) with vacuum set to 300 mTorr and shelf temperature of the freeze-dryer to −20° C. Next, shelf temperature was increased by 10° C. each hour. The maximal shelf temperature is 20° C. The F&V mixture was completely dried in 4 days. The dried mixture was pulverized with the same blender with the same setting to obtain a fine powder and was stored in plastic bags at −80° C. freezer until it was use for animal diet preparation.

F&V powder was incorporated into experimental diets on a w/w basis, replacing 0, 5, 10 or 15% of the diet. Nutritional information about the diets are shown in Tables 2-5 as follows: calculated polyphenols content in F&V powder (Table 2), nutrient content of animal diet with or without F&V powder (Table 3), polyphenol and total antioxidant content of animal diet with or without F&V powder (Table 4), and fiber content including total fiber and soluble and insoluble fiber of animal diet with or without F&V powder (Table 5).

Male C57BL/6J mice were assigned into one of 9 diet groups (12 mice/group). Diets were fed ad libitum for 20 weeks; mice were weighed weekly and food intake was recorded.

At 15 weeks, total body fat and lean mass were measured by MM.

Mouse fecal sample was collected at 18 weeks and stored in −80° C. freezer for measurement of energy content by bomb calorimeter and microbiota analysis.

After 20 weeks, mice were euthanized. Blood sample was collected. Serum were isolated and stored in −80° C. for further analysis. Liver and adipose tissue were partially fixed in formalin and partially first frozen in liquid nitrogen and then transferred to −80° C. for storage. Fixed liver and adipose tissue were processed for histopathology to measure lipid accumulation & inflammation, respectively.

Frozen adipose tissue samples were used to analyze mRNA levels of pro-inflammatory molecules by RTqPCR.

Body Composition Analysis

Body composition (% fat tissue and % lean tissue) was assessed by using rodent magnetic resonance imaging system (Whole Body Composition Analyzer, EchoMRI, Houston, TX) at 15 week of age.

Fecal Energy Density Assay

Fecal energy density was determined using a PARR 6200 Isoperibol calorimeter (Parr Instrument Company, Moline, IL, USA) following the manufacturer's instruction.

Adipose Tissue Histology and Adipocyte Size Determination

Epididymal adipose tissue were dissected, fixed, embedded in paraffin, and sectioned. The sections were stained with hematoxylin and eosin (H&E). Adipocyte size of H&E stained epididymal adipose tissue sections were measured based on previously reported method (Parlee et al., 2014). Briefly, the digital images of H&E-stained epididymal adipose tissues were acquired with an Olympus FSX100 light microscope and the area ($\mu m^2$) of each adipocyte were manually determined with touch-screen laptop computer. Data were expressed as the frequency of adipocytes compared to the total number of adipocytes counted (% total).

Liver Tissue Histology and Hepatic Steatosis Area Measurement

Liver tissue were dissected, fixed, embedded in paraffin, and sectioned. The sections were stained with hematoxylin and eosin (H&E), which was performed in Animal Histology and Pathology Services at Tufts University and Tufts Medical Center for histology analysis. The digital images of H&E-stained liver tissues were acquired with an Olympus FSX100 light microscope. Hepatic steatosis area was measured using ImageJ software as previous reported (McLaughlin et al., 2010).

Serum, Liver and Adipose Tissue Lipidomic Profile

Serum, liver and adipose tissue lipidomic profile was analyzed using LC-MS/MS techniques by VCU Massey Cancer Center Lipidomics Shared Resource.

Liver nSMase Activity Assay

Liver homogenates were prepared and liver nSMase activity was measured based on reported methods (Empinado et al., 2014). Briefly, nSMase activities were measured in liver homogenates, and 40 µg were used in each assay. The protein concentration was assessed using a Thermo Scientific Pierce BCA Protein Assay kit following the microplate procedure. The nSMase activity assay was done in a 50 mM Tris-HCl (pH 7.4) reaction buffer containing 7.5 mM $MgCl_2$, 10 µM C6-NBD-SM, 1 mM sodium ortovanadate, 15 mM sodium fluoride, protease inhibitor cocktail and 40 µg of homogenate in a final volume of 40 µl for 30 min. The reactions were stopped by the addition of 0.5 ml methanol. After further incubation at 37° C. for 30 min, the samples were centrifuged at 1,000×g, and the clear supernatant was transferred to clear HPLC vials. The generated fluorescent product, NBD-ceramide, was monitored by a reverse phase HPLC.

Gene-Expression Analyses

Total RNA was extracted from liver and adipose tissue using TRIzol reagent (Invitrogen). Complementary DNA (cDNA) was generated by reverse-transcription of 1 µg total RNA using Super Script III First-Strand Synthesis System (Invitrogen). Gene expression levels of interest were quantitated by using SYBR Green reagent. Results are represented as a fold change in comparative expression level.

Measurement of Serum Pro-Inflammatory Cytokine Levels and Serum Lipids Profiling Mouse serum pro-inflammatory cytokine levels were determined using electrochemiluminescent multiplex assays and serum lipids profiling was performed by Nutritional Evaluation Laboratory at HNRCA.

16S rDNA Microbiota Profiling

DNA Extraction and 16S rDNA Amplicon Generation

Bacterial genomic DNA was extracted using the QIAamp Stool DNA Kit (Qiagen, Germantown, MD) with the following modifications. Samples were resuspended in ASL buffer (Qiagen kit) in the presence of 500 mg of 0.1 mm silica/zirconium beads (BioSpec Products, Bartlesville, OK) and incubated at 95° C. for 10 min. After cooling to room temperature, the samples were placed on a bead-beater at 4° C. for 5 minutes. The stool solids were pelleted on a microfuge and the supernatant was treated with an Inhibitex tablet, after which the standard Qiagen protocol was followed. Amplicons of the V4 region of the bacterial 16S ribosomal DNA were generated by PCR, and amplicon pools were sequenced on a MiSeq sequencer (Illumina), and QIIME analysis were performed and an OTU table was generated by the Tufts University Core Facility Genomics Core. Shannon and Simpson diversity index were determined, and unweighted UniFrac analysis was conducted. Data were analyzed using Bioconductor Workflow. Kruskal-Wallis test was performed for each diversity metric, followed by a Wilcoxon Rank Sum test for pairwise comparisons with false discovery rate (FDR) correction (Callahan et al., 2016; Goodrich et al., 2014; Lozupone and Knight, 2008).

Microbiota Data Analysis

For analyzing microbiome data, a pipeline called Qiime (specifically QIIME 1.8.0) was used. The basics of this pipeline are as follows: All the demultiplexed fastq files are combined into one file which includes joining the paired end reads and concatenating all the files together (qiime.org/scripts/join_paired_ends.html) Barcodes are extracted from each read. (qiime.org/scripts/extract barcodes.html) The libraries are split which generates a file where each sequence is identified with a corresponding identifier from the mapping file. (qiime.org/scripts/split_libraries.html) From there, OTU picking is performed using a closed reference, which generates the OTU table. It also gives a table with the sequence counts per sample which is used when deciding the sampling depth in the alpha analysis. (qiime.org/scripts/pick_closed_reference_otus.html). The reference OTUs come from a database called greengenes and the most recent release which is greengenes_13_8 (greengenes.secondgenome.com/downloads) was used. Also, a 0.99 similarity was used when picking the OTUs.

Quantification and Statistical Analysis

Data are presented as mean±SE. A two-tailed unpaired t-test or two-tailed unpaired t-test with Welch's correction was used for comparison between B0 and B15 with equal or unequal variance, respectively. The differences among MC, HF0 and HF15 data were analyzed by one way ANOVA followed by Dunnett's post-hoc test. Correlation coefficients were calculated by using a nonparametric Spearman's rank correlation; and p values from Spearman correlation analysis of gut bacterial abundance and clinical biomarkers were corrected for false detection rate using the Benjamin-Hochberg method. Differential abundance of gut bacteria between groups was analyzed using Deseq2 package. Significance was set at p<0.05.

TABLE 1

Correlations between sphingolipids and TNFα and hepatic steatosis area

| Factors | Basal diet | | High fat diet | |
|---|---|---|---|---|
| | R value | P value | R value | P value |
| Hepatic steatosis area × Total serum ceramides | 0.755 | 0.005 | 0.762 | 0.004 |
| Hepatic steatosis area × TNF-α | 0.762 | 0.004 | 0.529 | 0.024 |
| Hepatic steatosis area × serum C16:0 ceramide | 0.473 | 0.142 | 0.657 | 0.020 |
| TNF-α × serum C16:0 ceramide | 0.254 | 0.242 | 0.409 | 0.047 |
| Hepatic steatosis area × serum C20:0 ceramide | 0.669 | 0.035 | 0.531 | 0.075 |
| Hepatic steatosis area × serum C22:0 ceramide | 0.748 | 0.005 | 0.392 | 0.208 |
| Hepatic steatosis area × serum C24:0 ceramide | 0.664 | 0.018 | 0.469 | 0.124 |
| Hepatic steatosis area × serum C24:1 ceramide | 0.399 | 0.199 | 0.720 | 0.008 |
| TNF-α × serum C24:1 ceramide | 0.239 | 0.261 | 0.516 | 0.010 |

Correlation Analysis was Conducted Using Spearman's Correlation Test

TABLE 2

Calculated polyphenols content in F & V powder

| F &V polyphenol content | μg/g | % |
|---|---|---|
| Flavanones | 463.0 | 25.64% |
| Hydroxycinnamic acids | 419.5 | 23.23% |
| Anthocyanins | 322.8 | 17.88% |
| Flavonols | 230.2 | 12.75% |
| Isoflavonoids | 184.8 | 10.23% |
| Flavanols | 118.5 | 6.56% |
| Lignans | 42.8 | 2.37% |
| Hydroxybenzoic acids | 13.8 | 0.77% |
| Flavones | 7.7 | 0.43% |
| Stilbenes | 1.5 | 0.08% |
| Other | 1.2 | 0.07% |
| Total | 1805.7 | 100.0% |

The polyphenols content in F&V powder is calculated based on USDA database at www.ars.usda.gov/nutrientdata

TABLE 3

Nutrient content of animal diet with or without F & V powder

| Diet Group* | F & V Content (%, w/w) | Protein (kcal %) | Carb (kcal %) | Fat (kcal %) | Energy Density (kcal/g) |
|---|---|---|---|---|---|
| B0 | 0 | 20.3 | 64 | 15.8 | 4.00 |
| B5 | 5 | 19.9 | 64.8 | 15.3 | 3.97 |
| B10 | 10 | 19.4 | 65.7 | 14.9 | 3.94 |
| B15 | 15 | 19 | 66.5 | 14.5 | 3.91 |
| MC | 0 | 20.0 | 70.0 | 10.0 | 3.85 |
| HF0 | 0 | 20.0 | 35.0 | 45.0 | 4.73 |
| HF5 | 5 | 19.6 | 37.3 | 43.1 | 4.66 |
| HF10 | 10 | 19.2 | 39.6 | 41.2 | 4.59 |
| HF15 | 15 | 18.7 | 41.9 | 39.3 | 4.53 |

*B0 (basal diet); B5 (basal diet + 5% F & V); B10 (basal diet + 10% F & V); B15 (basal diet + 15% F & V); MC (low fat diet); HF0 (high fat diet + 0% F & V); HF5 (high fat diet + 5% F & V); HF10 (high fat diet + 10% F & V); HF15 (high fat diet + 15% F & V)

TABLE 4

Polyphenol and total antioxidant content of animal diet with or without F & V powder [1]

| Diet Group* | Total polyphenols [2] (μg/g) | Total antioxidant nutrients [3] (μg/g) | Total antioxidant nutrients [3] (μg/kcal) |
|---|---|---|---|
| B0 | 0 | 105.2 | 26.3 |
| B5 | 114 | 196.1 | 53.4 |
| B10 | 227 | 287.1 | 80.4 |
| B15 | 341 | 378.0 | 107.5 |
| MC | 0 | 75.2 | 19.6 |
| HF0 | 0 | 92.4 | 19.6 |
| HF5 | 114 | 184.0 | 46.9 |
| HF10 | 227 | 275.5 | 74.3 |
| HF15 | 341 | 367.1 | 101.7 |

[1] The F & V powder contains total polyphenols 2271 μg/g and total antioxidant nutrients 1923.5 μg/g.
[2] The F & V powder contains 121 polyphenolic compounds. The top 10, i.e. hesperetin, caffeoylquinic acid, quercetin, malvidin, genistin, daidzin, naringenin, pelargonidin, cyanidin, and lariciresinol, constitute 84.9% of total polyphenols.
[3] Total antioxidant nutrients include vitamin C, E, Se, and Zinc.
*B0 (basal diet); B5 (basal diet + 5% F & V); B10 (basal diet + 10% F & V); B15 (basal diet + 15% F & V); MC (low fat diet); HF0 (high fat diet + 0% F & V); HF5 (high fat diet + 5% F & V); HF10 (high fat diet + 10% F & V); HF15 (high fat diet + 15% F & V)
The content of polyphenols and antioxidant nutrients in F & V powder is calculated based on USDA database at http://www.ars.usda.gov/nutrientdata

TABLE 5

Fiber content of animal diet with or without F&V powder

| Diet Group* | Total fiber (µg/g) | Total fiber (µg/kcal) | Soluble fiber (µg/g) | Soluble fiber (µg/kcal) | Insoluble fiber (µg/g) | Insoluble fiber (µg/kcal) |
|---|---|---|---|---|---|---|
| B0 | 50.0 | 12.5 | 0.0 | 0.0 | 50.0 | 12.5 |
| B5 | 49.0 | 12.3 | 0.3 | 0.1 | 48.7 | 12.2 |
| B10 | 48.0 | 12.1 | 0.7 | 0.2 | 47.4 | 11.9 |
| B15 | 47.1 | 12.0 | 1.0 | 0.3 | 46.1 | 11.7 |
| MC | 47.4 | 12.3 | 0.0 | 0.0 | 47.4 | 12.3 |
| HF0 | 58.3 | 12.3 | 0.0 | 0.0 | 58.3 | 12.3 |
| HF5 | 56.9 | 12.2 | 0.3 | 0.1 | 56.5 | 12.1 |
| HF10 | 55.5 | 12.0 | 0.7 | 0.2 | 54.8 | 11.8 |
| HF15 | 54.1 | 11.8 | 1.0 | 0.3 | 53.1 | 11.5 |
| F&V | 30.2 | 8.9 | 6.5 | 1.9 | 23.7 | 7.0 |

*B0 (basal diet); B5 (basal diet + 5% F&V); B10 (basal diet + 10% F&V); B15 (basal diet + 15% F&V); MC (low fat diet); HF0 (high fat diet + 0% F&V); HF5 (high fat diet + 5% F&V); HF10 (high fat diet + 10% F&V); HF15 (high fat diet + 15% F&V)

Results

F&V Supplementation Reduced Weight Gain in Obese Mice Fed the HF Diet, but had No Effect on Weight Gain in Lean Mice Fed the Basal Diet To investigate the effects of F&V on obesity and metabolic diseases, a unique F&V mixture containing 24 of the most commonly consumed F&V based on USDA census data (average per capita daily consumption (grams) from 1994 to 2008) was formulated. To mimic the natural patterns of consumption, the proportion of each individual fruit or vegetable in the F&V mixture was calculated based on the relative proportion of yearly F&V consumption in the United States. A blend of 12 fruits and 12 vegetables was freeze-dried, pulverized, and incorporated into experimental diets on a w/w basis, replacing 0, 5, 10 or 15% of the diet.

Next, the effects of the F&V supplementation in lean mice fed standard diet (Basal, B; AIN-93, 16 kcal % fat) or obese mice was calculated. Obesity was induced by feeding HF diet (45 kcal % fat, which is typically used in studies to induce obesity in mice). Because there are slight differences between the AIN-93 and the HF diet used, an additional group of mice were fed a micronutrient matched control diet (MC; 10 kcal % fat), as a control for the high fat diet (Warden and Fisler, 2008). Mice were fed their respective diets for 20 weeks.

Obese mice fed HF diet alone (HF0) gained 77.1% more weight over the 20 weeks than those fed the MC diet; however, mice fed the HF diet supplemented with 15% F&V (HF15) gained significantly less body weight compared to mice fed HF diet without F&V (HF0) (FIG. 1B). No significant differences were observed on weight gain in mice fed the HF diet with the lower (5% and 10%) levels of F&V supplementation (FIG. 1B), indicating that 15% F&V is the most efficacious amount in reducing body weight gain in diet-induced obesity. Similar observation was made on other outcomes of interest. Accordingly, data from 15% supplemented diets is used. Further, body composition (measured using MiI at 17 weeks of age) showed that, compared to mice fed the MC diet, those fed the HF diet had 107% more fat tissue weight (FIG. 1D) and 58.3% more total fat mass as a percentage of body weight (FIG. 1F). The percentage of lean tissue mass in mice fed the HF diet (HF0) was 18.5% lower than that of the mice fed the MC diet (FIG. 1H). Mice fed the 15% F&V supplemented HF diet had significantly less fat tissue weight (FIG. 1D) compared to those fed the HF diet alone (HF0).

Mice fed the basal diet alone (B0) had lower weight gain than those fed HF0 diet (FIGS. 1A&B). There was no significant effect of F&V supplementation on weight gain (FIG. 1A) and body composition (FIGS. 1C, 1E, 1G, and 1I) in mice fed the Basal diet.

There was no significant impact of F&V on the level of food energy intake (FIG. S1D) in obese mice. F&V supplementation in both basal and HF diets significantly increased fecal weight (FIGS. S1E and S1F), fecal energy density (FIGS. S1G and S1H), and fecal energy excretion (FIGS. S1I and S1J), indicating that beneficial effects of F&V on reducing weight gain in mice fed HF diet may be mediated through decreasing energy harvesting.

Dietary F&V Supplementation Reduced Adipose Tissue Inflammation and Prevented NAFLD Independent of Food Intake and Body Weight Reduction Dysfunctional adipose tissue, especially visceral white adipose tissue, characterized by adipocyte death and infiltrated macrophages and other inflammatory cells, is linked to pathogenesis of metabolic diseases (Paniagua, 2016; van Greevenbroek et al., 2016). Crown-like structures, known to be formed by accumulated inflammatory immune cells around dying adipocytes, in gonadal adipose tissue, have been associated with the development of metabolic disorders (van Beek et al., 2015). Immune cell filtration is a prominent feature of adipose tissue dysfunction (Guzik et al., 2017).

Figure 2:
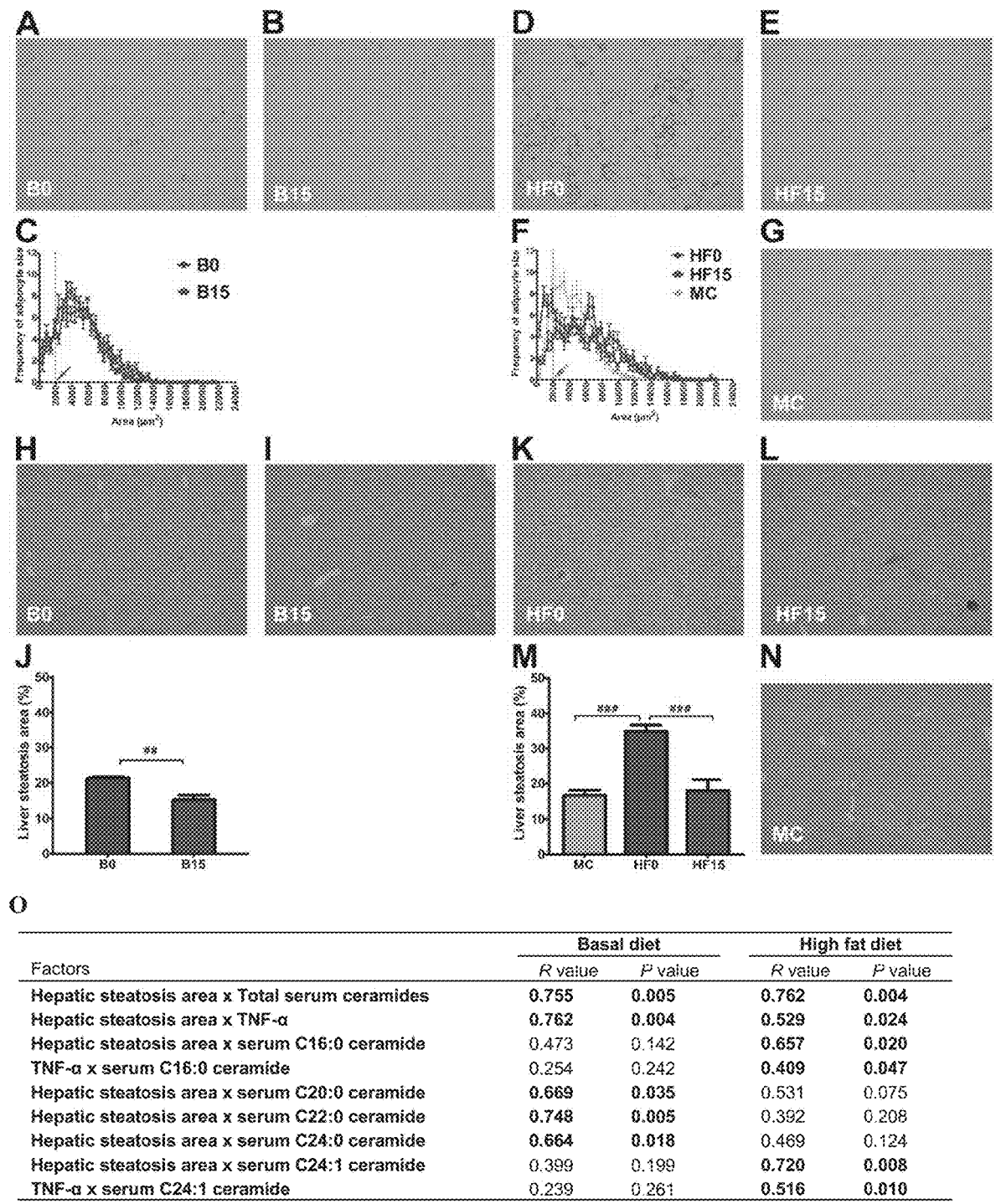
FIG. 2 shows that F&V supplementation suppressed inflammatory cell infiltration in adipose tissue and prevented NAFLD. Representative images of eAT sections stained with H&E (A, B, D, E, and G) are shown. Adipocyte size distribution of eAT in the mice fed basal diet with 0% or 15% F&V (2C) and high fat diet with 0% or 15% F&V as well as matched control diet (2F) are shown. The pictures (H-I, K-L, and N) are representative images of H/E stained liver tissue sections. Hepatic steatosis area is expressed as mean±SE. (O) Table of hepatic steatosis correlation with serum ceramides and TNFα. #$P<0.05$, ##$P<0.01$, ###$P<0.001$. N.S. not significant.

To explore whether increasing F&V consumption prevents adipose tissue inflammation, histological analysis of epididymal adipose tissue (eAT) in mice fed Basal or HF diets supplemented with or without F&V was performed. Crown like structures were found in mice fed either the HF0 diet or B0 diets, albeit at much lower densities in the B0 compared to HF0 (FIGS. 2A and 2D). Feeding mice the HF or basal diets supplemented with 15% F&V eliminated the crown-like structures (FIGS. 2B and 2E). These data indicate that the anti-inflammatory effect of F&V in eAT is independent of its anti-obesity effect due to the fact that there was no difference in average body weight between mice fed a basal diet without and with 15% F&V (FIGS. 1A and 1B). Similar to previous reports (Strissel et al., 2007), a prevalence of small adipocytes (<2000 µm²) was observed in mice fed a HF diet at 20 weeks (FIG. 2F). Increased prevalence of small adipocytes is a feature of dead adipocytes in remodeled eAT and is often associated with NAFLD due to reduced fat storage capacity of the adipose tissue. Adding 15% F&V to HF diet remarkably reduced the prevalence of small adipocytes induced by HF diet (FIG. 2F). There was no significant effect of F&V on the eAT adipocyte size in the mice fed the Basal diet (FIG. 2C).

Pro-inflammatory cytokine gene expression levels were examined in the mice eAT and it was found that the mRNA levels of pro-inflammatory cytokines, TNFα, IL-1β, IL-6, and MCP-1, were higher in eAT of the mice fed HF diet alone compared to those fed MC diet. Compared to HFD alone, mice fed HFD with 15% F&V had significantly less pro-inflammatory cytokine mRNA expression in eAT (FIG. S2A-S2D). No significant difference in the pro-inflammatory cytokine mRNA levels between mice fed B0 and B15 diets was observed.

Figure 3:
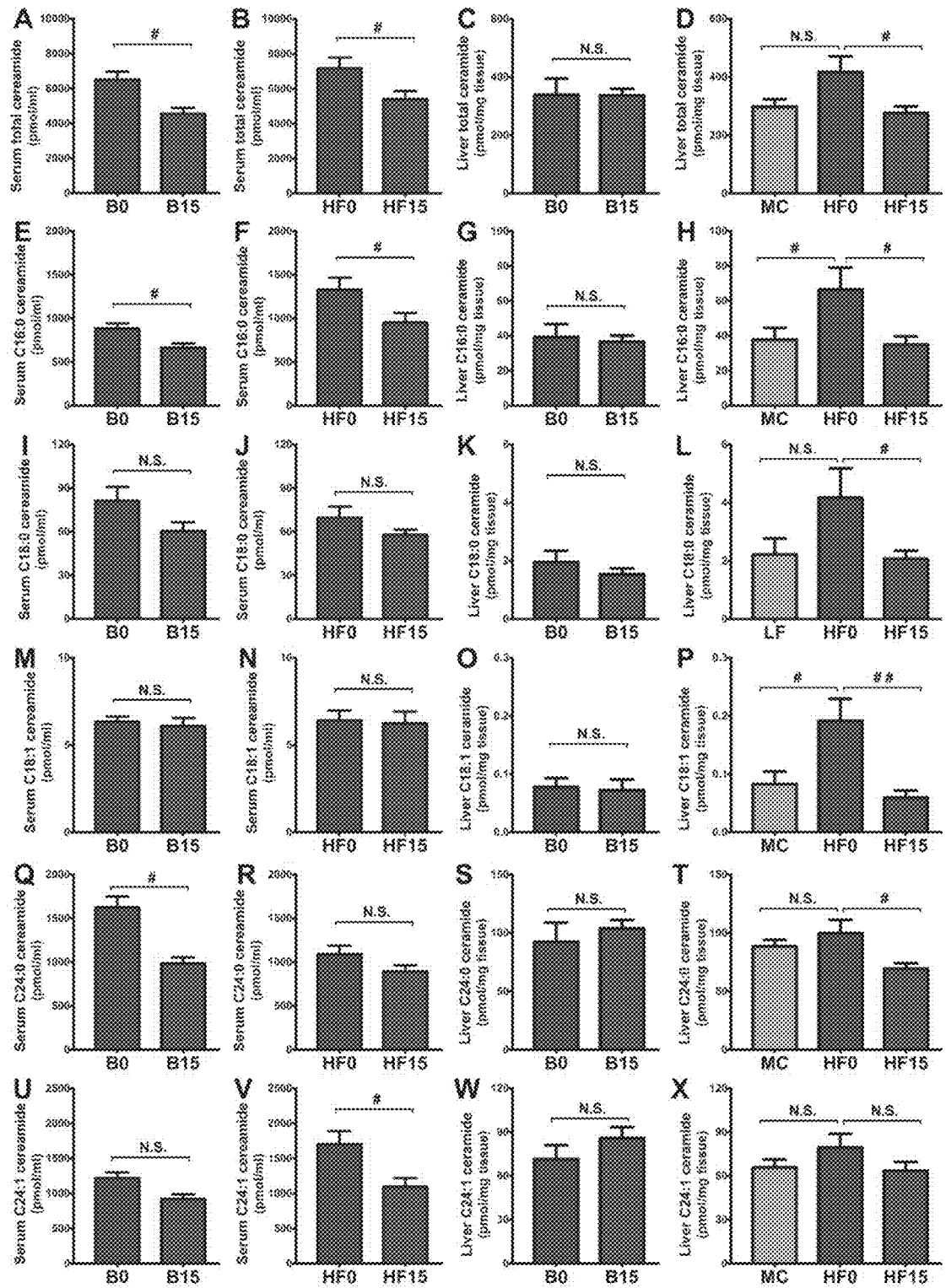
FIG. 3 shows that F&V supplementation reduces serum and liver ceramide levels. (A-X) Serum and liver levels of total ceramides and indicated ceramide species were determined. #P<0.05, ##P<0.01, N.S. not significant.

H&E histological staining of liver sections showed no sign of NAFLD in mice fed the MC diet (10 kcal % fat) (FIG. 3A). Mice fed either the Basal diet (B0, AIN-93 with 16 kcal % fat) or HF diet (HF0, 45 kcal % fat) for 20 weeks developed mild and severe NAFLD, respectively (FIGS. 2H and 2K). In comparison, mice receiving 15% F&V in both the basal and HF diets showed significantly less hepatic steatosis ($p<0.05$, FIGS. 2I, 2J, 2L, and 2M). These data indicate that the anti-hepatosteatosis effect of F&V is independent of its anti-obesity effect due to the fact that there was no difference in average body weight between mice fed a basal diet without and with 15% F&V (FIGS. 1A and 1B).

As dyslipidemia is strongly associated with NAFLD (Chatrath et al., 2012; Katsiki et al., 2016; Zhang and Lu, 2015), serum lipid profiling was performed. Results show that F&V supplementation had no significant effect on serum lipids profiles (FIG. 13A-13J). Thus, the effect of F&V in this model on liver steatosis is not mediated through changes in lipid profile.

Figure 8:
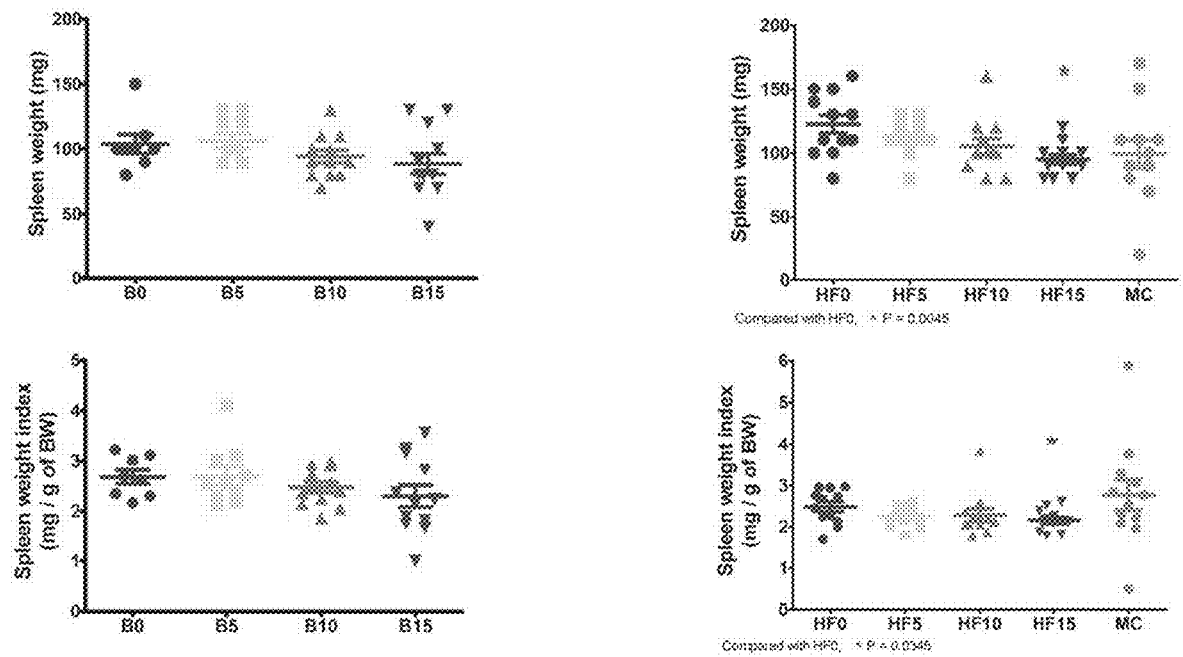
FIG. 8 shows that mice fed HFD+15% F&V had lower spleen weight and spleen weight index.

Compared to mice fed HFD alone, mice fed HFD+F&V had lower spleen weight and spleen weight index, which was calculated as mg spleen/g body weight (FIG. 8).

F&V Supplementation Reduced Circulating and Liver Tissue Ceramides as Well as Pro-Inflammatory Cytokine TNFα

As levels of circulating sphingolipids, especially ceramides, are closely associated with NAFLD pathogenesis (Ilan, 2016; Nikolova-Karakashian, 2018; Regnier et al., 2018), serum sphingolipid profile analysis was performed. The results show that the mice fed the B15 (FIG. 3A) or HF15 diets (FIG. 3B) had significantly lower serum levels of total ceramides compared to B0 or HF0, respectively.

Similarly, serum levels of other ceramide species, such as C16:0 ceramide, C24:0 ceramide, and C24:1 ceramide, in the mice fed B15 or HF15 diets were significantly lower or trended to be lower compared to B0 or HF0, respectively (FIG. 3E-3F, 3Q-3R, 3U-3V). No significant differences of the levels of serum C18:1 ceramide and C18:1 ceramide were found in the mice fed B0 diet compared to that of B15 diet or the mice fed HF diet compared to that of HF15 diet (FIGS. 3I-3J and 3M-3N). Spearman correlation analysis indicated that NAFLD in mice fed either the Basal or HF diets is positively correlated with total serum ceramides and TNFα, respectively (Table 1). Serum long chain ceramide species including C16:0, C20:0, C22:0, C24:0, and C24:1 ceramides are also positively correlated with NAFLD in mice fed either the basal or HF diets (Table 1). These results indicate that the effects of F&V on NAFLD may be mediated through changes in ceramide levels.

Levels of liver ceramides were measured. It was found that mice fed the HF0 had higher levels of liver total ceramide and other ceramide species compared to mice fed the MC diet. HF diet-induced higher ceramide levels were attenuated by adding 15% F&V to the HF diet (FIG. 3D, 3H, 3L, 3P, 3T, 3X). No significant impact of F&V on liver ceramide levels in mice fed the Basal diet (FIG. 3C, 3G, 3K, 3O, 3S, 3W) was observed, indicated that there are differences between impact of F&V on systemic and tissue levels of ceramides.

Figure 4:
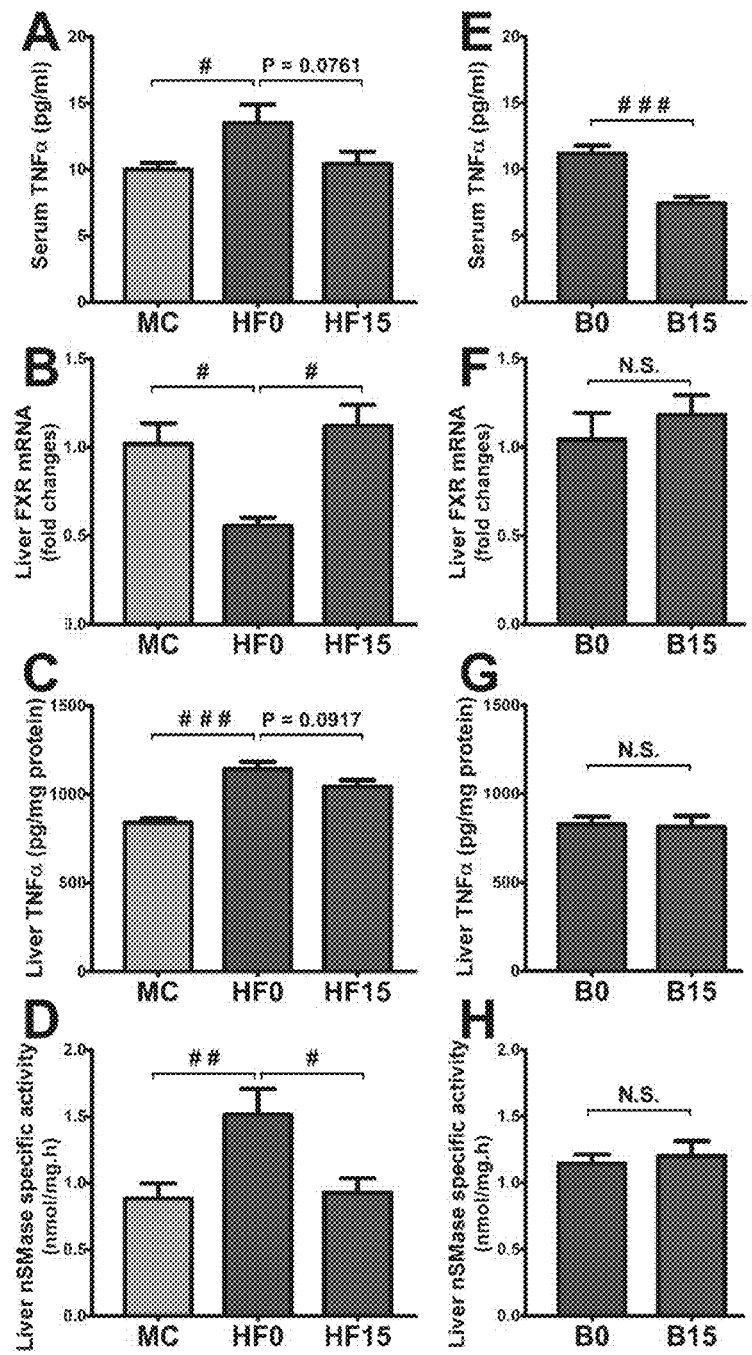
FIG. 4 shows effects of F&V supplementation on the levels of liver FXR expression, nSMase activity, and levels of systemic and liver TNFα. The levels of serum and liver pro-inflammatory cytokine TNFα (4A, 4E, 4C, and 4G) were measured by ELISA. The mRNA levels of liver FXR (4B and 4F) were quantitated by RTqPCR. Hepatic nSMase activity (4D-4H) were determined using C6-NBD-SM as a substrate, and generated fluorescent product, NBD-ceramide, was monitored by a reverse phase HPLC.
Figure 14:
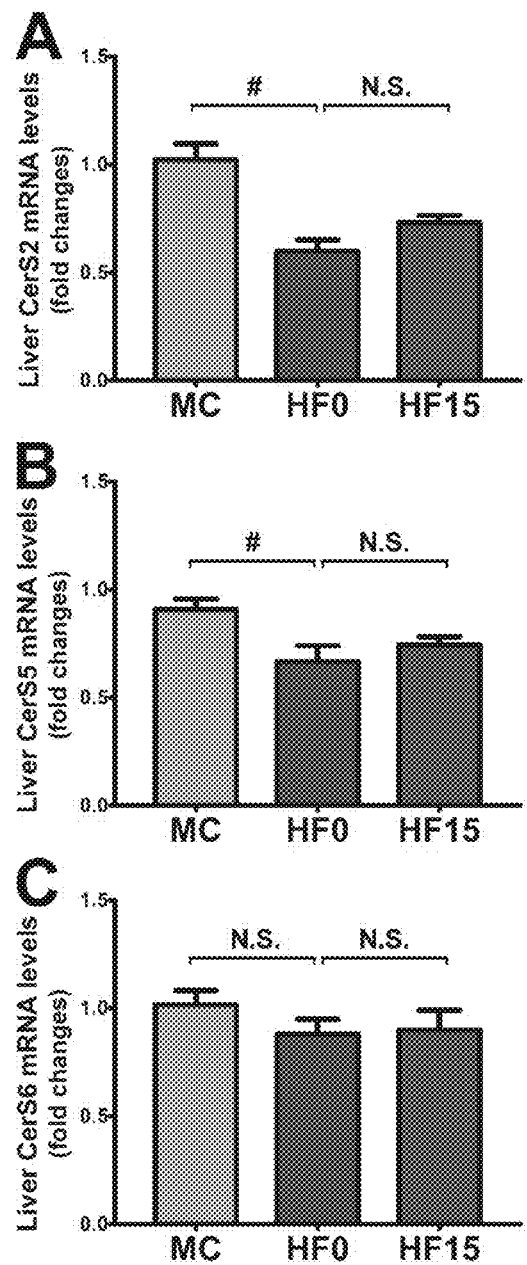
FIG. 14 shows that F&V supplementation did not significant affect liver ceramide synthases mRNA expression. (A-C) The mRNA levels of liver ceramide synthases were quantitated by RTqPCR. #P<0.05, N.S. not significant.

To determine the mechanism of F&V-induced reduction in liver ceramides, its effects on mRNA levels of liver ceramide synthase (CerS), the enzyme required for ceramide generation from either de novo synthesis pathway or salvage pathway were assayed. CerS mRNA levels of the mice fed HF0 and HF15 diet were assayed, since more dramatic effect of F&V was observed in mice fed the high fat diet. No differences in liver CerS2, CerS5, and CerS6 mRNA levels were found between mice fed the HF diet alone and mice fed the HF diet supplemented with 15% F&V (FIG. 14A-14C), indicating that the effect of F&V in reducing liver ceramide levels was not due to altered transcripts levels of CerS genes. While these results cannot rule out the possibility that F&V might alter CerS enzyme protein levels and/or activity, it is contemplated that the effect of F&V on ceramide level is due to reduction in activity of the enzyme sphingomyelinase (SMase), the enzyme that catalyzes the release of ceramide from sphingomyelin. Support for the hypothesis comes from the fact that F&V are rich in antioxidants, and SMase is regulated by redox homeostasis (Cinq-Frais et al., 2013; Martin et al., 2007). The activity of the liver neutral SMase (nSMase) was assayed and it was found that mice fed the HF0 diet alone had higher liver nSMase activity compared to mice fed the MC diet, and that mice fed the HF diet supplemented with 15% F&V had significantly lower nSMase activity compared to HF0 (FIG. 4E). No effect of increasing F&V consumption on liver nSMase activity was observed in mice fed the basal diet (FIG. 4D). These results are consistent with the results on the impact of obesity and F&V on liver ceramide levels (FIG. 3) and support that obesity induced increase in ceramide level and its reduction by F&V is mediated through decrease in nSMase activity.

Activation of liver FXR, a key regulator controlling various liver metabolic processes, suppresses liver inflammation by inhibiting NF-κB target inflammatory genes including TNFα (Y D et al., 2008). On the other hand, TNFα and HFD feeding down-regulate liver FXR expression (Geier et al., 2005; Kim et al., 2003; Nie et al., 2017). FXR agonist could upregulate HFD-induced down-regulation of FXR expression and inhibit TNFα and NF-κB signaling pathway (Hu et al., 2018). TNFα has been shown to stimulate a neutral plasma membrane-associated SMase activity leading to ceramides generation (Schutze et al., 1994) and contribute to the development and progression of NAFLD (De Taeye et al., 2007; Kakino et al., 2018). Furthermore, TNFα and ceramides are shown to play critical roles in the development of metabolic disorders including NAFLD and diabetes (Ilan, 2016; Rehman et al., 2017; Schmidt-Arras and Rose-John, 2016). Inflammatory cytokines TNFα and ceramide are also engaged in regulating each other's level. Further, ceramide can increase mitochondrial generation of reactive oxygen species resulting in inflammation and metabolic disorder such as NAFLD (Pagadala et al., 2012). Thus, to have a better understanding of underlying mechanism of obesity and F&V induced changes in adipose tissue inflammation and NAFLD, the levels of circulating and liver TNFα and liver FXR mRNA levels of mice fed a basal or HF diet supplemented with or without 15% F&V as well as mice fed MC diet were determined. It was found that, compared to the mice fed MC diet, those fed the HF diet alone showed significantly higher circulating and liver TNFα protein levels, lower liver FXR mRNA, and higher liver nSMase specific activity (FIG. 4A-4D). Feeding mice HF diet with 15% F&V prevented HF diet-induced decrease in liver FXR mRNA expression (FIG. 4B) as well as increase in liver nSMase specific activity (FIG. 4D) and trended to lower serum and liver TNFα levels (P=0.0761 and P=0.0971, respectively; FIGS. 4A and 4C). The mice fed the Basal diet with 15% F&V had significantly lower serum TNFα levels compared to those fed the Basal diet alone (p<0.001, FIG. 4E), but there were no dramatic differences in liver FXR mRNA levels, liver TNFα protein levels, and liver nSMase specific activity between mice fed the B0 1 diet and mice fed the B15 diet (FIG. 4F-4G). These results indicate that the preventive effect of F&V supplementation on NAFLD maybe partially mediated by modulating anti-inflammation gene the expression of the anti-inflammation gene, FXR, TNFα, and ceramides levels. This is supported by the result of the correlation analysis discussed below.

Figure 9:
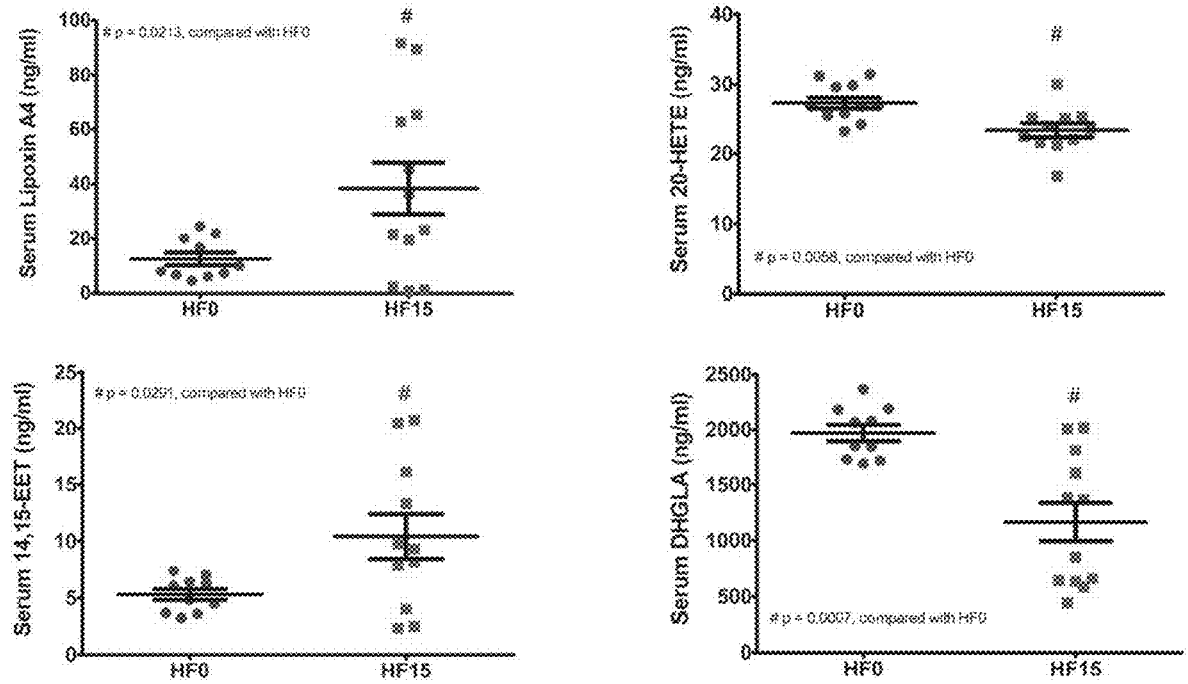
FIG. 9 shows

Compared to mice fed HFD alone, mice fed HFD supplemented with F&V had significantly higher serum levels of LXA4 and 14,15-EET (by 203% and 96%, respectively) and lower serum levels of 20-HETE and DHGLA (by 14% and 41%, respectively) (FIG. 9).

Spearman correlation analysis indicated significant positive correlations between TNFα levels and total ceramides, as well as C16:0, C20:0, C22:0, C24:0, and C24:1 ceramide species (Table 1). This indicates that TNFα may be involved in both HF diet-, and F&V-induced changes in ceramide levels. A significant positive correlation was also observed between TNFα and NAFLD (Table 1), supporting a link between TNFα, ceramide and NAFLD.

Figure 5:
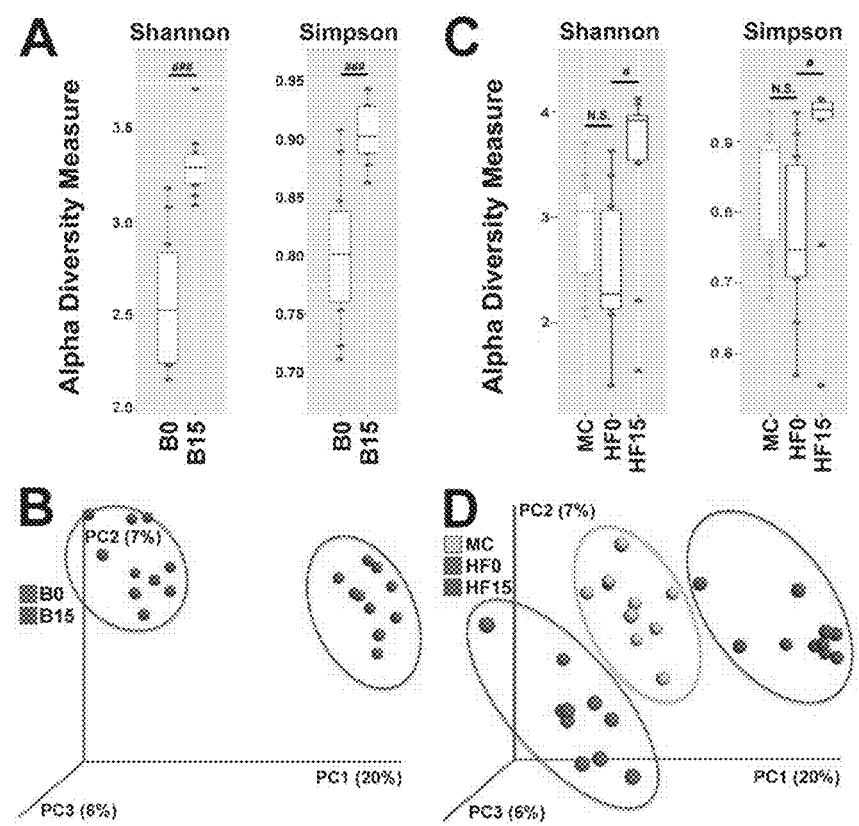
FIG. 5 shows that F&V supplementation in either basal or HF diet increased gut bacterial diversity. A and C: F&V treatment increased alpha-diversity in basal (A) and HF diet (B). B and D: Principal Coordinate Analysis plot with unweighted unifrac distance shows differential clustering of the three diet groups. #P<0.05; ###P<0.001. N.S. no significant.
Figure 6:
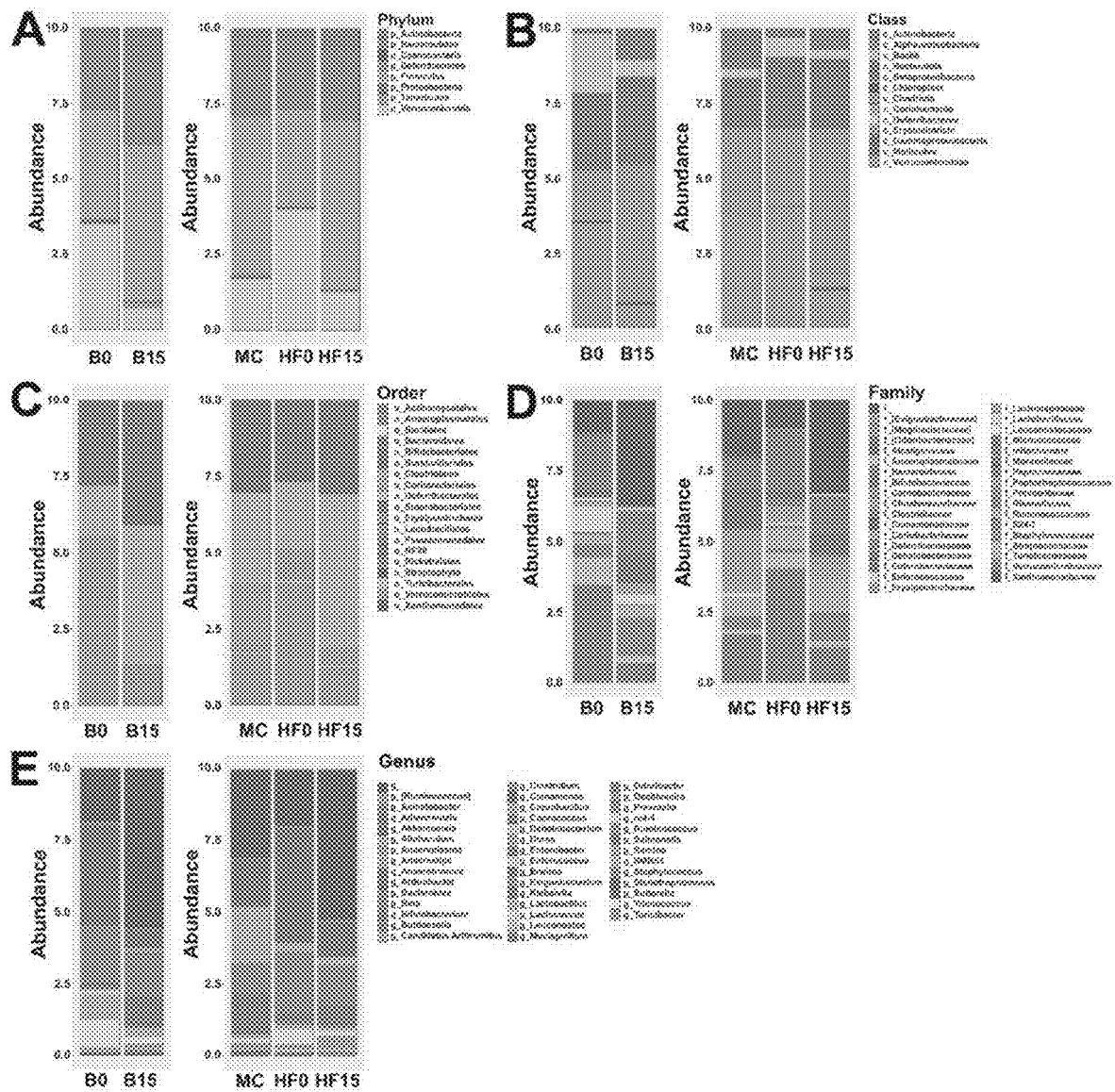
FIG. 6 shows that F&V supplementation changed bacterial community composition. Gut bacterial composition in different diets are shown in phylum level (A), class level (B), order level (C), family level (D) and genus level (E).

Gut Microbiota Dysbiosis was Mitigated by F&V Supplementation and was Associated with Biochemical and Clinical Outcomes To evaluate the effects of F&V supplementation on the gut microbiota, we performed 16S rRNA gene-based taxonomic profiling. Compared to mice fed Basal or HF diets alone, we found that mice fed the Basal or HF diets supplemented with F&V had significantly higher alpha diversity in fecal microbiota (FIGS. 5A and 5C). Principal Coordinate Analysis showed shifts in gut microbiota composition according to diet, with fecal microbiota composition differing the most according to F&V consumption in both diets (FIGS. 5B and 5D).

Furthermore, we observed changes in gut bacteria composition at all taxonomic levels.

Compared to mice fed the MC diet, those fed the HF diet had dramatically different gut bacteria composition. While mice fed the F&V-supplemented HF diet had microbial composition more similar to that of mice fed the MC diets than those fed the HF diet. Microbial composition of mice fed the F&V-supplemented basal diet had a different pattern from that of mice fed Basal diet (FIG. 6A-6E).

Figure 15:
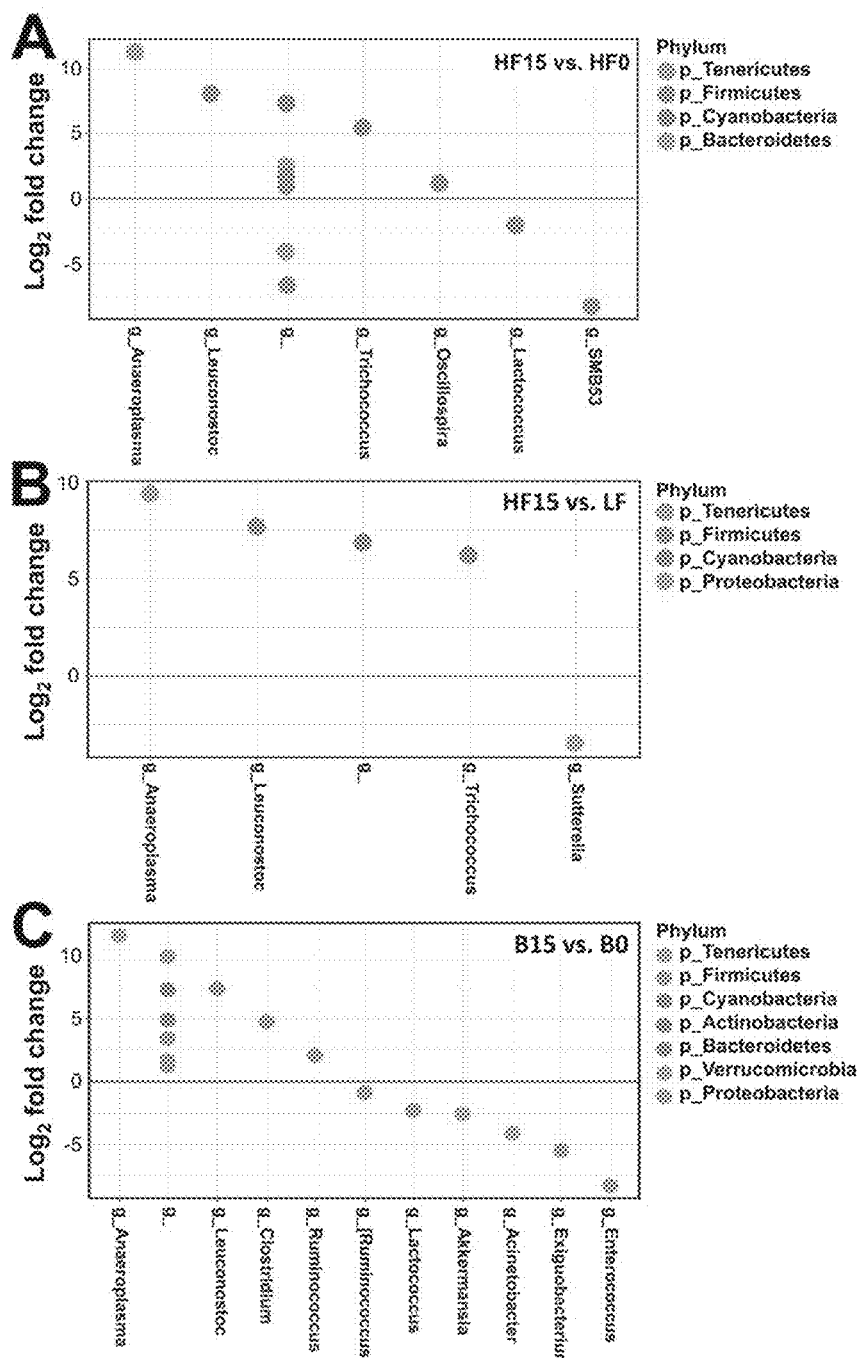
FIG. 15 shows that F&V supplementation significantly changed abundance of specific bacterial community composition. (A-D) Differential abundance of gut bacteria between groups was analyzed using Deseq2 package.
Figure 15:
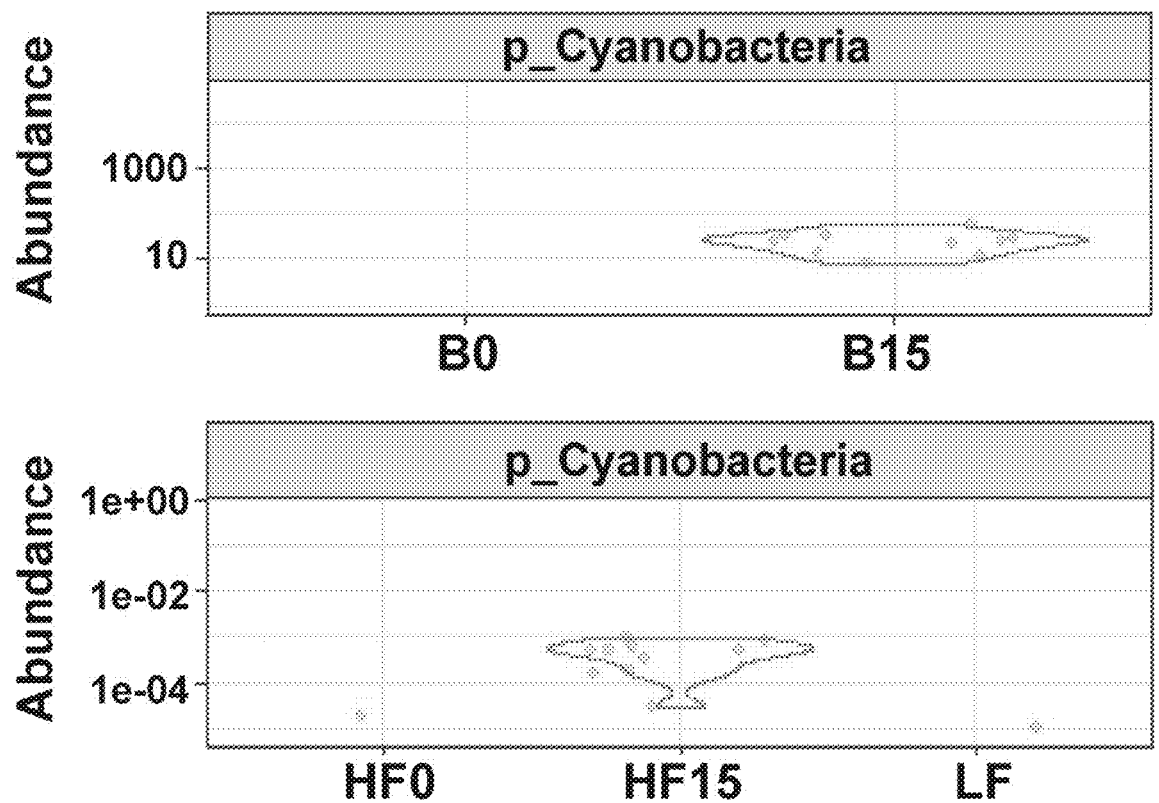
Figure 16:
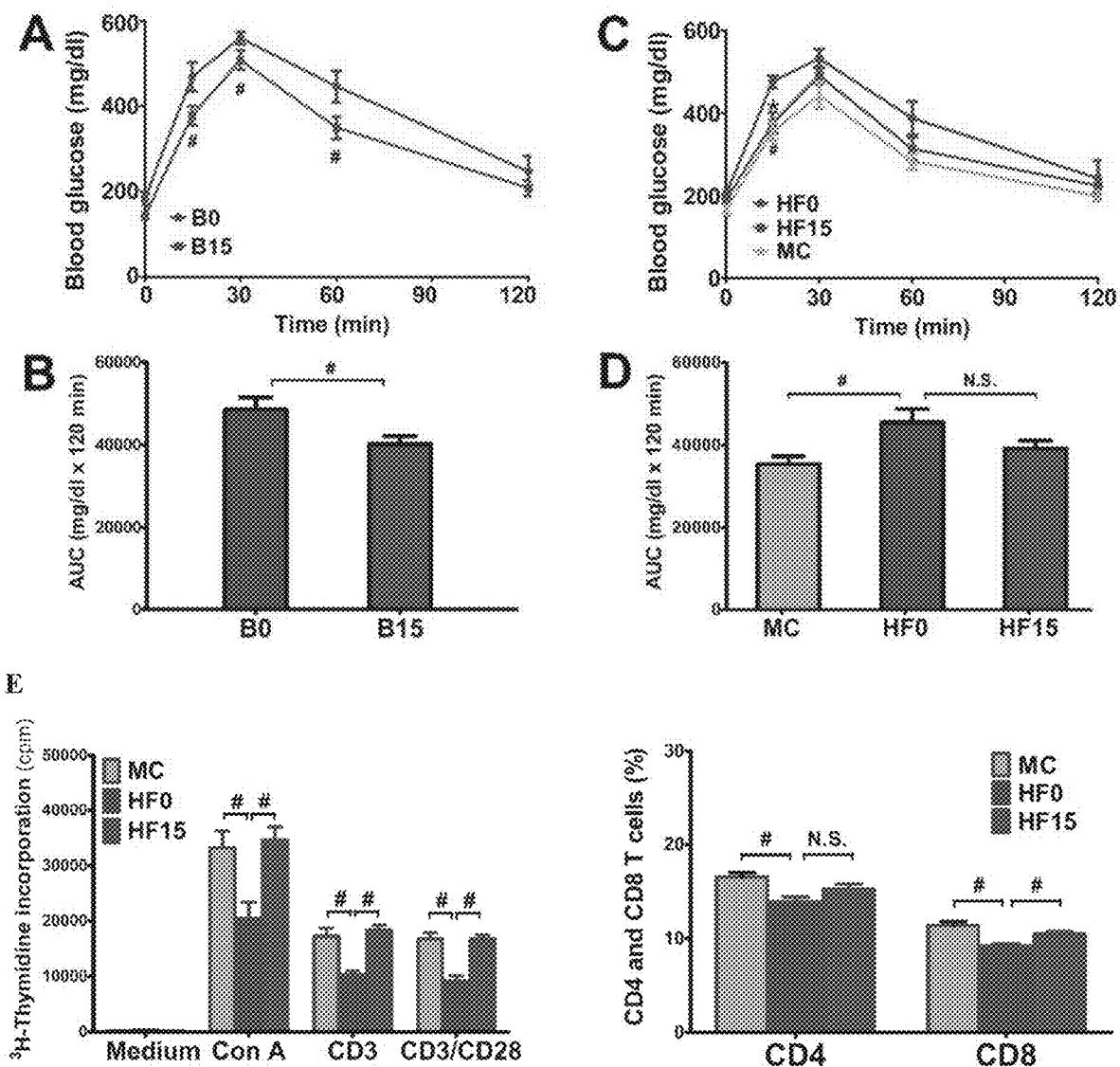
FIG. 16 shows that F&V supplementation improved glucose tolerance and diet-induced suppression of T cell proliferation and T cell expansion. (A-D) Intraperitoneal glucose tolerance test (IPGTT) was performed. (E) $^3$H-thymidine incorporation and % of CD4 and CD8 T cells.

Differential abundance analyses revealed a significantly higher abundance of following taxonomic groups in mice fed the HF15 diet compared to those fed the HF0 diet: *Anaeroplasma* (10×), *Leuconostoc* (7.5×), *Trichococcus* (5×), *Oscillospira* (~1.5×), 2 groups annotated to the Firmicutes phylum (~2×), one to the Bacteroidetes (2.5×) phylum, and one Cyanobacteria (7.5×). In contrast, several genera had lower abundances in mice fed the HF15 diet compared to those fed the HF0 diet: *Lactococcus* (~2.5×), SMB53 (−8×), and one unannotated group from the Firmicutes phylum (−7×), and one from the Bacteroidetes phylum (−4×) (FIG. 15A). *Anaeroplasma, Leuconostoc, Trichococcus*, and the unannotated genus from the Cyanobacteria phylum were also more abundant in the HF15-diet fed mice compared to the MC-diet fed mice (10×, 7.5×, 6×, and 7× more abundant, respectively, FIG. 15B). Similarly, the *Anaeroplasma* and *Leuconostoc* genera were more abundant in the B15 diet-fed mice compared to the B0 diet-fed mice (FIG. 15C).

Figure 7:
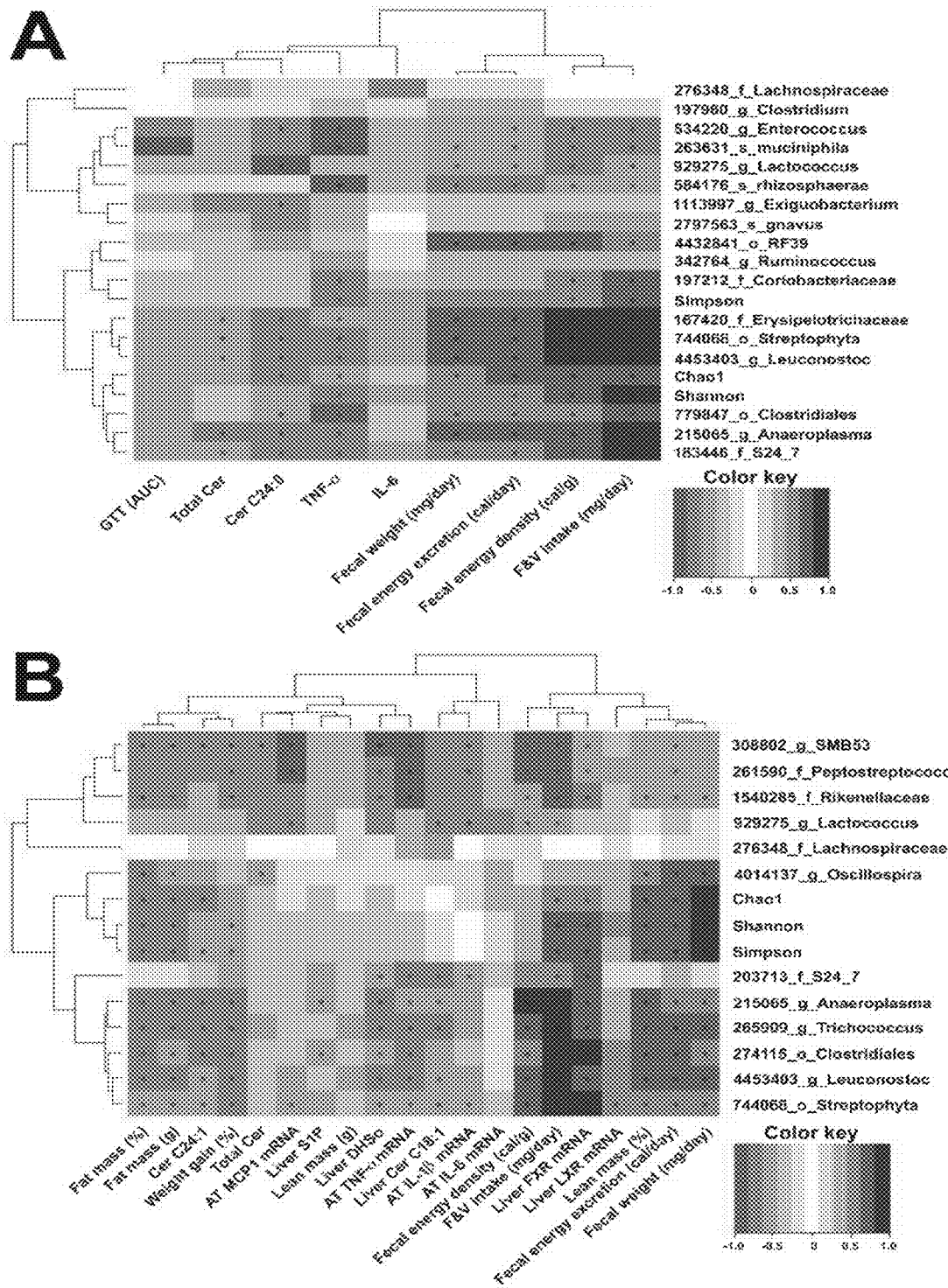
FIG. 7 shows a correlation matrix heatmap based on Spearman correlation coefficients comparing two diet feeding groups. (A). mice fed Basal diet with 0% or 15% F&V. (B). HF diet with 0% or 15% F&V. Star symbol indicates significant correlation after correcting for multiple testing using the Benjamini-Hochberg method.

Spearman correlation analyses showed that gut bacteria, which were positively correlated with F&V intake in mice fed the Basal diets (B0 & B15) were inversely associated with inflammation, ceramides, and positively associated with fecal energy excretion (FIG. 7A). Similarly, in mice fed the HF diet, bacteria that were positively correlated with F&V intake were positively correlated with a healthier metabolic profile, as seen by liver FXR mRNA expression and percent lean body mass, and negatively associated with fat mass, inflammation, and ceramides (FIG. 7B).

REFERENCES FOR EXAMPLE 1

Aburasayn, H., Al Batran, R., and Ussher, J. R. (2016). Targeting ceramide metabolism in obesity. Am J Physiol Endocrinol Metab 311, E423-435.

Alkhouri, N., Eng, K., Lopez, R., and Nobili, V. (2014). Non-high-density lipoprotein cholesterol (non-HDL-C) levels in children with nonalcoholic fatty liver disease (NAFLD). Springerplus 3, 407.

Arias-Loste, M. T., Fabrega, E., Lopez-Hoyos, M., and Crespo, J. (2015). The Crosstalk between Hypoxia and Innate Immunity in the Development of Obesity-Related Nonalcoholic Fatty Liver Disease. Biomed Res Int 2015, 319745.

Baumruker, T., and Prieschl, E. E. (2002). Sphingolipids and the regulation of the immune response. Semin Immunol 14, 57-63.

Bazzano, L. A., He, J., Ogden, L. G., Loria, C. M., Vupputuri, S., Myers, L., and Whelton, P. K. (2002). Fruit and vegetable intake and risk of cardiovascular disease in US adults: the first National Health and Nutrition Examination Survey Epidemiologic Follow-up Study. Am J Clin Nutr 76, 93-99.

Bibbo, S., Ianiro, G., Dore, M. P., Simonelli, C., Newton, E. E., and Cammarota, G. (2018). Gut Microbiota as a Driver of Inflammation in Nonalcoholic Fatty Liver Disease. Mediators Inflamm 2018, 9321643.

Booth, A., Magnuson, A., Fouts, J., and Foster, M. T. (2016). Adipose tissue: an endocrine organ playing a role in metabolic regulation. Horm Mol Biol Clin Investig 26, 25-42.

Bosy-Westphal, A., Braun, W., Albrecht, V., and Muller, M. J. (2019). Determinants of ectopic liver fat in metabolic disease. Eur J Clin Nutr 73, 209-214.

Chatrath, H., Vuppalanchi, R., and Chalasani, N. (2012). Dyslipidemia in patients with nonalcoholic fatty liver disease. Semin Liver Dis 32, 22-29.

Cheng, S., Wiklund, P., Autio, R., Borra, R., Ojanen, X., Xu, L., Tormakangas, T., and Alen, M. (2015). Adipose Tissue Dysfunction and Altered Systemic Amino Acid Metabolism Are Associated with Non-Alcoholic Fatty Liver Disease. PLoS One 10, e0138889.

Dbaibo, G. S., El-Assaad, W., Krikorian, A., Liu, B., Diab, K., Idriss, N. Z., El-Sabban, M., Driscoll, T. A., Perry, D. K., and Hannun, Y. A. (2001). Ceramide generation by two distinct pathways in tumor necrosis factor alpha-induced cell death. FEBS Lett 503, 7-12.

Eheim, A., Medrikova, D., and Herzig, S. (2014). Immune cells and metabolic dysfunction. Semin Immunopathol 36, 13-25.

Engin, A. (2017). Non-Alcoholic Fatty Liver Disease. Adv Exp Med Biol 960, 443-467.

Esmaillzadeh, A., Kimiagar, M., Mehrabi, Y., Azadbakht, L., Hu, F. B., and Willett, W. C. (2006). Fruit and vegetable intakes, C-reactive protein, and the metabolic syndrome. Am J Clin Nutr 84, 1489-1497.

Farias Santos, J., Suruagy Amaral, M., Lima Oliveira, S., Porto Barbosa, J., Rego Cabral, C., Jr., Sofia Melo, I., Bezerra Bueno, N., Duarte Freitas, J., Goulart Sant'ana, A., and Rocha Ataide, T. (2015). Dietary intake of ain-93 standard diet induces Fatty liver with altered hepatic fatty acid profile in Wistar rats. Nutr Hosp 31, 2140-2146.

Gadaleta, R. M., van Erpecum, K. J., Oldenburg, B., Willemsen, E. C., Renooij, W., Murzilli, S., Klomp, L. W., Siersema, P. D., Schipper, M. E., Danese, S., et al. (2011). Farnesoid X receptor activation inhibits inflammation and preserves the intestinal barrier in inflammatory bowel disease. Gut 60, 463-472.

Galic, S., Oakhill, J. S., and Steinberg, G. R. (2010). Adipose tissue as an endocrine organ. Mol Cell Endocrinol 316, 129-139.

Gonzalez, F. J., Jiang, C., and Patterson, A. D. (2016). An Intestinal Microbiota-Farnesoid X Receptor Axis Modulates Metabolic Disease. Gastroenterology 151, 845-859.

Gonzalez, F. J., Jiang, C., Xie, C., and Patterson, A. D. (2017). Intestinal Farnesoid X Receptor Signaling Modulates Metabolic Disease. Dig Dis 35, 178-184.

Guzik, T. J., Skiba, D. S., Touyz, R. M., and Harrison, D. G. (2017). The role of infiltrating immune cells in dysfunctional adipose tissue. Cardiovasc Res 113, 1009-1023.

Holt, E. M., Steffen, L. M., Moran, A., Basu, S., Steinberger, J., Ross, J. A., Hong, C.P., and Sinaiko, A. R. (2009). Fruit and vegetable consumption and its relation to markers of inflammation and oxidative stress in adolescents. J Am Diet Assoc 109, 414-421.

Ilan, Y. (2016). Compounds of the sphingomyelin-ceramide-glycosphingolipid pathways as secondary messenger molecules: new targets for novel therapies for fatty liver disease and insulin resistance. Am J Physiol Gastrointest Liver Physiol 310, G1102-1117.

Jeffery, I. B., and O'Toole, P. W. (2013). Diet-microbiota interactions and their implications for healthy living. Nutrients 5, 234-252.

Jiang, C., Xie, C., Li, F., Zhang, L., Nichols, R. G., Krausz, K. W., Cai, J., Qi, Y., Fang, Z. Z., Takahashi, S., et al. (2015). Intestinal farnesoid X receptor signaling promotes nonalcoholic fatty liver disease. J Clin Invest 125, 386-402.

Kakino, S., Ohki, T., Nakayama, H., Yuan, X., Otabe, S., Hashinaga, T., Wada, N., Kurita, Y., Tanaka, K., Hara, K., et al. (2018). Pivotal Role of TNF-alpha in the Development and Progression of Nonalcoholic Fatty Liver Disease in a Murine Model. Horm Metab Res 50, 80-87.

Katsiki, N., Mikhailidis, D. P., and Mantzoros, C. S. (2016). Non-alcoholic fatty liver disease and dyslipidemia: An update. Metabolism 65, 1109-1123.

Kim, D. H., Xiao, Z., Kwon, S., Sun, X., Ryerson, D., Tkac, D., Ma, P., Wu, S. Y., Chiang, C. M., Zhou, E., et al. (2015). A dysregulated acetyl/SUMO switch of FXR promotes hepatic inflammation in obesity. EMBO J 34, 184-199.

Kong, L. C., Holmes, B. A., Cotillard, A., Habi-Rachedi, F., Brazeilles, R., Gougis, S., Gausseres, N., Cani, P. D., Fellahi, S., Bastard, J. P., et al. (2014). Dietary patterns differently associate with inflammation and gut microbiota in overweight and obese subjects. PLoS One 9, e109434.

Kriss, M., Hazleton, K. Z., Nusbacher, N. M., Martin, C. G., and Lozupone, C. A. (2018). Low diversity gut microbiota dysbiosis: drivers, functional implications and recovery. Curr Opin Microbiol 44, 34-40.

Li, X., Watanabe, K., and Kimura, I. (2017). Gut Microbiota Dysbiosis Drives and Implies Novel Therapeutic Strategies for Diabetes Mellitus and Related Metabolic Diseases. Front Immunol 8, 1882.

Mizrahi, A., Knekt, P., Montonen, J., Laaksonen, M. A., Heliovaara, M., and Jarvinen, R. (2009). Plant foods and the risk of cerebrovascular diseases: a potential protection of fruit consumption. Br J Nut 102, 1075-1083.

Nakamura, T., Ichii, O., Irie, T., Kouguchi, H., Sotozaki, K., Chihara, M., Sunden, Y., Nagasaki, K. I., Tatsumi, O., Elewa, Y. H. A., et al. (2018). Cotton rat (*Sigmodon hispidus*) develops metabolic disorders associated with visceral adipose inflammation and fatty pancreas without obesity. Cell Tissue Res.

Nikolova-Karakashian, M. (2018). Alcoholic and non-alcoholic fatty liver disease: Focus on ceramide. Adv Biol Regul 70, 40-50.

Paniagua, J. A. (2016). Nutrition, insulin resistance and dysfunctional adipose tissue determine the different components of metabolic syndrome. World J Diabetes 7, 483-514.

Paredes-Turrubiarte, G., Gonzalez-Chavez, A., Perez-Tamayo, R., Salazar-Vazquez, B. Y., Hernandez, V. S., Garibay-Nieto, N., Fragoso, J. M., and Escobedo, G. (2016). Severity of non-alcoholic fatty liver disease is associated with high systemic levels of tumor necrosis factor alpha and low serum interleukin 10 in morbidly obese patients. Clin Exp Med 16, 193-202.

Polyzos, S. A., Kountouras, J., and Mantzoros, C. S. (2017). Adipose tissue, obesity and non-alcoholic fatty liver disease. Minerva Endocrinol 42, 92-108.

Qin, J., Li, Y., Cai, Z., Li, S., Zhu, J., Zhang, F., Liang, S., Zhang, W., Guan, Y., Shen, D., et al. (2012). A metagenome-wide association study of gut microbiota in type 2 diabetes. Nature 490, 55-60.

Regnier, M., Polizzi, A., Guillou, H., and Loiseau, N. (2018). Sphingolipid metabolism in non-alcoholic fatty liver diseases. Biochimie.

Rehman, K., Akash, M. S. H., Liaqat, A., Kamal, S., Qadir, M. I., and Rasul, A. (2017). Role of Interleukin-6 in Development of Insulin Resistance and Type 2 Diabetes Mellitus. Crit Rev Eukaryot Gene Expr 27, 229-236.

Ridaura, V. K., Faith, J. J., Rey, F. E., Cheng, J., Duncan, A. E., Kau, A. L., Griffin, N. W., Lombard, V., Henrissat, B., Bain, J. R., et al. (2013). Gut microbiota from twins discordant for obesity modulate metabolism in mice. Science 341, 1241214.

Root, M. M., McGinn, M. C., Nieman, D. C., Henson, D. A., Heinz, S. A., Shanely, R. A., Knab, A. M., and Jin, F. (2012). Combined fruit and vegetable intake is correlated with improved inflammatory and oxidant status from a cross-sectional study in a community setting. Nutrients 4, 29-41.

Saltzman, E. T., Palacios, T., Thomsen, M., and Vitetta, L. (2018). Intestinal Microbiome Shifts, Dysbiosis, Inflammation, and Non-alcoholic Fatty Liver Disease. Front Microbiol 9, 61.

Samad, F., Badeanlou, L., Shah, C., and Yang, G. (2011). Adipose tissue and ceramide biosynthesis in the pathogenesis of obesity. Adv Exp Med Biol 721, 67-86.

Santos, J. C., de Araujo, O. R., Valentim, I. B., de Andrade, K. Q., Moura, F. A., Smaniotto, S., dos Santos, J. M., Gasparotto, J., Gelain, D. P., and Goulart, M. O. (2015). Choline and Cystine Deficient Diets in Animal Models with Hepatocellular Injury: Evaluation of Oxidative Stress and Expression of RAGE, TNF-alpha, and IL-1beta. Oxid Med Cell Longev 2015, 121925.

Sanyal, A. J., and Pacana, T. (2015). A Lipidomic Readout of Disease Progression in A Diet-Induced Mouse Model of Nonalcoholic Fatty Liver Disease. Trans Am Clin Climatol Assoc 126, 271-288.

Schmidt-Arras, D., and Rose-John, S. (2016). IL-6 pathway in the liver: From physiopathology to therapy. J Hepatol 64, 1403-1415.

Schmitt, J., Kong, B., Stieger, B., Tschopp, O., Schultze, S. M., Rau, M., Weber, A., Mullhaupt, B., Guo, G. L., and Geier, A. (2015). Protective effects of farnesoid X receptor (FXR) on hepatic lipid accumulation are mediated by hepatic FXR and independent of intestinal FGF15 signal. Liver Int 35, 1133-1144.

Serafini, M., and Peluso, I. (2016). Functional Foods for Health: The Interrelated Antioxidant and Anti-Inflammatory Role of Fruits, Vegetables, Herbs, Spices and Cocoa in Humans. Curr Pharm Des 22, 6701-6715.

Sheflin, A. M., Melby, C. L., Carbonero, F., and Weir, T. L. (2017). Linking dietary patterns with gut microbial composition and function. Gut Microbes 8, 113-129.

Sittipo, P., Lobionda, S., Lee, Y. K., and Maynard, C. L. (2018). Intestinal microbiota and the immune system in metabolic diseases. J Microbiol 56, 154-162.

Strissel, K. J., Stancheva, Z., Miyoshi, H., Perfield, J. W., 2nd, DeFuria, J., Jick, Z., Greenberg, A. S., and Obin, M. S. (2007). Adipocyte death, adipose tissue remodeling, and obesity complications. Diabetes 56, 2910-2918.

Tindall, A. M., Petersen, K. S., and Kris-Etherton, P. M. (2018). Dietary Patterns Affect the Gut Microbiome—The Link to Risk of Cardiometabolic Diseases. J Nutr 148, 1402-1407.

Turnbaugh, P. J., Hamady, M., Yatsunenko, T., Cantarel, B. L., Duncan, A., Ley, R. E., Sogin, M. L., Jones, W. J., Roe, B. A., Affourtit, J. P., et al. (2009). A core gut microbiome in obese and lean twins. Nature 457, 480-484.

van Beek, L., van Klinken, J. B., Pronk, A. C., van Dam, A. D., Dirven, E., Rensen, P. C., Koning, F., Willems van Dijk, K., and van Harmelen, V. (2015). The limited storage capacity of gonadal adipose tissue directs the development of metabolic disorders in male C57Bl/6J mice. Diabetologia 58, 1601-1609.

van Greevenbroek, M. M., Schalkwijk, C. G., and Stehouwer, C. D. (2016). Dysfunctional adipose tissue and low-grade inflammation in the management of the metabolic syndrome: current practices and future advances. F1000Res 5.

Wang, K., Shan, S., Zheng, H., Zhao, X., Chen, C., and Liu, C. (2018). Non-HDL-cholesterol to HDL-cholesterol ratio is a better predictor of new-onset non-alcoholic fatty liver disease than non-HDL-cholesterol: a cohort study. Lipids Health Dis 17, 196.

Wannamethee, S. G., Lowe, G. D., Rumley, A., Bruckdorfer, K. R., and Whincup, P. H. (2006). Associations of vitamin C status, fruit and vegetable intakes, and markers of inflammation and hemostasis. Am J Clin Nutr 83, 567-574; quiz 726-567.

Wei, S., Liu, S., Su, X., Wang, W., Li, F., Deng, J., Lyu, Y., Geng, B., and Xu, G. (2018). Spontaneous development of hepatosteatosis in perilipin-1 null mice with adipose tissue dysfunction. Biochim Biophys Acta Mol Cell Biol Lipids 1863, 212-218.

Wieland, A., Frank, D. N., Harnke, B., and Bambha, K. (2015). Systematic review: microbial dysbiosis and non-alcoholic fatty liver disease. Aliment Pharmacol Ther 42, 1051-1063.

Wong, J. M. (2014). Gut microbiota and cardiometabolic outcomes: influence of dietary patterns and their associated components. Am J Clin Nutr 100 Suppl 1, 369S-377S.

Xie, C., Jiang, C., Shi, J., Gao, X., Sun, D., Sun, L., Wang, T., Takahashi, S., Anitha, M., Krausz, K. W., et al. (2017). An Intestinal Farnesoid X Receptor-Ceramide Signaling Axis Modulates Hepatic Gluconeogenesis in Mice. Diabetes 66, 613-626.

Yanaga, F., and Watson, S. P. (1992). Tumor necrosis factor alpha stimulates sphingomyelinase through the 55 kDa receptor in HL-60 cells. FEBS Lett 314, 297-300.

Yao, L., Seaton, S. C., Ndousse-Fetter, S., Adhikari, A. A., DiBenedetto, N., Mina, A. I., Banks, A. S., Bry, L., and Devlin, A. S. (2018). A selective gut bacterial bile salt hydrolase alters host metabolism. Elife 7.

Yousef, M. H., Al Juboori, A., Albarrak, A. A., Ibdah, J. A., and Tahan, V. (2017). Fatty liver without a large "belly": Magnified review of non-alcoholic fatty liver disease in non-obese patients. World J Gastrointest Pathophysiol 8, 100-107.

Zelber-Sagi, S., Salomone, F., Yeshua, H., Lotan, R., Webb, M., Halpern, Z., Santo, E., Oren, R., and Shibolet, O. (2014). Non-high-density lipoprotein cholesterol independently predicts new onset of non-alcoholic fatty liver disease. Liver Int 34, e128-135.

Zhang, Q. Q., and Lu, L. G. (2015). Nonalcoholic Fatty Liver Disease: Dyslipidemia, Risk for Cardiovascular Complications, and Treatment Strategy. J Clin Transl Hepatol 3, 78-84.

Zhang, X., Shu, X. O., Xiang, Y. B., Yang, G., Li, H., Gao, J., Cai, H., Gao, Y. T., and Zheng, W. (2011). Cruciferous vegetable consumption is associated with a reduced risk of total and cardiovascular disease mortality. Am J Clin Nutr 94, 240-246.

Example 2

Dietary Fruit and Vegetable Supplementation Suppress Diet-induced Atherosclerosis in LDL Receptor Knockout Mice Materials and Methods Fruits and Vegetables (F&V) Powder Preparation F&V mixture containing a combination of 24 of the most commonly consumed F&V based on USDA census data was homogenized to prepare the freeze-dried powder as described in Example 1.

Animals and Diets

Four-week-old male LDL receptor knockout mice (B6.129S7-Ldlr$^{tm1Her}$/J, stock number 002207) were purchased from The Jackson Laboratory (Bar Harbor, ME, USA) and housed at the animal care facility at Jean Mayer USDA Human Nutrition Research Center on Aging at Tufts University. After 12 days of acclimation, individually caged animals were assigned into weight-matched three groups, including low fat diet (LF) group, high fat diet (HF0) group, and high fat diet supplemented with 15% of F&V mixture (HF15) group. The LF diet was made of modified AIN-93M diet, with 10% kcal from fat (4.4% kcal from cocoa butter/5.6% kcal from soybean oil, Research Diets, #D17030910M) and 52 mg cholesterol/1000 kcal added. The HF0 diet was consisted of modified AIN-93M diet, with 27% kcal from fat (24.2% kcal from cocoa butter/2.8% kcal from soybean oil, Research Diets, #D17030911M) and 130 mg cholesterol/1000 kcal included. The HF15 diet was prepared by replacing 15% HF0 diet with 15% F&V mixture (w/w) (equivalent to 8-9 servings of F&V/day for humans). Mice were fed ad libitum with respective diets for 20-weeks. The body weight were recorded weekly, and fecal sample was collected for gut microbiome analysis.

Animal Blood Collection and Organ Isolation

After 20 weeks, mice were euthanized. Blood sample was collected by cardiac puncture from each animal, and serum were isolated and stored in −80° C. for further analysis. Subsequently, the thoracic cavity was opened, and the aorta was isolated as previously reported [1]. Liver was dissected out and weighed, then sectioned into two pieces, one in formalin, and one in foil then frozen in liquid nitrogen and then transferred to −80° C. for storage.

Aortic Lesion Area Quantification

The isolated descending aorta, stored in a 10% buffered formaldehyde solution, were cleared of fat and cut longitudinally, and then pinned down on a black wax platform using insect pins. Aortic lesions were visualized through staining with freshly prepared Oil Red O in isopropanol. Resulting images were captured under a dissection microscope. Aortic atheroma lesion area was evaluated with Adobe Photoshop CC 2015 software (Adobe Systems, Mountain View, CA), and the ratios of the plaque area stained with oil red O over total aorta area were quantitated.

Hepatic Steatosis Analysis

Fixed liver tissue were processed for histopathology to measure lipid accumulation. Hepatic steatosis area was quantitated with formalin-fixed H&E stained sections, and the percentage of the lipid area to the total area was calculated using ImageJ (Neuberger and James 1999). Non-hepatocyte areas such as sinusoids, portal tracts, and hepatic veins were excluded for the analysis.

Gene-Expression Analyses

Total RNA was extracted from frozen liver tissue using TRIzol reagent (Invitrogen). Complementary DNA (cDNA) was generated by reverse-transcription of 1 µg total RNA using Super Script III First-Strand Synthesis System (Invitrogen). Gene expression levels of interest were quantitated by using SYBR Green reagent. Results are represented as a fold change in comparative expression level. Sequences of forward or reverse oligonucleotide primers are listed below in Table 6.

Results

F&V Supplementation Suppressed High Fat Diet-Induced Aortic Atherosclerosis in LDLR KO Mouse.

Figure 17:
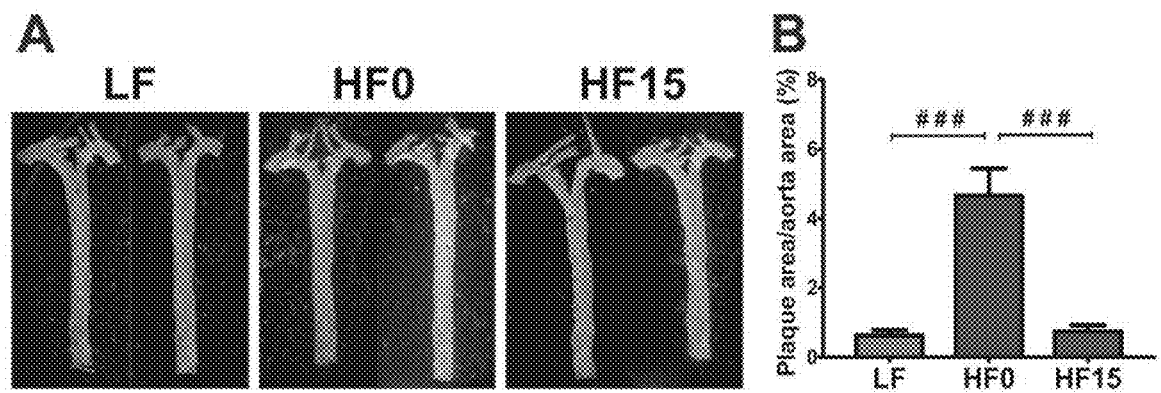
FIG. 17 shows that F&V supplementation suppressed high fat diet-induced aortic atherosclerosis in LDLR KO mouse. Four-week old male LDL receptor knockout mice were fed a low fat diet (LF, 10% calories from fat; 52 mg cholesterol/1000 kcal), or high fat diet (HF, 27% calories from fat; 130 mg cholesterol/1000 kcal) or HF diet with 15% F&V supplementation (HF15), respectively, for 20 weeks. (A_Representative images of aortas stained en face with Oil Red O. (B) the ratios of the plaque area stained with oil red O over total aorta area were quantitated. ###P<0.001.

To determine the effectiveness of F&V supplementation on atherosclerotic lesion formation in LDLR KO mice, aortic atherosclerosis lesion area was measured by en face Oil Red O staining. Mice fed HF0 diet had larger aortic atherosclerotic lesion area than mice fed LF diet (6.5 fold increase). Compared to mice fed HF0, the aortic lesion steatosis in mice fed HF15 diet reduced more than 80% (FIG. 17). These results indicate that F&V supplementation suppressed high fat diet-induced aortic atherosclerosis in LDLR KO mouse.

Figure 18:
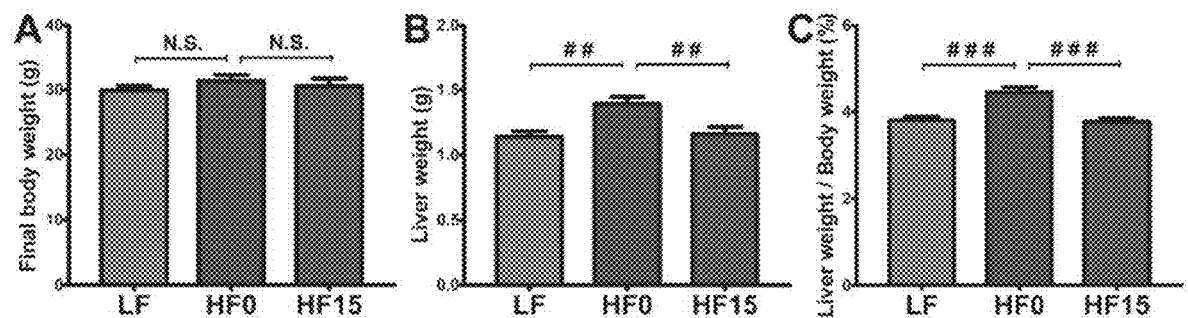
FIG. 18 shows effects of F&V supplementation on body weight and liver weight in LDLR KO mouse. (A-C) Liver weight was measured and percentage of liver weight to body was calculated. ##P<0.01, ###P<0.001, N.S. no significance.

F&V Supplementation Prevented High Fat Diet-Induced Hepatic Steatosis in LDLR KO Mouse There were no significant differences with body weight among three groups (FIG. 18A). However, liver weight and the ratio of liver weight over final body weight were higher in mice fed HF0 diet than in mice fed LF diet. Mice fed HF15 diet had lower liver weight and the ratio of liver weight over final body weight compared to mice fed HF0 diet (FIGS. 18B and 18C). The effects of FV on hepatic

TABLE 6

| | Official Symbol | Gene ID | Forward Sequence | Reverse Sequence |
|---|---|---|---|---|
| Hprt1 | Hprt | 15452 | AAGCTTGCTGGTGAAAAGGA (SEQ ID NO: 1) | TTGCGCTCATCTTAGGCTTT (SEQ ID NO: 2) |
| TNFα | Tot | 21926 | TTGCTCTGTGAAGGGAATGG (SEQ ID NO: 3) | GGCTCTGAGGAGTAGACAATAAAG (SEQ ID NO: 4) |
| FAS | Fasn | 14104 | CCCTTGATGAAGAGGGATCA (SEQ ID NO: 5) | ACTCCACAGGTGGGAACAAG (SEQ ID NO: 6) |

Measurement of Serum Pro-Inflammatory Cytokine Levels and Serum Lipids Profiling Mouse serum pro-inflammatory cytokine levels were determined using electrochemiluminescent multiplex assays and serum lipids profiling was performed by Nutritional Evaluation Laboratory at HNRCA.

16S rDNA Microbiota Profiling

Bacterial genomic DNA was extracted using the QIAamp Stool DNA Kit (Qiagen, Germantown, MD) following manufacturer's instruction. Amplicons of the V4 region of the bacterial 16S ribosomal DNA were generated by PCR, and amplicon pools were sequenced on a MiSeq sequencer (Illumina). QIIME analysis were performed and an OTU table was generated by the Tufts University Core Facility Genomics Core. Shannon and Simpson diversity index were determined, and unweighted UniFrac analysis was conducted. Data were analyzed using Bioconductor Workflow. Kruskal-Wallis test was performed for each diversity metric, followed by a Wilcoxon Rank Sum test for pairwise comparisons with false discovery rate (FDR) correction [2-4].

Statistical Analysis

Figure 19:
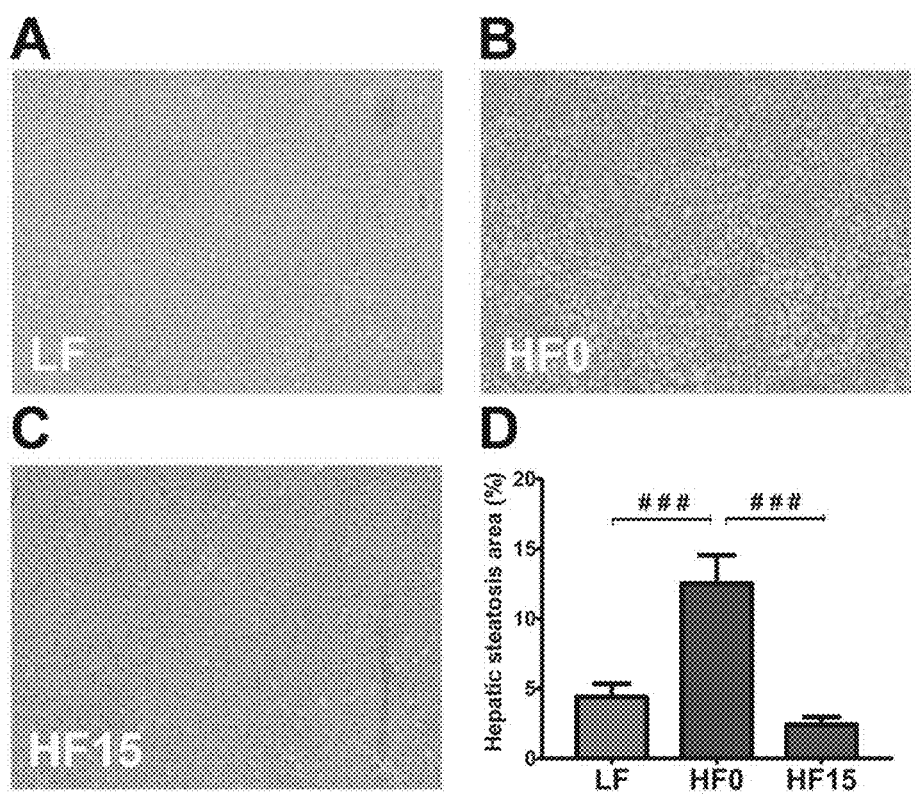
FIG. 19 shows that F&V supplementation prevented high fat diet-induced hepatic steatosis in LDLR KO mouse. (A), HF0 diet (B), and HF15 diet (C). D, Quantitation of hepatic steatosis area of three diet groups. ###P<0.001.

Data are presented as mean±SE and were analyzed by one-way ANOVA followed by Dunnett's post-hoc test. Correlation coefficients were calculated by using a nonparametric Spearman's rank correlation; and p values from Spearman correlation analysis of gut bacterial abundance and clinical biomarkers were corrected for false detection rate using the Benjamini-Hochberg method. Differential abundance of gut bacteria between groups was analyzed using Deseq2 package. Significance was set at p<0.05.

steatosis were examined. Mice fed HF0 diet had larger hepatic steatosis area than mice fed LF diet (1.9 fold increase). Compared to mice fed HF0 diet, the hepatic steatosis area in mice fed HF15 diet reduced more than 80% (FIG. 19).

Figure 20:
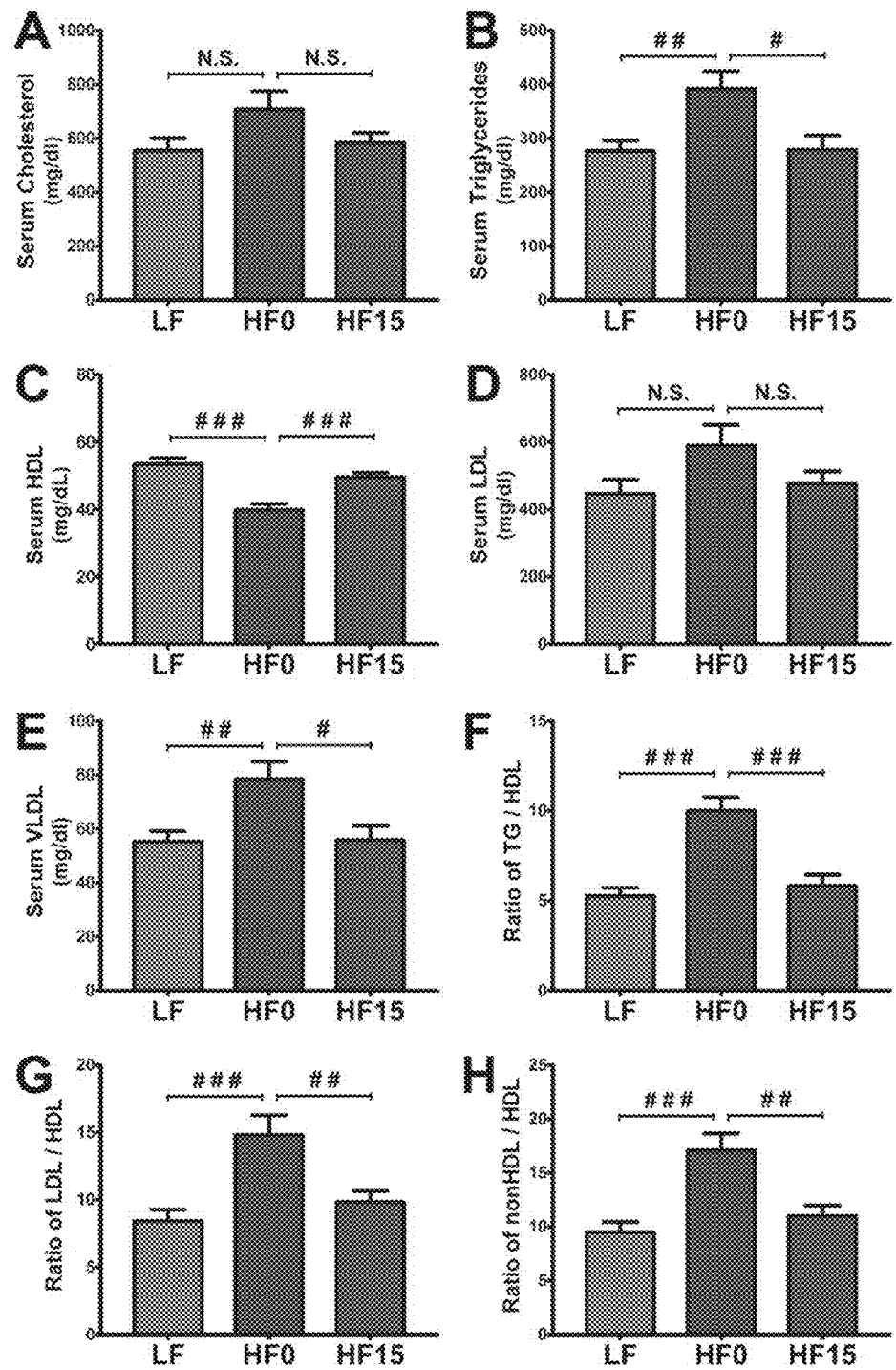
FIG. 20 shows that F&V supplementation improved dyslipidemia in LDLR KO mouse. Plasma lipids profile (A-E) was determined. Ratio of TG/HDL (F), LDL/HDL (G), non HDL/HDL (H), and plasma VLDL (I) were calculated. #P<0.05, ##P<0.01, ###P<0.001. N.S. no significant.
Figure 20:
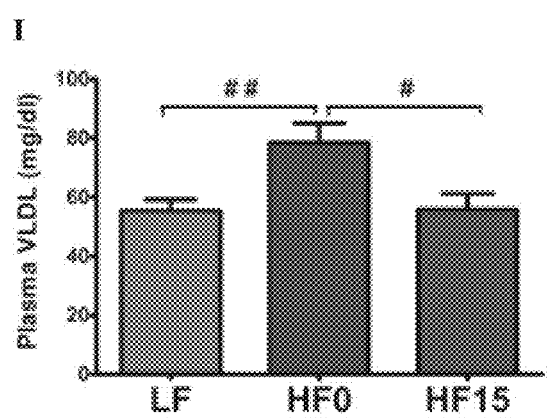

Effects of F&V Supplementation on Suppression of Aortic Atherosclerosis and Prevention of Hepatic Steatosis are Associated with Improvement of Diet-Induced Dyslipidemia and Reduction of Serum TNFα Levels in LDLR KO Mouse As dysregulated lipids metabolism is associated with pathogenesis of atherosclerosis, plasma lipid profile was assessed. Mice fed HF0 diet had significantly higher plasma triglyceride (TG) and low-density lipoprotein (LDL) cholesterol and lower high-density lipoprotein (HDL) cholesterol levels than mice fed LF diet. Mice fed HF15 diet significantly improved dyslipidemia to the levels similar to LF-fed mice (FIG. 20A-4E). Furthermore, the ratio of TG/HDL (FIG. 20F), LDL/HDL (FIG. 20G), and non HDL/HDL (FIG. 20H) were higher in mice fed HF0 than in mice fed LF. Mice fed HF15 diet had lower ratio of TG/HDL (FIG. 20F), LDL/HDL (FIG. 20G), and non HDL/HDL (FIG. 20H) than mice fed HF0 diet, indicating that F&V improved diet-induced dyslipidemia in LDLR KO mouse.

Figure 21:
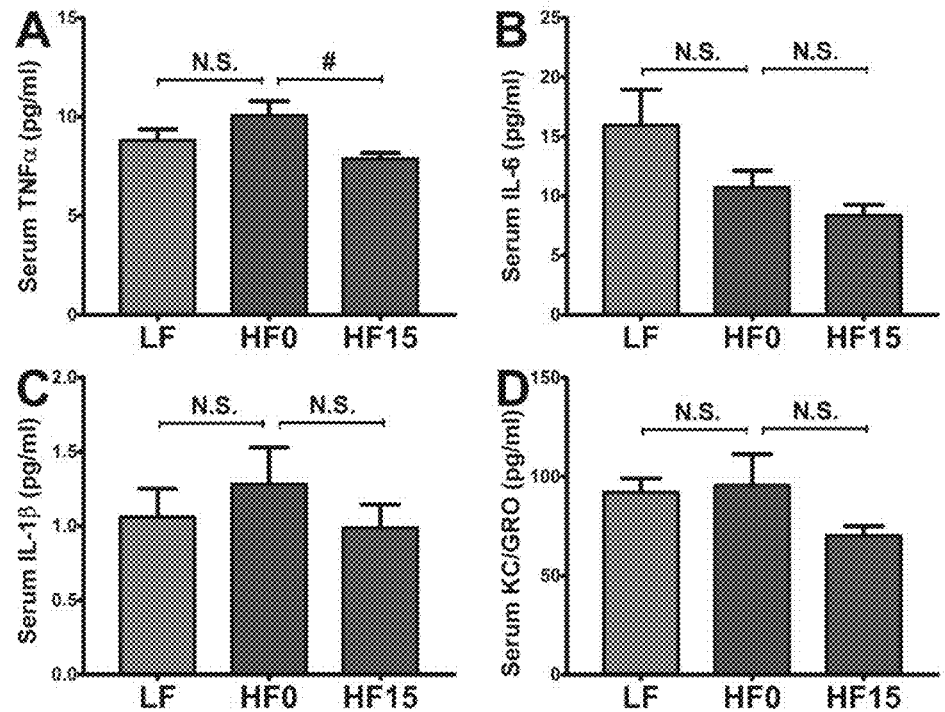
FIG. 21 shows effects of F&V supplementation on plasma pro-inflammatory cytokine levels in LDLR KO mouse. (A-D) Serum cytokine levels were determined by using the Meso Scale Discovery (MSD) multiplex ELISA platform. #P<0.05, ##P<0.01, ###P<0.001. N.S. no significant.

It was investigated whether effects of F&V supplementation on suppression of high fat diet-induced aortic atherosclerosis and prevention of hepatic steatosis in LDLR KO mouse is mediated through reduction of circulating pro-inflammatory cytokine levels. F&V supplementation significantly reduced serum TNFα levels (FIG. 21A). Other pro-inflammatory cytokine levels, such as serum IL-6 (FIG.

21B), IL-1β (FIG. 21C), and KC/GRO (FIG. 21D), trended to be lower in mouse fed HF15 diet compared to those fed HF0 diet.

Since F&V supplementation alleviated dyslipidemia and reduced serum TNFα levels, mRNA levels of liver fatty acid synthase (Fasn), a key lipogenic enzyme involved in de novo lipid biosynthesis, and TNFα, which plays critical role in fatty liver pathogenesis and may be involved in atherogenesis [5-8] were determined. It was found that mice fed HF0 diet had higher mRNA levels of Fasn and TNFα in liver tissue than mice fed LF diet (FIGS. 22A and 22B). Compared to mice fed HF0 diet, mice fed HF15 diet had significant lower expression levels of these two genes (FIGS. 22A and 22B).

Figure 22:
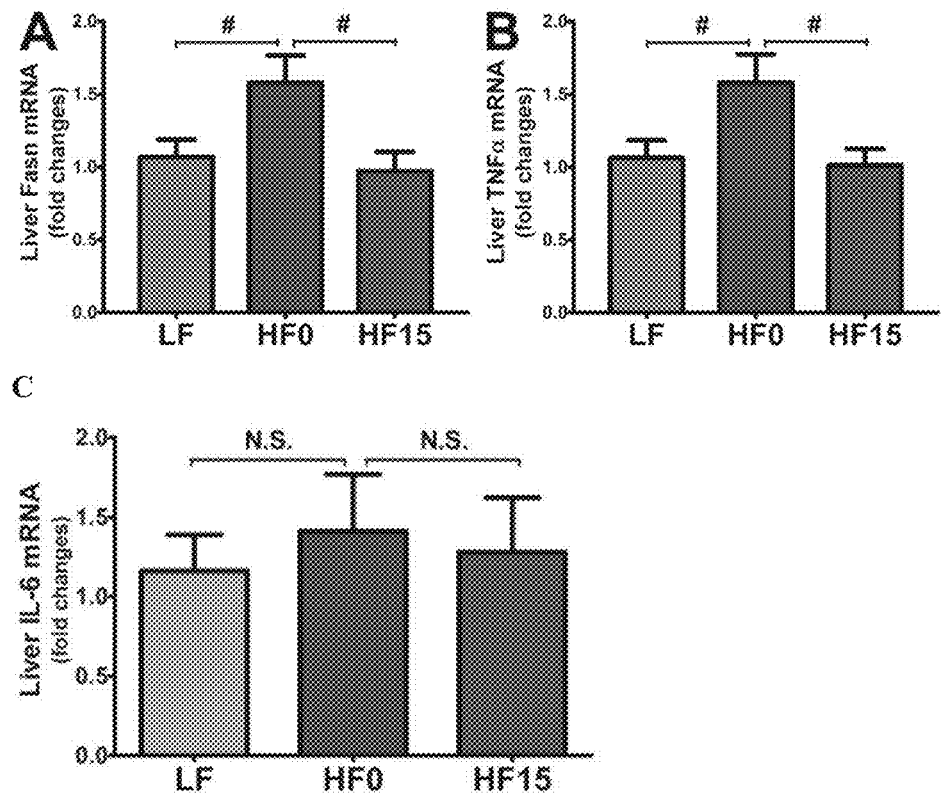
FIG. 22 shows that F&V supplementation reduced liver mRNA levels of cytokines in LDLR KO mouse. (A-D) Liver mRNA levels of Fasn, IL-6, PPARg, SREBF 1and TNFα were quantitated using RTqPCR. #P<0.05.
Figure 22:
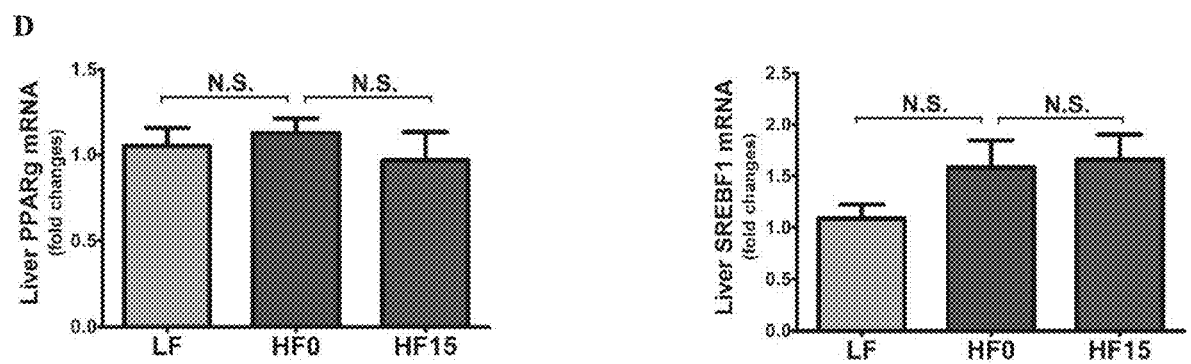
Figure 23:
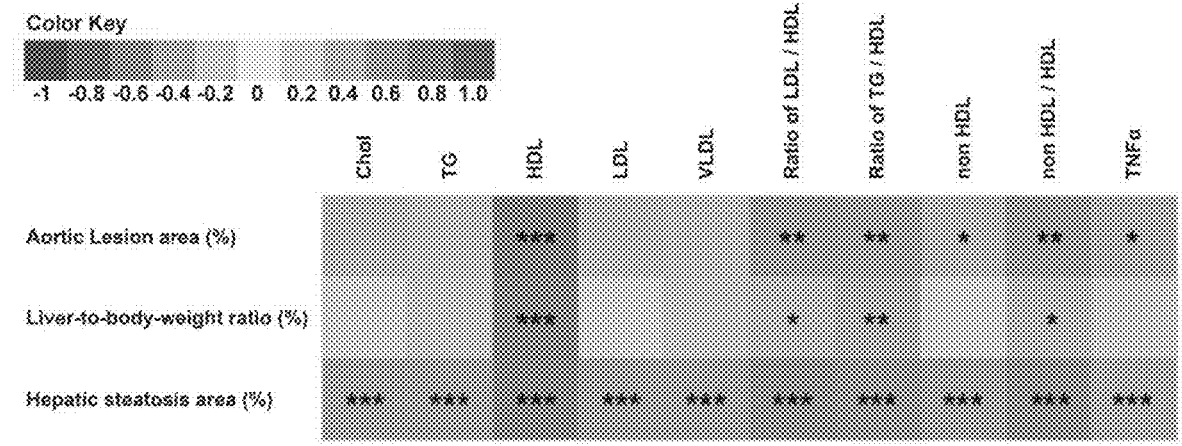
FIG. 23 shows a heatmap of Spearman's correlations shows aortic atherosclerotic lesion and hepatic steatosis area vs plasma TNFα and lipid profile in LDLR KO mouse. #P<0.05, ##P<0.01, ###P<0.001.

Circulating pro-inflammatory cytokine TNFα levels and dyslipidemia are known to play critical roles in pathogenesis of atherosclerosis [5, 6, 9-11] and hepatic steatosis [7, 12, 13]. Therefore, Spearman correlation analysis was performed. It was found that aortic atherosclerotic lesion and hepatic steatosis area were negatively correlated with plasma HDL ($p<0.001$, respectively) and positively and significantly associated with TNFα and ratio of LDL/HDL, TG/HDL, and non HDL/HDL (FIG. 22). Our results indicate that the F&V mixture prevented HF-induced atherosclerosis and hepatic steatosis, which may be mediated by reducing plasma TNFα levels and improving dyslipidemia.

F&V Supplementation Mitigated Gut Microbiota Dysbiosis in LDLR KO Mouse

Figure 24:
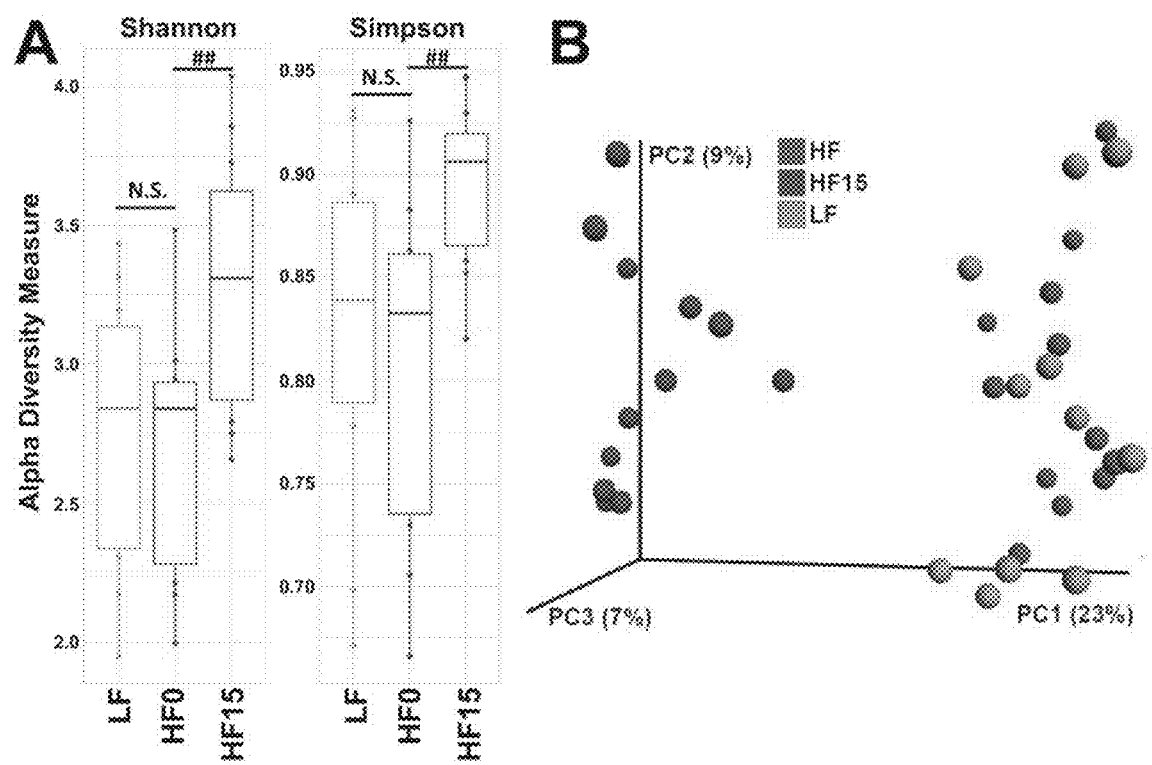
FIG. 24 shows that F&V supplementation in HF diet increased gut bacterial diversity. (A) F&V treatment increased alpha-diversity. (B) Principal Coordinate Analysis plot with unweighted unifrac distance shows differential clustering of the HF15 diet group from LF diet group and HF0 group. ##P<0.01. N.S. no significant.
Figure 25:
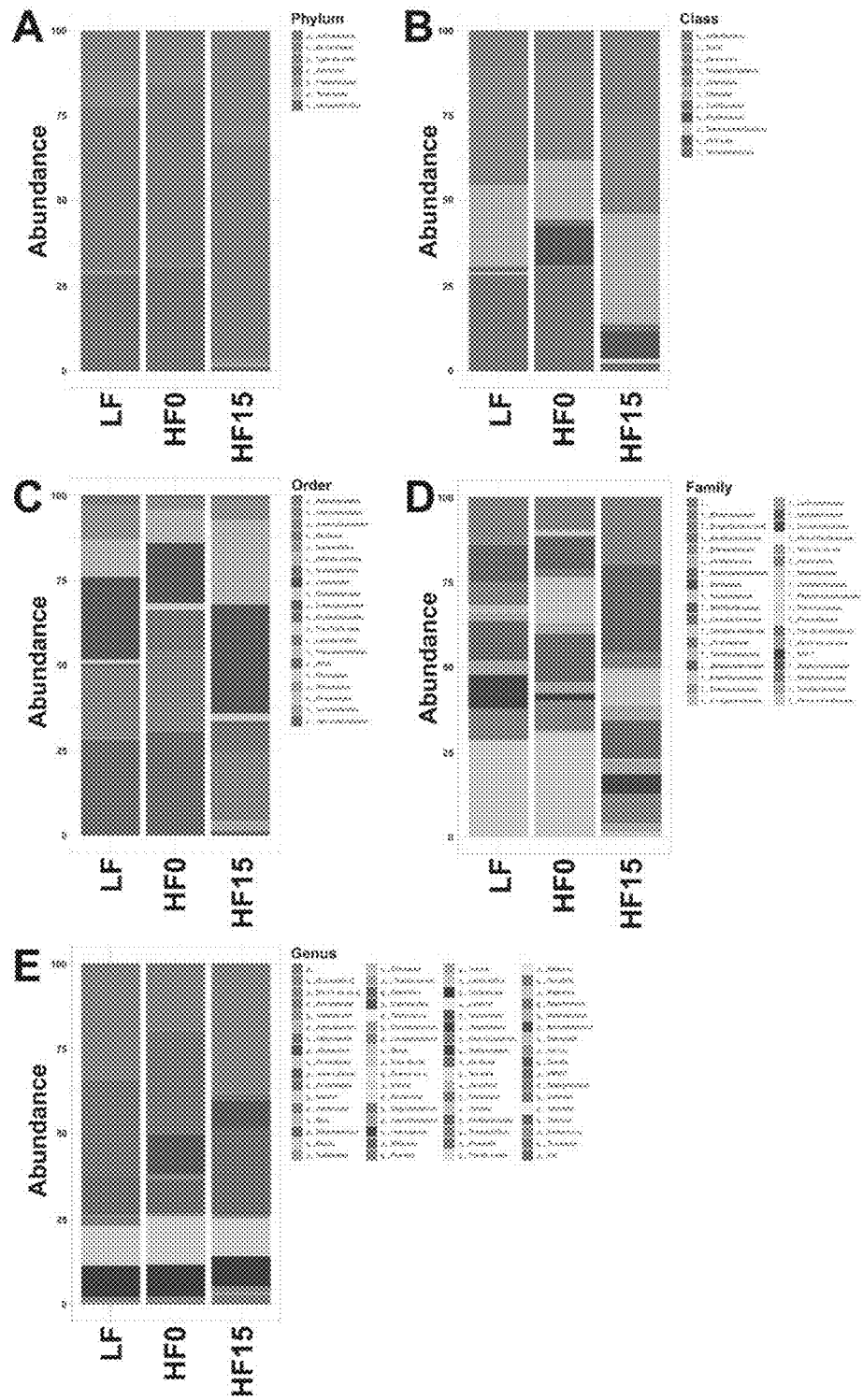
FIG. 25 shows that F&V supplementation changed bacterial community composition. Gut bacterial composition in different diets are shown in phylum level (A), class level (B), order level (C), family level (D) and genus level (E).
Figure 26:
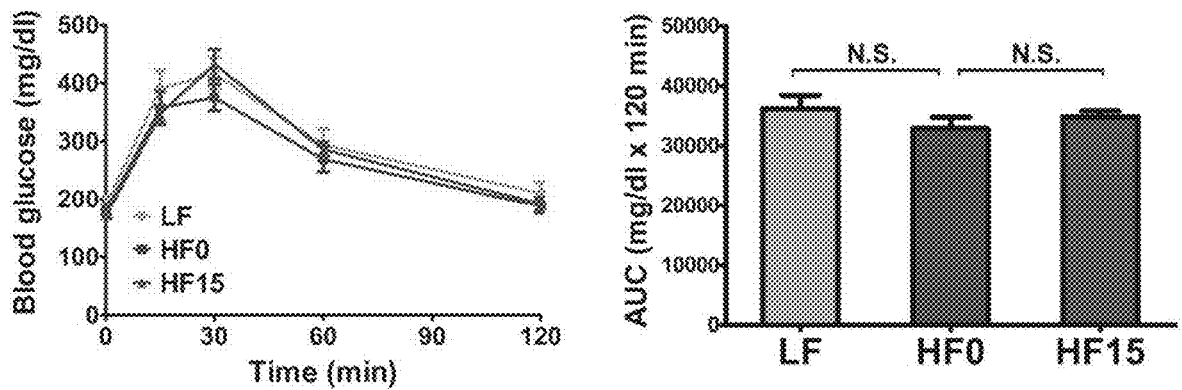
FIG. 26 shows that F&V supplementation changed bacterial community composition. Gut bacterial composition in different diets are shown in phylum level (A), class level (B), order level (C), family level (D) and genus level (E).
Figure 27:
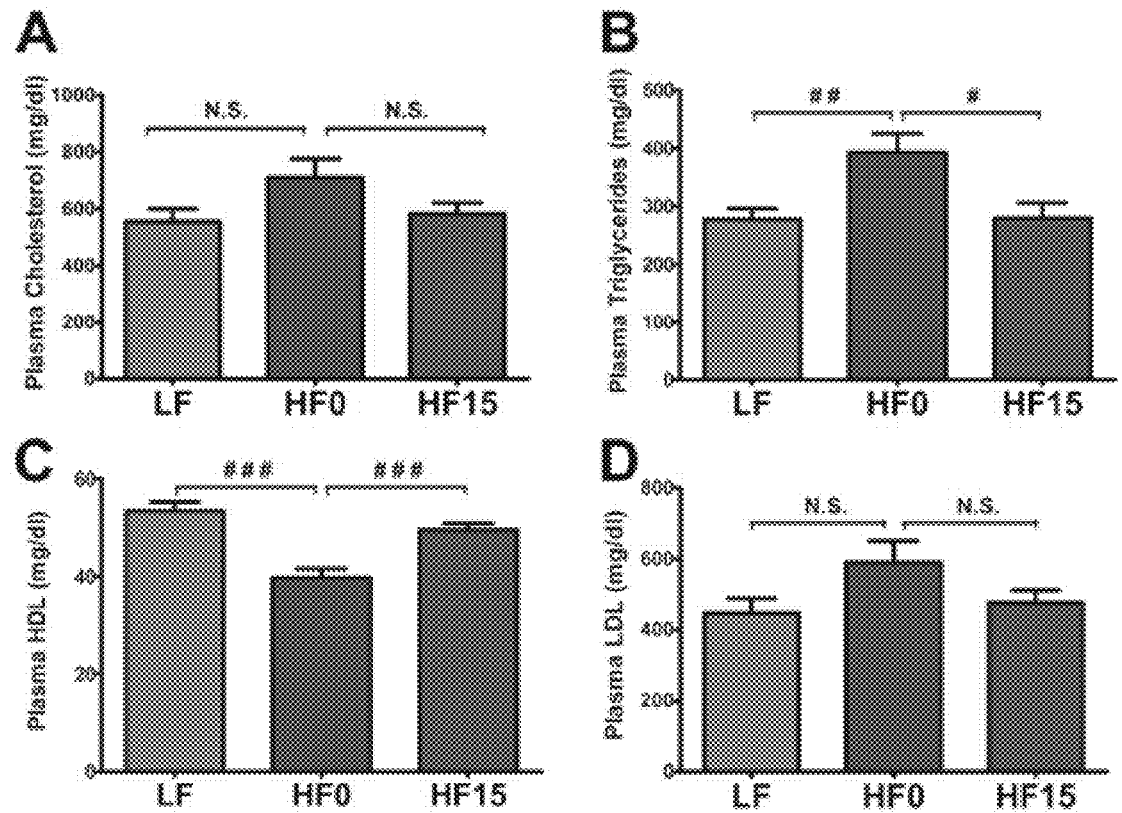
FIG. 27 shows lipidomic changes of lipoxin, 14, 15-EET, 20-HETE, and DHGLA in mice fed a diet with 15% F&V.
Figure 28:
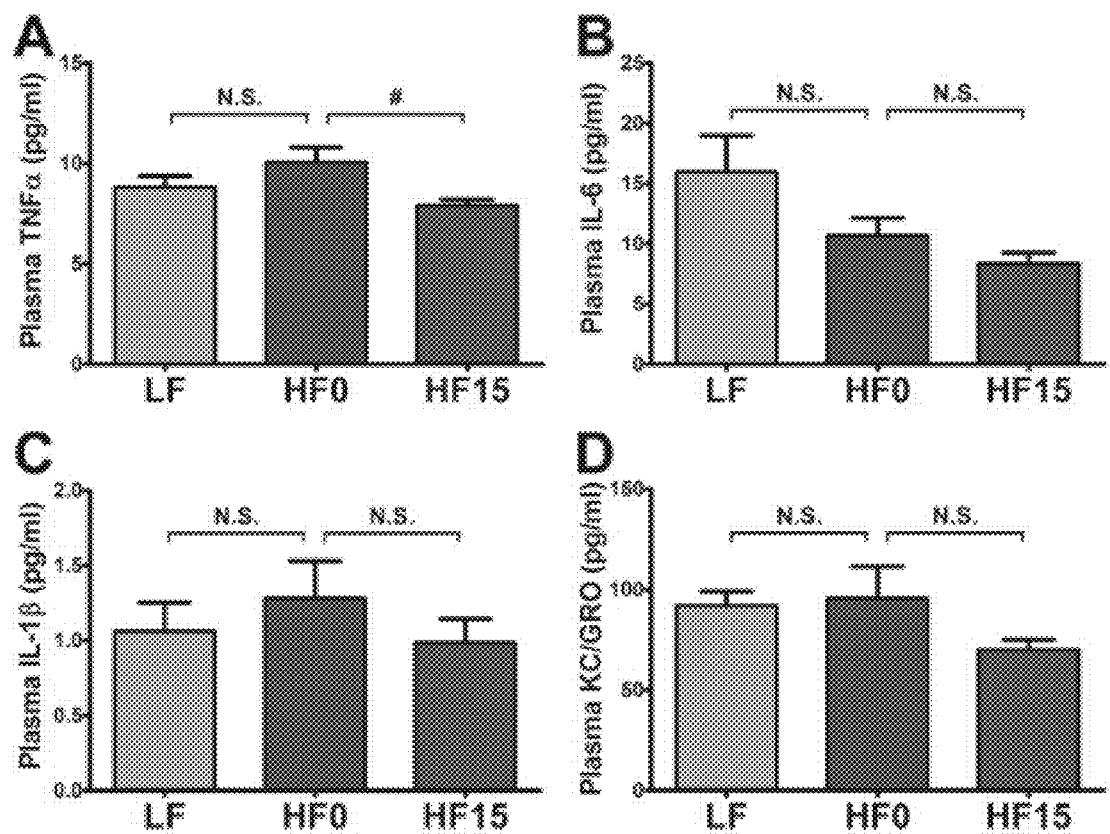
FIG. 28 shows that F&V supplementation reduced or had no impact on plasma cytokine levels in LDLR KO mouse. (A-H) Serum cytokine levels were determined by using the Meso Scale Discovery (MSD) multiplex ELISA platform.
Figure 28:
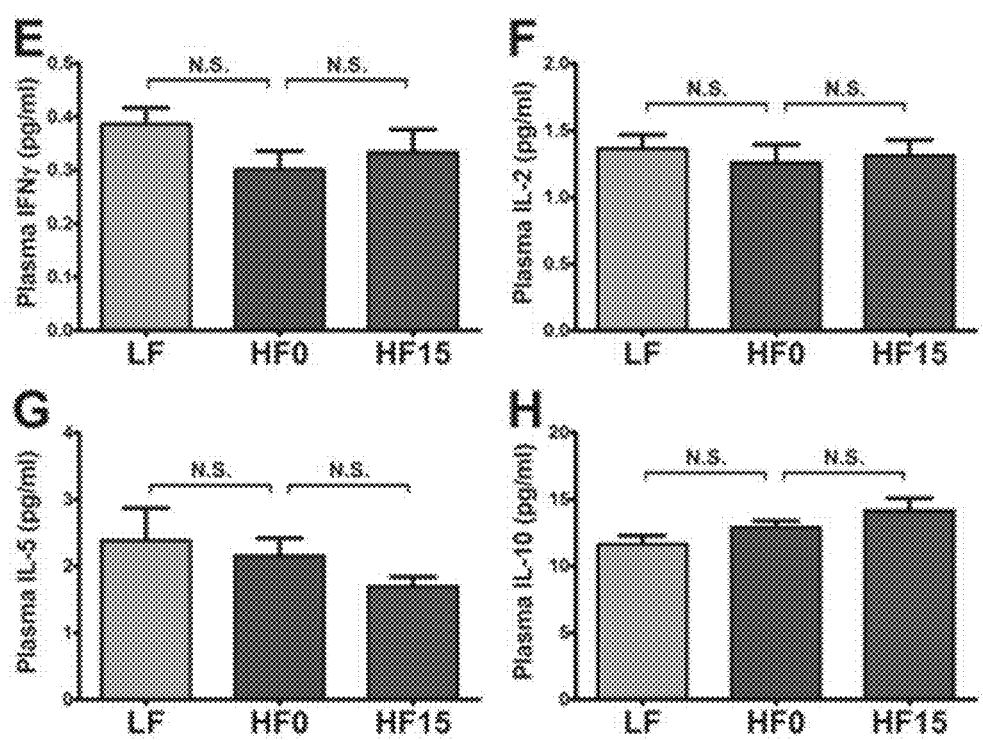

To evaluate the effects of F&V supplementation on the gut microbiota, 16S rRNA gene-based taxonomic profiling was performed. Compared to mice fed HF diets alone, it was found that mice fed the HF diets supplemented with F&V had significantly higher alpha diversity in fecal microbiota (FIG. 24A). Principal Coordinate Analysis showed shifts in gut microbiota composition of F&V consumption compared to both LF and HF diets (FIG. 24B).

REFERENCES FOR EXAMPLE 2

1. Meydani, M., et al., *Long-term vitamin E supplementation reduces atherosclerosis and mortality in Ldlr−/− mice, but not when fed Western style diet*. Atherosclerosis, 2014. 233(1): p. 196-205.
2. Callahan, B. J., et al., *Bioconductor Workflow for Microbiome Data Analysis: from raw reads to community analyses*. F1000Res, 2016. 5: p. 1492.
3. Goodrich, J. K., et al., *Conducting a microbiome study*. Cell, 2014. 158(2): p. 250-262.
4. Lozupone, C. A. and R. Knight, Species *divergence and the measurement of microbial diversity*. FEMS Microbiol Rev, 2008. 32(4): p. 557-78.
5. Ohta, H., et al., *Disruption of tumor necrosis factor-alpha gene diminishes the development of atherosclerosis in ApoE-deficient mice*. Atherosclerosis, 2005. 180(1): p. 11-7.
6. Branen, L., et al., *Inhibition of tumor necrosis factor-alpha reduces atherosclerosis in apolipoprotein E knock-out mice*. Arterioscler Thromb Vasc Biol, 2004. 24(11): p. 2137-42.
7. Paredes-Turrubiarte, G., et al., *Severity of non-alcoholic fatty liver disease is associated with high systemic levels of tumor necrosis factor alpha and low serum interleukin 10 in morbidly obese patients*. Clin Exp Med, 2016. 16(2): p. 193-202.
8. Seo, Y. Y., et al., *Tumor Necrosis Factor-alpha as a Predictor for the Development of Nonalcoholic Fatty Liver Disease: A 4-Year Follow-Up Study*. Endocrinol Metab (Seoul), 2013. 28(1): p. 41-5.
9. Zhang, Y., et al., *TNF-alpha promotes early atherosclerosis by increasing transcytosis of LDL across endothelial cells: crosstalk between NF-kappaB and PPAR-gamma*. J Mol Cell Cardiol, 2014. 72: p. 85-94.
10. McKellar, G. E., et al., *Role for TNF in atherosclerosis? Lessons from autoimmune disease*. Nat Rev Cardiol, 2009. 6(6): p. 410-7.
11. Boesten, L. S., et al., *Tumor necrosis factor-alpha promotes atherosclerotic lesion progression in APOE*3-Leiden transgenic mice*. Cardiovasc Res, 2005. 66(1): p. 179-85.
12. Diehl, A. M., *Tumor necrosis factor and its potential role in insulin resistance and nonalcoholic fatty liver disease*. Clin Liver Dis, 2004. 8(3): p. 619-38, x.
13. Kakino, S., et al., *Pivotal Role of TNF-alpha in the Development and Progression of Nonalcoholic Fatty Liver Disease in a Murine Model*. Horm Metab Res, 2018. 50(1): p. 80-87.

Example 3

Experiments are conducted to determine the effect of the F&V compositions described herein on lifespan of mice fed basal and HFD. It is contemplated that the compositions increase life and health span of mice and that the impact is more dramatic in those fed obesogenic diet. Similar to obesity, in aging, there is increase in oxidative stress, inflammation, increase in ceramide and alteration of gut microbiota. Many of the chronic and infectious disease associated with aging are also seen in obesity.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

The invention claimed is:

1. A composition, comprising:
a homogenized mixture of fruit species and a mixture of vegetables species comprising 11-18% oranges, 8-12% apples, 4-7% banana, 3-5% grapes, 2.0-4.5% watermelon, 2-5.5% pineapple, 1-3.5% strawberries, 1-3% cantaloupe, 1-3% lemons, 1-3% grapefruit, 1-3% peaches, 1-2% pears, 13-19% potato, 12-16% tomato, 2.5-5.5% sweet corn, 2-5% onions, 1.5-3.5% head lettuce, 0.5-1.5% romaine, 0.5-1.5% bell peppers, 0.5-1.5% carrots, 0.5-2% cucumbers, 1-2% cabbage, 0.5-2% dry beans, and 1-2% sweet potato; and one or more additional ingredients selected from the group consisting of enhancers, flavorants and colorants.

2. The composition of claim 1, wherein said homogenized mixture is a dry powder.

3. The composition of claim 2, wherein the homogenized mixture comprises 40-65 grams of dry powder.

4. The composition of claim 1, wherein the homogenized mixture comprises a polyphenol content of 15-25% hesperetin, 15-25% caffeoylquinic acid, 10-20% quercetin, and 5-15% malvidin.

5. The composition of claim 4, wherein the homogenized mixture comprises 20.6% hesperetin, 19.1% caffeoylquinic acid, 15.7% quercetin, and 10.3% malvidin.

6. The composition of claim 1, wherein the homogenized mixture further comprises 1-10% naringenin, 1-10% pelargonidin, 1-5% catechin, and 1-5% procyanidin.

7. The composition of claim 6, wherein the homogenized mixture comprises 6.5% naringenin, 5.8% pelargonidin, 4.2% catechin, and 3.1% procyanidin.

8. The composition of claim 1, wherein the composition further comprises one or more polyphenols selected from caffeic acid, peonidin, cyanidin, pinoresinol, p-Coumaroyl, luteolin, petunidin, daidzein, genistein, ellagic acid, and gallic acid.

9. The composition of claim 1, wherein the composition further comprises one or more of protein, carbohydrates, or fat.

10. The composition of claim 9, wherein the composition comprises 5-15% protein (kcal/kcal), 75-85% carbohydrates (kcal/kcal), and 0-20% fats (kcal/kcal).

11. The composition of claim 9, wherein the composition comprises 10-12% protein (kcal/kcal), 80-83% carbohydrates (kcal/kcal), and 5-10% fat (kcal/kcal).

12. The composition of claim 9, wherein the composition comprises 11.6% protein (kcal/kcal), 81.2% carbohydrates, and 7.2% fats (kcal/kcal).

13. The composition of claim 2, wherein the dry powder is a freeze-dried powder.

14. The composition of claim 1, wherein said composition is a nutritional supplement, food, or beverage.

15. A method of treating and/or preventing one or more conditions selected from weight gain, obesity, inflammatory conditions, fatty liver disease, high cholesterol, glucose intolerance, insulin resistance, low gut microbiota diversity, heart disease, and atherosclerosis in a subject, comprising: administering the composition of claim 1 to said subject.

16. A method of decreasing fat mass, increasing muscle mass, reducing inflammatory cytokines and/or ceramides, reducing tissue inflammation, decreasing cholesterol, improving glucose tolerance, improving immune response, increasing gut microbiota diversity, increasing lifespan, improving cognition, and/or improving bone health in a subject, comprising: administering the composition of claim 1 to said subject.

17. The method of claim 15, wherein said subject is a human.

18. The composition of claim 1, wherein said mixture of fruit and vegetable species comprises 13.64% oranges, 9.59% apples, 5.68% banana, 4.17% grapes, 3.28% watermelon, 2.92% pineapple, 2.01% strawberries, 1.94% cantaloupe, 1.91% lemons, 1.89% grapefruit, 1.76% peaches, 1.24% pears, 17.29% potato, 13.53% tomato, 3.78% sweet corn, 3.22% onions, 2.43% head lettuce, 1.67% romaine, 1.66% bell peppers, 1.55% carrots, 1.44% cucumbers, 1.21% cabbage, 1.12% dry beans, and 1.12% sweet potato.

19. A composition, comprising:
a homogenized mixture of fruit species and a mixture of vegetables species comprising 16-20% oranges, 14-18% tomatoes, 8-11% apples, 13-16% potatoes, 3.0-5.5% bananas, 3-4% sweet corn, 3-4% grapes, 2-3% lettuce, 1-2% escarole, 1-2% brussels sprouts, 1-2% cabbage, 1-2% carrots, 1-3% onions, 1-2% green peas, 0.5-1.5% watermelon, 0.5-1.5% honeydew melon, 0.5-1.5% broccoli, 1-2% spinach, 0.5-1.5% peppers, 0.5-1.5% snap beans, 0.5-1.5% cantaloupe, 0.4-1.2% cauliflower, 0.5-1.0% mangoes, 0.5-1.0% papaya, 0.3-0.9% celery, 0.4-1.2% cucumbers, 0.5-1.0% pineapple, 0.25-0.75% tangerines, 0.25-0.75% limes, 0.25-0.75% strawberries, 0.25-0.75% raspberries, 0.25-0.75% grapefruit, 0.25-0.75% lemons, 0.25-0.75% cranberries, 0.3-0.5% plums, 0.3-0.5% peaches, 0.3-0.5% cherries, 0.3-0.5% blueberries, 0.3-0.5% apricots, 0.1-0.15% dried peas, 0.1-0.15% great northern beans, 0.1-0.15% dried navy beans, 0.1-0.15% dried lentils, 0.1-0.15% pinto beans, 0.1-0.15% lima beans, 0.1-0.15% red kidney beans, and 0.1-0.15% black beans; and one or more additional ingredients selected from the group consisting of enhancers, flavorants and colorants.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
```

```
aagcttgctg gtgaaaagga                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
ttgcgctcat cttaggcttt                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ttgctctgtg aagggaatgg                                               20

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
ggctctgagg agtagacaat aaag                                          24

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cccttgatga agagggatca                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
actccacagg tgggaacaag                                               20
```